(12) United States Patent
Alsenz et al.

(10) Patent No.: US 11,938,136 B2
(45) Date of Patent: Mar. 26, 2024

(54) COMPOSITIONS FOR TREATING SPINAL MUSCULAR ATROPHY

(71) Applicant: Hoffmann-La Roche Inc., Little Falls, NJ (US)

(72) Inventors: Jochem Alsenz, Basel (CH); Olaf Grassmann, Basel (CH); Peter Kuehl, Basel (CH); Friedrich Metzger, Basel (CH); Kathleen Dorothy Mccarthy, Basel (CH); Eduardo Paulo Morawski Vianna, Basel (CH); Marvin Lloyd Woodhouse, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/685,431

(22) Filed: Nov. 15, 2019

(65) Prior Publication Data

US 2020/0323856 A1 Oct. 15, 2020

Related U.S. Application Data

(63) Continuation of application No. 15/955,337, filed on Apr. 17, 2018, now abandoned, which is a continuation of application No. PCT/EP2016/076905, filed on Nov. 8, 2016.

(30) Foreign Application Priority Data

Nov. 12, 2015 (EP) .................... 15194297

(51) Int. Cl.
| | |
|---|---|
| *A61K 31/519* | (2006.01) |
| *A61K 9/00* | (2006.01) |
| *A61K 9/08* | (2006.01) |
| *A61K 9/14* | (2006.01) |
| *A61K 31/5025* | (2006.01) |
| *A61K 31/575* | (2006.01) |
| *A61K 45/06* | (2006.01) |
| *A61K 47/12* | (2006.01) |
| *A61K 47/18* | (2017.01) |
| *A61K 47/22* | (2006.01) |
| *A61K 47/26* | (2006.01) |

(52) U.S. Cl.
CPC .......... *A61K 31/519* (2013.01); *A61K 9/0053* (2013.01); *A61K 9/0095* (2013.01); *A61K 9/08* (2013.01); *A61K 9/14* (2013.01); *A61K 9/145* (2013.01); *A61K 31/5025* (2013.01); *A61K 31/575* (2013.01); *A61K 45/06* (2013.01); *A61K 47/12* (2013.01); *A61K 47/183* (2013.01); *A61K 47/22* (2013.01); *A61K 47/26* (2013.01); *A61K 2300/00* (2013.01)

(58) Field of Classification Search
CPC ...... A61K 31/519; A61K 9/0095; A61K 9/14; A61K 9/145; A61K 31/5025; A61K 47/183; A61K 47/22
See application file for complete search history.

(56) References Cited

U.S. PATENT DOCUMENTS

| | | |
|---|---|---|
| 2002/0099208 A1 | 7/2002 | Yu et al. |
| 2006/0153920 A1 | 7/2006 | Amin et al. |
| 2012/0245156 A1 | 9/2012 | Nguyen et al. |

FOREIGN PATENT DOCUMENTS

| | | |
|---|---|---|
| DE | 2345064 | 4/1974 |
| FR | 2 914 188 A1 | 10/2008 |
| WO | 02/062290 A2 | 8/2002 |
| WO | 2004/082581 A2 | 9/2004 |
| WO | 2005/061513 A1 | 7/2005 |
| WO | 2008/142231 A3 | 11/2008 |
| WO | 2009/151546 A2 | 12/2009 |
| WO | 2010/019326 A1 | 2/2010 |
| WO | 2012/116965 A1 | 9/2012 |
| WO | 2013/020993 A1 | 2/2013 |
| WO | 2013/068769 A1 | 5/2013 |
| WO | 2013/068769 A1 | 7/2013 |
| WO | 2013/101974 A1 | 7/2013 |
| WO | 2013/112788 A1 | 8/2013 |
| WO | 2013/119916 A2 | 8/2013 |

(Continued)

OTHER PUBLICATIONS

Ankit Baheti et al., "Excipients used in lyophilization of small molecules" J.Excipients and Food Chem. 1(1):41-54 ( 2010).

(Continued)

*Primary Examiner* — Rayna Rodriguez

(74) *Attorney, Agent, or Firm* — Katherine J. Mackenzie

(57) ABSTRACT

The present invention provides pharmaceutical compositions comprising a compound of formula (I)

Figure 1:
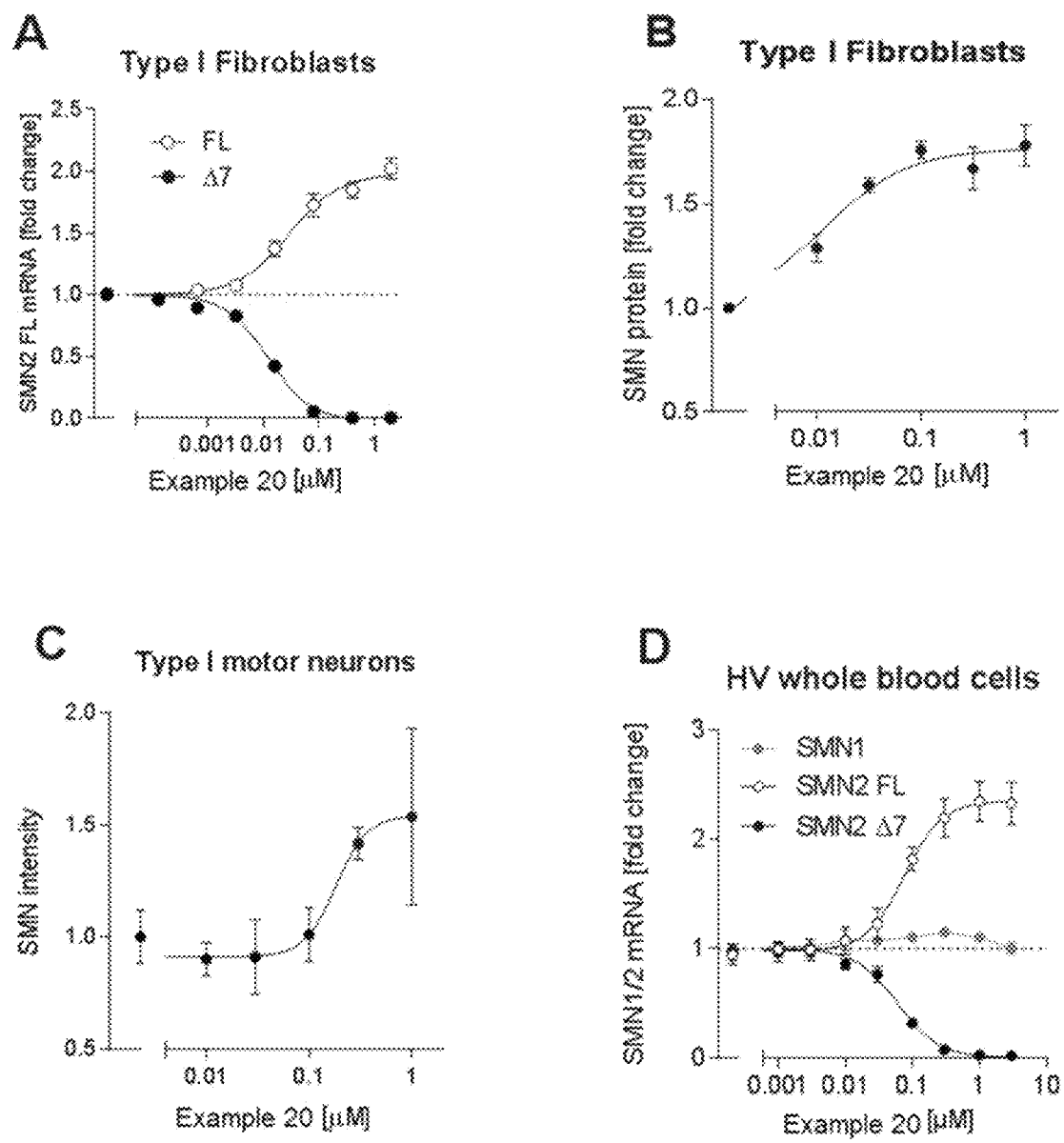

wherein A, $R^1$, $R^2$ and $R^3$ are as described herein, as well as pharmaceutically acceptable salts thereof. Further the present invention is concerned with the manufacture of the pharmaceutical compositions comprising a compound of formula (I) and their use as medicaments.

47 Claims, 9 Drawing Sheets

Specification includes a Sequence Listing.

(56) References Cited

FOREIGN PATENT DOCUMENTS

| WO | 2014/012050 A2 | 1/2014 |
| WO | 2014/184163 A1 | 11/2014 |
| WO | 2014/209841 A2 | 12/2014 |
| WO | 2015/173181 A1 | 11/2015 |
| WO | 2015/110446 A1 | 7/2016 |
| WO | 2017/080967 A1 | 5/2017 |

OTHER PUBLICATIONS

Brunhilde Wirth et al., "Moving towards treatments for spinal muscular atrophy: hopes and limits" Expert Opinion on Emerging Drugs 20(3):353-356 (Apr. 28, 2015).

Chiara Zanetta et al., "Molecula Therapeutic Strategies for Spinal Muscular Atrophies: Current and Future Clinical Trials" Clinical Therapeutics 36(1):128-140 (Dec. 17, 2013).

Combrink et al., "Respiratory syncytial virus fusion inhibitors. Part 6: An examination of the effect of structural variation of the benzimidazol-2-one heterocycle moiety" Bioorganic & Medicinal Chemistry Letters 17(17):4784-4790 (Aug. 4, 2007).

IPRP for PCT/EP2015/060343.

ISR and Written Opinion of PCT/EP2016/076905 (dated Feb. 9, 2017).

ISR and Written Opinion of PCT/EP2016/077190 (dated Mar. 1, 2017).

ISR for PCT/EP2015/063894.

ISR of PCT/EP2012/065499 (dated Sep. 20, 2012) WO2013/020993.

ISR of PCT/EP2014/059699 (dated Jul. 10, 2014) WO2014/184163.

ISR of PCT/EP2015/051066 (dated Feb. 6, 2015) WO2015/110446A1.

ISR of PCT/EP2015/060343 (dated Jul. 6, 2015) WO2015/173181.

ISR of PCT/EP2016/060952 (dated Jun. 16, 2016).

ISR of PCT/EP2016/079816 (dated Jan. 19, 2017).

Markus Riessland et al., "The benzamide M344, a novel histone deacetylase inhibitior, significantly increases SMN2 RNA/protein levels in spinal muscular atrophy cells" Hum Genet 120:101-110 (May 25, 2006).

Mehmood Yasir et al., "Excipients Use in Parenteral and Lyophilized Formulation Development" Open Science Journal of Pharmacy and Pharmacology 3(3):19-27 ( 2015).

N.A. Naryshkin et al., "SMN2 splicing modifiers improve motor function and Ingevity in mice with spinal muscular atrophy" Science 345(6197):688-693 (Aug. 8, 2014).

Pramanick et al., "Excipient selection in parenteral formulation development" Pharma Times 45(3):65-77 (Mar. 2013).

Seisuke Mimori et al., "Protective Effects of 4-Phenylbutyrate Derivatives on the Neuronal Cell Death and Endoplasmic Reticulum Stress" Biological & Pharmaceutical Bulletin of Japan 35(1):84-90 (Jan. 1, 2012).

Shalaev et al., "Thermophysical Properties of Pharmaceutically Compatible Buffers at Sub-Zero Temperatures: Implications for Freeze-Drying" Pharmaceutical Research 19(2):195-201 ( 2002).

Sin et al., "Respiratory syncytial virus fusion inhibitors. Part 7: Structure-activity relationships associated with a series of isatin oximes that demonstrate antiviral activity in vivo" Bioorganic & Medicinal Chemistry Letters 19(16):4857-4862 (Aug. 15, 2009).

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaggaaggt gctcacatt                                                    19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctttatgtt tttggcgtct tc                                                22

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
aaggagaaat gctggcatag agcagc                                            26
```

COMPOSITIONS FOR TREATING SPINAL MUSCULAR ATROPHY

CROSS-REFERENCE TO RELATED APPLICATIONS

This application is a continuation of U.S. application Ser. No. 15/955,337, filed Apr. 17, 2018, which is a continuation of International Application No. PCT/EP2016/076905, filed Nov. 8, 2016, which claims benefit of priority to EP Application No. 15194297.6 filed Nov. 12, 2015, each of which are incorporated herein by reference in its entirety.

SEQUENCE LISTING

The instant application contains a Sequence Listing which has been filed electronically in ASCII format and is hereby incorporated by reference in its entirety. Said ASCII copy, created on Mar. 24, 2020, is named P33204-US-1_SL.txt and is 1,043 bytes in size.

INTRODUCTION

The present invention provides pharmaceutical compositions comprising compounds which are SMN2 gene splicing modulators, their manufacture and their use for the treatment, delay of progression or amelioration of spinal muscular atrophy (SMA). Further, the pharmaceutical compositions of the invention may optionally comprise cytoprotectors. The invention further relates to the combined use of SMN2 gene splicing modulators and cytoprotectors for use in the treatment or amelioration of spinal muscular atrophy (SMA).

In particular, the present invention relates to pharmaceutical compositions comprising compounds of formula (I)

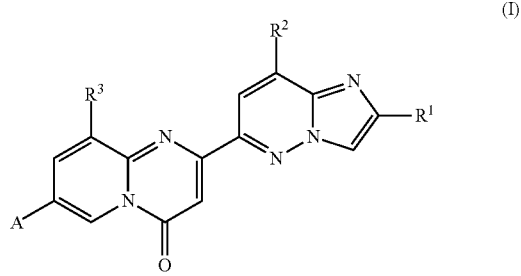

(I)

wherein A, $R^1$, $R^2$ and $R^3$ are as described herein, and pharmaceutically acceptable salts thereof.

BACKGROUND

Spinal muscular atrophy (SMA), in its broadest sense, describes a collection of inherited and acquired central nervous system (CNS) diseases characterized by progressive motor neuron loss in the spinal cord and brainstem causing muscle weakness and muscle atrophy. The most common form of SMA is caused by mutations in the Survival Motor Neuron (SMN) gene and manifests over a wide range of severity affecting infants through adults (Crawford and Pardo, *Neurobiol. Dis.*, 1996, 3:97).

Infantile SMA is the most severe form of this neurodegenerative disorder. Symptoms include muscle weakness, poor muscle tone, weak cry, limpness or a tendency to flop, difficulty sucking or swallowing, accumulation of secretions in the lungs or throat, feeding difficulties, and increased susceptibility to respiratory tract infections. The legs tend to be weaker than the arms and developmental milestones, such as lifting the head or sitting up, cannot be reached. In general, the earlier the symptoms appear, the shorter the lifespan. As the motor neuron cells deteriorate, symptoms appear shortly afterward. The severe forms of the disease are fatal and all forms have no known cure. The course of SMA is directly related to the rate of motor neuron cell deterioration and the resulting severity of weakness. Infants with a severe form of SMA frequently succumb to respiratory disease due to weakness in the muscles that support breathing. Children with milder forms of SMA live much longer, although they may need extensive medical support, especially those at the more severe end of the spectrum. The clinical spectrum of SMA disorders has been divided into the following five groups.

(a) Type 0 SMA (In Utero SMA) is the most severe form of the disease and begins before birth. Usually, the first symptom of Type 0 SMA is reduced movement of the fetus that can first be observed between 30 and 36 weeks of pregnancy. After birth, these newborns have little movement and have difficulties with swallowing and breathing.

(b) Type 1 SMA (Infantile SMA or Werdnig-Hoffmann disease) presents symptoms between 0 and 6 months. form of SMA is also very severe. Patients never achieve the ability to sit, and death usually occurs within the first 2 years without ventilatory support.

(c) Type 2 SMA (Intermediate SMA) has an age of onset at 7-18 months. Patients achieve the ability to sit unsupported, but never stand or walk unaided. Prognosis in this group is largely dependent on the degree of respiratory involvement.

(d) Type 3 SMA (Juvenile SMA or Kugelberg-Welander disease) is generally diagnosed after 18 months. Type 3 SMA individuals are able to walk independently at some point during their disease course but often become wheelchair-bound during youth or adulthood.

(e) Type 4 SMA (Adult onset SMA). Weakness usually begins in late adolescence in the tongue, hands, or feet, then progresses to other areas of the body. The course of adult SMA is much slower and has little or no impact on life expectancy.

The SMN gene has been mapped by linkage analysis to a complex region in chromosome 5q. In humans, this region contains an approximately 500 thousand base pairs (kb) inverted duplication resulting in two nearly identical copies of the SMN gene. SMA is caused by an inactivating mutation or deletion of the telomeric copy of the gene (SMN1) in both chromosomes, resulting in the loss of SMN1 gene function. However, all patients retain the centromeric copy of the gene (SMN2), and the copy number of the SMN2 gene in SMA patients generally correlates inversely with the disease severity; i.e., patients with less severe SMA have more copies of SMN2. Nevertheless, SMN2 is unable to compensate completely for the loss of SMN1 function due to alternative splicing of exon 7 caused by a translationally silent C to T mutation in exon 7. As a result, the majority of transcripts produced from SMN2 lack exon 7 (Δ7 SMN2), and encode a truncated SMN protein that has an impaired function and is rapidly degraded.

The SMN protein is thought to play a role in RNA processing and metabolism, having a well characterized function of mediating the assembly of a specific class of RNA-protein complexes termed snRNPs. SMN may have other functions in motor neurons, however its role in preventing the selective degeneration of motor neurons is not well established.

In most cases, SMA is diagnosed based on clinical symptoms and by the presence of at least one copy of the SMN1 gene test. However, in approximately 5% of cases SMA is caused by mutation in genes other than the inactivation of SMN 1, some known and others not yet defined. In some cases, when the SMN 1 gene test is not feasible or does not show any abnormality, other tests such as an electromyography (EMG) or muscle biopsy may be indicated.

Medical care for SMA patients at present is limited to supportive therapy including respiratory, nutritional and rehabilitation care; there is no drug known to address the underlying cause of the disease. Current treatment for SMA consists of prevention and management of the secondary effects of chronic motor unit loss. The major management issue in Type 1 SMA is the prevention and early treatment of pulmonary problems, which are the cause of death in the majority of the cases. While some infants afflicted with SMA grow to be adults, those with Type 1 SMA have a life expectancy of less than two years.

Several mouse models of SMA have been developed. In particular, the SMN delta exon 7 (Δ7 SMN) model (Le et al., Hum. Mol. Genet., 2005, 14:845) carries both the SMN2 gene and several copies of the Δ7 SMN2 cDNA and recapitulates many of the phenotypic features of Type 1 SMA. The Δ7 SMN model can be used for both SMN2 expression studies as well as the evaluation of motor function and survival. The C/C-allele mouse model (*Jackson Laboratory strain* #008714, The Jackson Laboratory, Bar Harbor, ME) provides a less severe SMA disease model, with mice having reduced levels of both SMN2 full length (FL SMN2) mRNA and SMN protein. The C/C-allele mouse phenotype has the SMN2 gene and a hybrid mSMN1-SMN2 gene that undergoes alternative splicing, but does not have overt muscle weakness. The C/C-allele mouse model is used for SMN2 expression studies.

As a result of improved understanding of the genetic basis and pathophysiology of SMA, several strategies for treatment have been explored, but none have yet demonstrated success in the clinic.

Gene replacement of SMN1, using viral delivery vectors, and cell replacement, using differentiated $SMN1^{+/+}$ stem cells, have demonstrated efficacy in animal models of SMA. More research is needed to determine the safety and immune response and to address the requirement for the initiation of treatment at the neonatal stage before these approaches can be applied to humans.

Correction of alternative splicing of SMN2 in cultured cells has also been achieved using synthetic nucleic acids as therapeutic agents: (i) antisense oligonucleotides that target sequence elements in SMN2 pre-mRNA and shift the outcome of the splicing reaction toward the generation of full length SMN2 mRNA (Passini et al., *Sci. Transl. Med.*, 2011, 3:72ra18; and, Hua et al., *Nature*, 2011, 478:123) and (ii) trans-splicing RNA molecules that provide a fully functional RNA sequence that replace the mutant fragment during splicing and generate a full length SMN1 mRNA (Coady and Lorson, *J Neurosci.*, 2010, 30:126).

Other approaches under exploration include searching for drugs that increase SMN levels, enhance residual SMN function, or compensate for its loss. Aminoglycosides have been shown to enhance expression of a stabilized SMN protein produced from Δ7 SMN2 mRNA by promoting the translational read-through of the aberrant stop codon, but have poor central nervous system penetration and are toxic after repeat dosing. Chemotherapeutic agents, such as aclarubicin, have been shown to increase SMN protein in cell culture; however, the toxicity profile of these drugs prohibits long-term use in SMA patients. Some drugs under clinical investigation for the treatment of SMA include transcription activators such as histone deacetylase ("HDAC") inhibitors (e.g., butyrates, valproic acid, and hydroxyurea), and mRNA stabilizers (mRNA decapping inhibitor RG3039 from Repligen), the goal being to increase the amount of total RNA transcribed from the SMN2 gene. However, the use of the HDAC inhibitors or mRNA stabilizers does not address the underlying cause of SMA and may result in a global increase in transcription and gene expression with potential safety problems in humans.

In an alternative approach, cytoprotective agents such as Olesoxime have been chosen for investigation. Such strategies are not aimed at SMN for the treatment of SMA, but instead have been developed to protect not only the SMN-deficient motor neurons from neurodegeneration, but also other systems affected by the disease, such as muscle cells. Olesoxime has shown clinical efficacy in the treatment of SMA Type 2 (Intermediate SMA) and SMA Type 3 (Juvenile SMA, non-ambulatory).

A system designed for identifying compounds that increase the inclusion of exon 7 of SMN into RNA transcribed from the SMN2 gene and certain benzooxazole and benzoisoxazole compounds identified thereby have been described in International Patent Application WO2009151546A1. A system designed for identifying compounds that cause ribosomal frameshifting to produce a stabilized SMN protein from Δ7 SMN2 mRNA and certain isoindolinone compounds identified thereby have been described in International Patent Applications WO2010/019236A1 and WO2013119916A2.

Olesoxime (Cholest-4-en-3-one oxime, (EZ)-N-(cholest-4-en-3-ylidene)hydroxylamine, CAS Registry Number 22033-87-0) is a cytoprotective drug that has been found to promote the function and survival of neurons and other cell types under disease-relevant stress conditions through interactions with the mitochondrial permeability transition pore (mPTP).

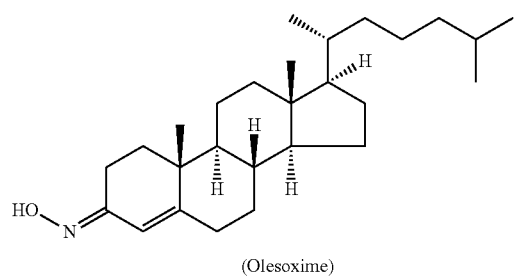

(Olesoxime)

WO 20047082581 (A2) describes the use of olesoxime for providing neuroprotection in a patient and WO 2008/142231 (A2) describes pharmaceutical compositions comprising it.

Methods of synthesizing oximes of d6-cholestenons and olesoxime have been described e.g. by Nobel prize laureate Adolf Friedrich Johann Butenandt (Butenandt A. et al., Berichte der Deutschen Chemischen Gesellschaft (1936), 69B, 882-8) or by Ponsold K. et al. (Journal fuer Praktische Chemie (1964), 23(3-4), 173-6).

Mode of action of olesoxime, its toxicity, metabolism, and pharmacodynamics have been described in Martin L. J. (IDrugs (2010) 13(8):568-80). In vivo, olesoxime rescues motor neurons from cell death induced by nerve lesion in neonatal rats and promotes nerve regeneration following a nerve crush in adult mice. By promoting both axonal regeneration and survival of motor neurons, olesoxime is a rational therapeutic approach for SMA. Additionally, there is evidence of functional improvement in nonclinical models of SMA.

At the molecular level, binding data indicated that olesoxime interacts with two outer mitochondrial membrane proteins which appears to modulate the opening of the mitochondrial permeability transition pore complex (mPTP). By binding to these proteins, olesoxime may preserve essential mitochondrial functions, such as calcium buffering in stressed neurons, thereby reducing cellular degeneration and death. The cytoprotective effects were observed in primary neurons subjected to physiological stress, in primary cardiomyocytes subjected to anthracycline toxicity and also in mouse hepatocytes submitted to Fas-induced apoptosis. Thus, olesoxime has the potential to reduce pathological, stress-induced, apoptosis in neuronal as well as non-neuronal cells. Therefore, these binding sites may play a role in the neuro-, cell- and tissue-protective action of olesoxime since stress-induced mitochondrial dysfunction has been implicated in most neurodegenerative diseases. In vivo, the motor neuron rescue and the nerve regeneration promotion observed with olesoxime treatment confirm that olesoxime acts both at the motor neuron cell body level, at the axonal level, and potentially has a protective effect on muscle (Pathak D et al. *J Biological Chemistry* (2015) 290(37): 22325-36).

Olesoxime has been developed for the treatment of Type 2 and Type 3 SMA. The clinical development program of olesoxime aimed at demonstrating maintenance of motor function over an observation period of two years. The clinical development of olesoxime in SMA includes two clinical studies, a Phase Ib PK and safety study (TRO19622CLEQ1115-1) using a hard capsule formulation, and a Phase II study (TRO19622CLEQ1275-1) using an oral suspension formulation. The placebo-controlled Phase II study (TRO19622CLEQ1275-1) is currently the largest and longest clinical study to have been conducted for this indication. The study showed maintenance of motor function over the two-year treatment period in the olesoxime arm compared with an approximately two-point decline in the primary endpoint (motor function measure [MFM]) in the placebo arm, which is in keeping with the reported natural disease progression (Vuillerot C et al. Arch Phys Med Rehabil (2013) 94(8):1555-61.). The Phase II study demonstrated a positive benefit-risk profile for olesoxime for the treatment of patients with Types 2 and 3 SMA.

Despite the progress made in understanding the genetic basis and pathophysiology of SMA, there remains a need to identify compounds and combinations of compounds and suitable forms of administration thereof that alter the course of spinal muscular atrophy, one of the most devastating childhood neurological diseases.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination amino-$C_{1-7}$-alkyl refers to a $C_{1-7}$-alkyl which is substituted by amino, or e.g. the combination arylalkylheterocycloalkyl refers to a heterocycloalkyl-radical which is substituted by an alkyl which is substituted by an aryl.

The term "moiety" refers to an atom or group of chemically bonded atoms that is attached to another atom or molecule by one or more chemical bonds thereby forming part of a molecule. For example, the variables A, R, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents.

Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The terms "compound(s) of this invention" and "compound(s) of the present invention" refer to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulae.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "chiral center" denotes a carbon atom bonded to four nonidentical substituents. The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light.

Compounds of the present invention can have one or more chiral centers and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. Whenever a chiral center is present in a chemical structure, it is intended that all stereoisomers associated with that chiral center are encompassed by the present invention.

The terms "halo", "halogen", and "halide" are used interchangeably herein and denote fluoro, chloro, bromo, or iodo. One particular example of halogen is fluoro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples for alkyl are methyl and ethyl.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl and the like. The term "perhaloalkyl" denotes an alkyl group where all hydrogen atoms of the alkyl group have been replaced by the same or different halogen atoms.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. One particular example of cycloalkyl is cyclopropyl.

The term "heterocycloalkyl" denotes a saturated or partly unsaturated mono-, bi- or tricyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples of a partly unsaturated heterocycloalkyl are dihydrofuryl, imidazolinyl, dihydro-oxazolyl, tetrahydro-pyridinyl, or dihydropyranyl. Particular examples of heterocycloalkyl are 1,4-diazepanyl, hexahydropyrrolo[1,2-a]pyrazinyl, piperidinyl, piperazinyl and pyrrolidinyl. More particular examples of heterocycloalkyl are hexahydropyrrolo[1,2-a]pyrazinyl and piperazinyl.

The term "N-heterocycloalkyl" denotes a heterocycloalkyl radical containing at least one nitrogen ring atom and where the point of attachment of the heterocycloalkyl radical to the rest of the molecule is through a nitrogen ring atom. Particular examples of N-heterocycloalkyl are 1,4-diazepanyl, hexahydropyrrolo[1,2-a]pyrazinyl, piperidinyl, piperazinyl and pyrrolidinyl. More particular examples of N-heterocycloalkyl are hexahydropyrrolo[1,2-a]pyrazinyl and piperazinyl.

The term "basicity" in reference to a compound is expressed herein by the negative decadic logarithm of the acidity constant of the conjugate acid (pKa=−log Ka). The larger the pKa of the conjugate acid, the stronger the base (pKa+pKb=14). In this application, an atom or functional group is denoted "basic" if it is suitable to accept a proton and if the calculated pKa of its conjugate acid is at least 7, more particularly if the calculated pKa of its conjugate acid is at least 7.8, most particularly if the calculated pKa of its conjugate acid is at least 8. pKa values were calculated in-silico as described in F. Milletti et al., *J Chem. Inf. Model* (2007) 47:2172-2181.

The term "alkylene" denotes a linear saturated divalent hydrocarbon group of 1 to 7 carbon atoms or a divalent branched saturated hydrocarbon group of 3 to 7 carbon atoms. Examples of alkylene groups include methylene, ethylene, propylene, 2-methylpropylene, butylene, 2-ethylbutylene, pentylene, hexylene. Particular examples for alkylene are ethylene, propylene, and butylene.

The term "amino" denotes a group of the formula —NR'R" wherein R' and R" are independently hydrogen, alkyl, alkoxy, cycloalkyl, heterocycloalkyl, aryl, heteroaryl or as described herein. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is a group other than hydrogen. The term "tertiary amino" denotes a group wherein both R' and R" are other than hydrogen. Particular secondary and tertiary amines are methylamine, ethylamine, propylamine, isopropylamine, phenylamine, benzylamine dimethylamine, diethylamine, dipropylamine and diisopropylamine.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The terms "individual" or "subject" refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The terms "treating" or "treatment" of a disease state include inhibiting the disease state, i.e., arresting the development of the disease state or its clinical symptoms, or relieving the disease state, i.e., causing temporary or permanent regression of the disease state or its clinical symptoms.

The term "spinal muscular atrophy" (or SMA) relates to a disease caused by an inactivating mutation or deletion in the SMN1 gene on both chromosomes, resulting in a loss of SMN1 gene function.

Symptoms of SMA include muscle weakness, poor muscle tone, weak cry, weak cough, limpness or a tendency to flop, difficulty sucking or swallowing, difficulty breathing, accumulation of secretions in the lungs or throat, clenched fists with sweaty hand, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

The term "treating spinal muscular atrophy (SMA)" or "treatment of spinal muscular atrophy (SMA)" includes one or more of the following effects: (i) reduction or amelioration of the severity of SMA; (ii) delay of the onset of SMA; (iii) inhibition of the progression of SMA; (iv) reduction of hospitalization of a subject; (v) reduction of hospitalization length for a subject; (vi) increase of the survival of a subject; (vii) improvement of the quality of life of a subject; (viii) reduction of the number of symptoms associated with SMA; (ix) reduction of or amelioration of the severity of one or more symptoms associated with SMA; (x) reduction of the duration of a symptom associated with SMA; (xi) prevention of the recurrence of a symptom associated with SMA; (xii) inhibition of the development or onset of a symptom of SMA; and/or (xiii) inhibition of the progression of a symptom associated with SMA.

More particular, the term "treating SMA" denotes one or more of the following beneficial effects: (i) a reduction in the loss of muscle strength; (ii) an increase in muscle strength; (iii) a reduction in muscle atrophy; (iv) a reduction in the loss of motor function; (v) an increase in motor neurons; (vii) a reduction in the loss of motor neurons; (viii) protection of SMN deficient motor neurons from degeneration; (ix) an increase in motor function; (x) an increase in pulmonary function; and/or (xi) a reduction in the loss of pulmonary function.

In further detail, the term "treating SMA" refers to the functional ability or retention of the functional ability for a human infant or a human toddler to sit up unaided or for a human infant, a human toddler, a human child or a human adult to stand up unaided, to walk unaided, to run unaided, to breathe unaided, to turn during sleep unaided, or to swallow unaided.

The term "$EC_{1.5x}$ concentration for production of full length SMN2 minigene mRNA" (or "$EC_{1.5x}$ minigene") is defined as that concentration of test compound that is effective in increasing the amount of full length SMN2 minigene mRNA to a level 1.5-fold greater relative to that in vehicle-treated cells.

The term "$EC_{1.5x}$ concentration for SMN protein expression" (or "$EC_{1.5x}$ SMN protein") is defined as that concentration of test compound that is effective in producing 1.5 times the amount of SMN protein in an SMA patient fibroblast cell compared to the amount produced from the vehicle control.

The term "half maximal effective concentration" (EC50) denotes the plasma concentration of a particular compound or molecule required for obtaining 50% of the maximum of a particular effect in vivo.

A "pharmaceutically acceptable carrier" refers to an ingredient in a pharmaceutical composition, other than an active ingredient, which is nontoxic to a subject. A pharmaceutically acceptable carrier includes, but is not limited to, a buffer or acidifier, excipient, stabilizer, or preservative.

The term "buffer" or "buffer system" denotes a pharmaceutically acceptable excipient or excipient mixture, which stabilizes the pH of a pharmaceutical preparation. Suitable buffers are well known in the art and can be found in the literature. Particular pharmaceutically acceptable buffers comprise citric buffer, malate buffer, maleate buffer, or tartrate buffer, most particularly tartrate buffer. Particular buffer systems of the invention combinations of organic acid and selected salts thereof, e.g. tribasic sodium citrate and citric acid, malic acid and sodium malate, potassium sodium tartrate and tartaric acid, or disodium tartrate and tartaric acid, particularly potassium sodium tartrate and tartaric acid. Alternatively, the organic acid (particularly tartaric acid) can be employed alone as "acidifier" instead of the combination of acid and the corresponding salt. Independently from the buffer used, the pH can be adjusted with an acid or a base known in the art, e.g. hydrochloric acid, acetic acid, phosphoric acid, sulfuric acid and citric acid, sodium hydroxide and potassium hydroxide. Particular acidifier is tartaric acid.

The term "antioxidant" denotes pharmaceutically acceptable excipients, which prevent oxidation of the active pharmaceutical ingredient. Antioxidants comprise ascorbic acid, glutathione, cysteine, methionine, citric acid, EDTA.

The term "surfactant" denotes a pharmaceutically acceptable excipient which is used to protect protein compositions against mechanical stresses like agitation and shearing. Examples of pharmaceutically acceptable surfactants include poloxamers, polysorbates, polyoxyethylene alkyl ethers (BRIJ®), alkylphenylpolyoxyethylene ethers (TRITON-X®) or sodium dodecyl sulfate (SDS).

The term "poloxamer" denotes non-ionic triblock copolymers composed of a central hydrophobic chain of poly(propylene oxide) (PPO) flanked by two hydrophilic chains of poly(ethylene oxide) (PEO), each PPO or PEO chain can be of different molecular weights. Poloxamers are also known by the trade name Pluronics. Particular Poloxamer is Poloxamer 188, a poloxamer wherein the PPO chain has a molecular mass of 1800 g/mol and a PEO content of 80% (w/w).

The term "polysorbate" denotes oleate esters of sorbitol and its anhydrides, typically copolymerized with ethylene oxide. Particular polysorbates are Polysorbate 20 (poly(ethylene oxide) (20) sorbitan monolaurate, TWEEN 20®) or Polysorbate 80 (poly(ethylene oxide) (80) sorbitan monolaurate, TWEEN 80®).

The "hydrophilic-lipophilic balance" (HLB) value denotes the degree of hydrophilicity of a non-ionic surfactant. The HLB value is determined by the ratio between the molecular mass of the hydrophilic portion of the surfactant molecule and its overall molecular mass, as described by Griffin W. C., *Journal of the Society of Cosmetic Chemists* (1949) 1:311.

The term "hydrophilic" denotes the capacity of a molecule or portion of a molecule to interact with polar solvents, in particular with water, or with other polar moieties driven by hydrogen bonding, dipole-ion interactions and/or dipole-dipole interactions.

The terms "lipophilic" and "hydrophobic" can be used interchangeably and denote the tendency of a molecule or portion of a molecule to dissolve in non-polar environment such as fats, oils, and non-polar solvents driven by London dispersion forces.

The "log P" value denotes the decimal logarithm of the partition coefficient P and is a measure of lipophilicity of a neutral uncharged compound. In instant application, the partition coefficient P is determined by the ratio between the concentration of solute in organic phase, particularly 1-octanol, and its concentration in aqueous phase at equilibrium.

Compounds of Formula (I)

In detail, the present invention relates to a pharmaceutical composition comprising a compound of formula (I)

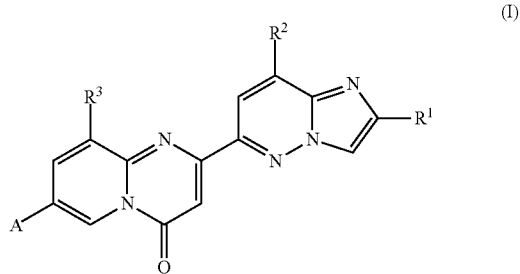

(I)

wherein
$R^1$ is hydrogen or $C_{1-7}$-alkyl;
$R^2$ is hydrogen, cyano, $C_{1-7}$-alkyl, $C_{1-7}$-haloalkyl or $C_{3-8}$-cycloalkyl;
$R^3$ is hydrogen, $C_{1-7}$-alkyl, or $C_{3-8}$-cycloalkyl;
A is N-heterocycloalkyl or $NR^{12}R^{13}$, wherein N-heterocycloalkyl comprises 1 or 2 nitrogen ring atoms and is optionally substituted with 1, 2, 3 or 4 substituents selected from $R^{14}$;
$R^{12}$ is heterocycloalkyl comprising 1 nitrogen ring atom, wherein heterocycloalkyl is optionally substituted with 1, 2, 3 or 4 substituents selected from $R^{14}$;
$R^{13}$ is hydrogen, $C_{1-7}$-alkyl or $C_{3-8}$-cycloalkyl;
$R^{14}$ is independently selected from hydrogen, $C_{1-7}$-alkyl, amino, amino-$C_{1-7}$-alkyl, $C_{3-8}$-cycloalkyl and heterocycloalkyl or two $R^{14}$ together form $C_{1-7}$-alkylene;
with the proviso that if A is N-heterocycloalkyl comprising only 1 nitrogen ring atom, then at least one $R^{14}$ substituent is amino or amino-$C_{1-7}$-alkyl;
or pharmaceutically acceptable salts thereof;

wherein the composition is an oral aqueous solution or a dry powder suitable for constitution of an oral aqueous solution.

A particular embodiment of the present invention is a pharmaceutical composition comprising a compound of formula (I) or pharmaceutically acceptable salts thereof.

Further, it is to be understood that every embodiment relating to a specific A, $R^1$, $R^2$ or $R^3$ as disclosed herein may be combined with any other embodiment relating to another A, $R^1$, $R^2$ or $R^3$ as disclosed herein.

In a particular embodiment of the present invention:
$R^1$ is hydrogen or $C_{1-7}$-alkyl;
$R^2$ is hydrogen, cyano, $C_{1-7}$-alkyl, $C_{1-7}$-haloalkyl or $C_{3-8}$-cycloalkyl;
$R^3$ is hydrogen, $C_{1-7}$-alkyl, or $C_{3-8}$-cycloalkyl;
A is N-heterocycloalkyl comprising 1 or 2 nitrogen ring atoms, wherein N-heterocycloalkyl is optionally substituted with 1, 2, 3 or 4 substituents selected from $R^{14}$;
$R^{14}$ is independently selected from hydrogen, $C_{1-7}$-alkyl, amino, amino-$C_{1-7}$-alkyl, $C_{3-8}$-cycloalkyl and heterocycloalkyl or two $R^{14}$ together form $C_{1-7}$-alkylene;
with the proviso that if A is N-heterocycloalkyl comprising only 1 nitrogen ring atom, then at least one $R^{14}$ substituent is amino or amino-$C_{1-7}$-alkyl.

In a particular embodiment of the present invention $R^1$ is $C_{1-7}$-alkyl, particularly methyl.

In a particular embodiment of the present invention $R^2$ is hydrogen or $C_{1-7}$-alkyl, particularly hydrogen or methyl.

In a particular embodiment of the present invention $R^3$ is hydrogen or $C_{1-7}$-alkyl, particularly hydrogen or methyl.

In a particular embodiment of the present invention $R^{12}$ is piperidinyl optionally substituted with 1, 2, 3 or 4 substituents selected from $R^{14}$.

In a particular embodiment of the present invention $R^{13}$ is hydrogen or $C_{1-7}$-alkyl, particularly hydrogen or methyl.

In a particular embodiment of the present invention $R^{14}$ is independently selected from $C_{1-7}$-alkyl and heterocycloalkyl or two $R^{14}$ together form $C_{1-7}$-alkylene.

In a particular embodiment of the present invention $R^{14}$ is independently selected from methyl, ethyl and pyrrolidinyl or two $R^{14}$ together form ethylene.

In a particular embodiment of the present invention A is a saturated mono- or bicyclic N-heterocycloalkyl comprising 1 or 2 nitrogen atoms and is optionally substituted with 1, 2, 3 or 4 substituents selected from $R^{14}$.

In a particular embodiment of the present invention the N-heterocycloalkyl in A or the heterocycloalkyl in $R^{12}$ as defined herein are substituted with 1 or 2 substituents selected from $R^{14}$.

In a particular embodiment of the present invention the N-heterocycloalkyl in A as defined herein is further characterized in that one ring nitrogen atoms is basic.

In a particular embodiment of the present invention A is

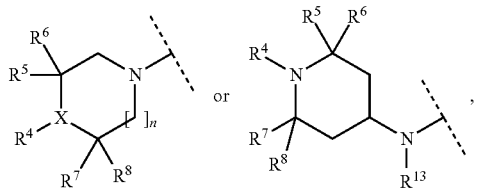

wherein
X is N or CH;
$R^4$ is hydrogen, $C_{1-7}$-alkyl or —$(CH_2)_m$-$NR^9R^{10}$;

$R^5$ is hydrogen or $C_{1-7}$-alkyl;
$R^6$ is hydrogen or $C_{1-7}$-alkyl;
$R^7$ is hydrogen or $C_{1-7}$-alkyl;
$R^8$ is hydrogen or $C_{1-7}$-alkyl;
$R^9$ and $R^{10}$ are independently selected from hydrogen, $C_{1-7}$-alkyl and $C_{3-8}$-cycloalkyl;
$R^{13}$ is hydrogen, $C_{1-7}$-alkyl or $C_{3-8}$-cycloalkyl;
n is 0, 1 or 2;
m is 0, 1, 2 or 3;
or $R^4$ and $R^5$ together form a $C_{1-7}$-alkylene;
or $R^4$ and $R^7$ together form a $C_{1-7}$-alkylene;
or $R^5$ and $R^6$ together form a $C_{2-7}$-alkylene;
or $R^5$ and $R^7$ together form a $C_{1-7}$-alkylene;
or $R^5$ and $R^9$ together form a $C_{1-7}$-alkylene;
or $R^7$ and R together form a $C_{2-7}$-alkylene;
or $R^7$ and $R^9$ together form a $C_{1-7}$-alkylene;
or $R^9$ and $R^{10}$ together form a $C_{2-7}$-alkylene;
with the proviso that if X is CH then $R^4$ is —$(CH_2)_m$—$NR^9R^{10}$; and
with the proviso that if X is N and $R^4$ is —$(CH_2)_m$—$NR^9R^{10}$ then m is 2 or 3.

It has been found that brain penetration is improved when at least one of $R^4$, $R^5$, $R^6$, $R^7$ and $R^8$ is not hydrogen.

In a particular embodiment of the invention at least one of $R^4$, $R^5$, $R^6$, $R^7$ and $R^8$ is other than hydrogen.

In a particular embodiment of the present invention X is N.

In a particular embodiment of the present invention n is 1.

In a particular embodiment of the present invention $R^4$ is hydrogen, methyl or —$(CH_2)_m$—$NR^9R^{10}$, more particularly hydrogen.

In a particular embodiment of the present invention $R^5$ is hydrogen, methyl or ethyl, more particularly methyl.

In a particular embodiment of the present invention $R^6$ is hydrogen or methyl, more particularly hydrogen.

In a particular embodiment of the present invention $R^7$ is hydrogen or methyl.

In a particular embodiment of the present invention $R^8$ is hydrogen.

In a particular embodiment of the present invention m is 0.

In a particular embodiment of the present invention $R^4$ and $R^5$ together form propylene.

In a particular embodiment of the present invention $R^5$ and $R^6$ together form ethylene; In a particular embodiment of the present invention $R^9$ and $R^{10}$ together form butylene.

In a particular embodiment of the present invention A is selected from the group of.

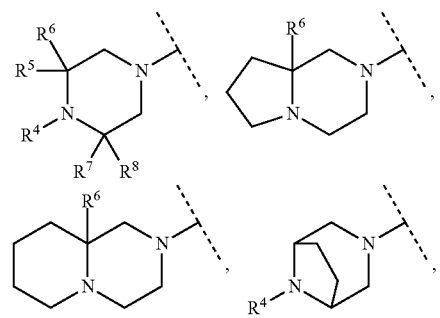

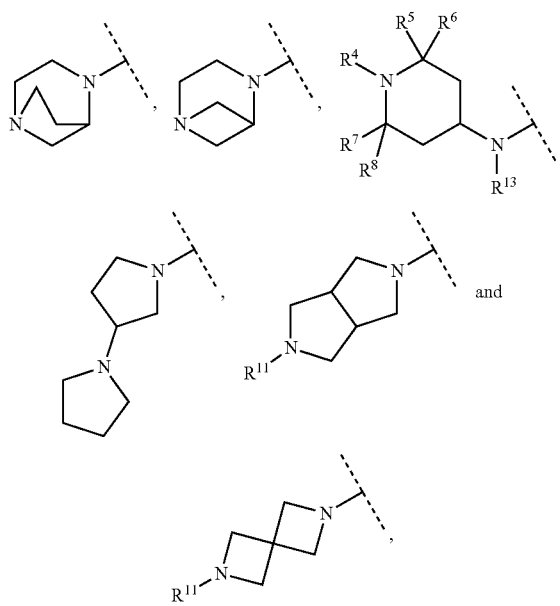

wherein $R^4$, $R^5$, $R^6$, $R^7$, $R^8$ and $R^{13}$ are as defined herein and wherein $R^{11}$ is hydrogen or $C_{1-7}$-alkyl.

In a particular embodiment of the present invention A is selected from the group of piperazinyl, diazepanyl, pyrrolidinyl and hexahydropyrrolo[1,2-a]pyrazinyl, each optionally substituted with 1, 2, 3 or 4 substituents selected from $R^{14}$ as defined herein.

In a particular embodiment of the present invention A is selected from the group of piperazin-1-yl, 1,4-diazepan-1-yl, pyrrolidin-1-yl and hexahydropyrrolo[1,2-a]pyrazin-2(1H)-yl, each optionally substituted with 1 or 2 substituents selected from $R^{14}$ as defined herein.

In a particular embodiment of the present invention A is $NR^{12}R^{13}$, wherein $R^{12}$ and $R^{13}$ are as described herein.

In a particular embodiment of the present invention A is selected from the group of:

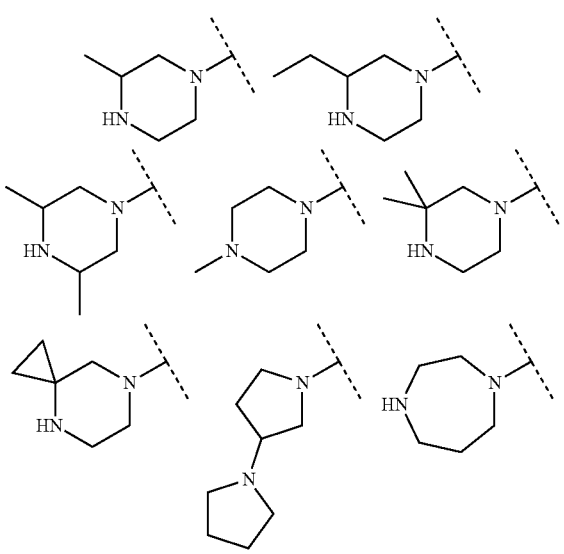

In a particular embodiment of the present invention $R^1$ is methyl, $R^2$ is hydrogen or methyl, $R^3$ is hydrogen, and A is In a particular embodiment of the present invention $R^1$ is methyl, $R^2$ is methyl, $R^3$ is hydrogen, and A is In a particular embodiment of the present invention the compound of formula (I) is selected from the group consisting of.

2-(2-methylimidazo[1,2-b]pyridazin-6-yl)-7-(4-methylpiperazin-1-yl)pyrido[1,2-a]pyrimidin-4-one;

7-[(8aR)-3,4,6,7,8,8a-hexahydro-1H-pyrrolo[1,2-a]pyrazin-2-yl]-2-(2-methylimidazo[1,2-b]pyridazin-6-yl)pyrido[1,2-a]pyrimidin-4-one;

7-[(8aS)-3,4,6,7,8,8a-hexahydro-TH-pyrrolo[1,2-a]pyrazin-2-yl]-2-(2,8-dimethylimidazo[1,2-b]pyridazin-6-yl)pyrido[1,2-a]pyrimidin-4-one;

7-[(8aR)-3,4,6,7,8,8a-hexahydro-TH-pyrrolo[1,2-a]pyrazin-2-yl]-2-(2,8-dimethylimidazo[1,2-b]pyridazin-6-yl)pyrido[1,2-a]pyrimidin-4-one;

7-[(8aS)-8a-methyl-1,3,4,6,7,8-hexahydropyrrolo[1,2-a]pyrazin-2-yl]-2-(2,8-dimethylimidazo[1,2-b]pyridazin-6-yl)pyrido[1,2-a]pyrimidin-4-one;

7-[(8aR)-8a-methyl-1,3,4,6,7,8-hexahydropyrrolo[1,2-a]pyrazin-2-yl]-2-(2,8-dimethylimidazo[1,2-b]pyridazin-6-yl)pyrido[1,2-a]pyrimidin-4-one;

2-(2,8-dimethylimidazo[1,2-b]pyridazin-6-yl)-7-[(3S,5R)-3,5-dimethylpiperazin-1-yl]pyrido[1,2-a]pyrimidin-4-one;

2-(2,8-dimethylimidazo[1,2-b]pyridazin-6-yl)-7-[(3S)-3-methylpiperazin-1-yl]pyrido[1,2-a]pyrimidin-4-one;

2-(2,8-dimethylimidazo[1,2-b]pyridazin-6-yl)-7-[(3R)-3-methylpiperazin-1-yl]pyrido[1,2-a]pyrimidin-4-one;

7-(1,4-diazepan-1-yl)-2-(2,8-dimethylimidazo[1,2-b]pyridazin-6-yl)pyrido[1,2-a]pyrimidin-4-one;

2-(2-methylimidazo[1,2-b]pyridazin-6-yl)-7-[(3S)-3-methylpiperazin-1-yl]pyrido[1,2-a]pyrimidin-4-one;

2-(2-methylimidazo[1,2-b]pyridazin-6-yl)-7-[(3R)-3-methylpiperazin-1-yl]pyrido[1,2-a]pyrimidin-4-one;

7-(1,4-diazepan-1-yl)-2-(2-methylimidazo[1,2-b]pyridazin-6-yl)pyrido[1,2-a]pyrimidin-4-one;

7-[(3R,5S)-3,5-dimethylpiperazin-1-yl]-2-(2-methylimidazo[1,2-b]pyridazin-6-yl)pyrido[1,2-a]pyrimidin-4-one;

7-[(8aS)-3,4,6,7,8,8a-hexahydro-TH-pyrrolo[1,2-a]pyrazin-2-yl]-2-(2-methylimidazo[1,2-b]pyridazin-6-yl)pyrido[1,2-a]pyrimidin-4-one;

7-[(8aS)-8a-methyl-1,3,4,6,7,8-hexahydropyrrolo[1,2-a]pyrazin-2-yl]-2-(2-methylimidazo[1,2-b]pyridazin-6-yl)pyrido[1,2-a]pyrimidin-4-one;

7-[(8aR)-8a-methyl-1,3,4,6,7,8-hexahydropyrrolo[1,2-a]pyrazin-2-yl]-2-(2-methylimidazo[1,2-b]pyridazin-6-yl)pyrido[1,2-a]pyrimidin-4-one;

2-(2,8-dimethylimidazo[1,2-b]pyridazin-6-yl)-7-[(3R)-3-pyrrolidin-1-ylpyrrolidin-1-yl]pyrido[1,2-a]pyrimidin-4-one;

7-(4,7-diazaspiro[2.5]octan-7-yl)-2-(2-methylimidazo[1,2-b]pyridazin-6-yl)pyrido[1,2-a]pyrimidin-4-one;

7-(4,7-diazaspiro[2.5]octan-7-yl)-2-(2,8-dimethylimidazo[1,2-b]pyridazin-6-yl)pyrido[1,2-a]pyrimidin-4-one;

2-(2-methylimidazo[1,2-b]pyridazin-6-yl)-7-[(3R)-3-pyrrolidin-1-ylpyrrolidin-1-yl]pyrido[1,2-a]pyrimidin-4-one;

2-(2,8-dimethylimidazo[1,2-b]pyridazin-6-yl)-7-(3,3-dimethylpiperazin-1-yl)pyrido[1,2-a]pyrimidin-4-one;

7-(3,3-dimethylpiperazin-1-yl)-2-(2-methylimidazo[1,2-b]pyridazin-6-yl)pyrido[1,2-a]pyrimidin-4-one;

2-(2,8-dimethylimidazo[1,2-b]pyridazin-6-yl)-9-methyl-7-[(3S)-3-methylpiperazin-1-yl]pyrido[1,2-a]pyrimidin-4-one;

2-(2,8-dimethylimidazo[1,2-b]pyridazin-6-yl)-9-methyl-7-[(3R)-3-methylpiperazin-1-yl]pyrido[1,2-a]pyrimidin-4-one;

2-(2,8-dimethylimidazo[1,2-b]pyridazin-6-yl)-7-[(3R,5S)-3,5-dimethylpiperazin-1-yl]-9-methyl-pyrido[1,2-a]pyrimidin-4-one;

2-(2,8-dimethylimidazo[1,2-b]pyridazin-6-yl)-7-(3,3-dimethylpiperazin-1-yl)-9-methyl-pyrido[1,2-a]pyrimidin-4-one;

7-(4,7-diazaspiro[2.5]octan-7-yl)-2-(2,8-dimethylimidazo[1,2-b]pyridazin-6-yl)-9-methyl-pyrido[1,2-a]pyrimidin-4-one;

2-(2,8-dimethylimidazo[1,2-b]pyridazin-6-yl)-7-[(3S,5S)-3,5-dimethylpiperazin-1-yl]pyrido[1,2-a]pyrimidin-4-one;

2-(2,8-dimethylimidazo[1,2-b]pyridazin-6-yl)-7-[(3S)-3-pyrrolidin-1-ylpyrrolidin-1-yl]pyrido[1,2-a]pyrimidin-4-one;

2-(2-methylimidazo[1,2-b]pyridazin-6-yl)-7-[(3S)-3-pyrrolidin-1-ylpyrrolidin-1-yl]pyrido[1,2-a]pyrimidin-4-one;

7-[(3S,5S)-3,5-dimethylpiperazin-1-yl]-2-(2-methylimidazo[1,2-b]pyridazin-6-yl)pyrido[1,2-a]pyrimidin-4-one;

9-methyl-2-(2-methylimidazo[1,2-b]pyridazin-6-yl)-7-[(3S)-3-methylpiperazin-1-yl]pyrido[1,2-a]pyrimidin-4-one;

9-methyl-2-(2-methylimidazo[1,2-b]pyridazin-6-yl)-7-[(3R)-3-methylpiperazin-1-yl]pyrido[1,2-a]pyrimidin-4-one;

7-[(3R,5S)-3,5-dimethylpiperazin-1-yl]-9-methyl-2-(2-methylimidazo[1,2-b]pyridazin-6-yl)pyrido[1,2-a]pyrimidin-4-one;

7-(3,3-dimethylpiperazin-1-yl)-9-methyl-2-(2-methylimidazo[1,2-b]pyridazin-6-yl)pyrido[1,2-a]pyrimidin-4-one;

7-(4,7-diazaspiro[2.5]octan-7-yl)-9-methyl-2-(2-methylimidazo[1,2-b]pyridazin-6-yl)pyrido[1,2-a]pyrimidin-4-one;

7-[(3S,5S)-3,5-dimethylpiperazin-1-yl]-9-methyl-2-(2-methylimidazo[1,2-b]pyridazin-6-yl)pyrido[1,2-a]pyrimidin-4-one;

7-[(3R)-3-ethylpiperazin-1-yl]-2-(2-methylimidazo[1,2-b]pyridazin-6-yl)pyrido[1,2-a]pyrimidin-4-one;

and pharmaceutically acceptable salts thereof.

In a particular embodiment of the present invention the compound of formula (I) is selected from the group consisting of 7-[(8aR)-3,4,6,7,8,8a-hexahydro-TH-pyrrolo[1,2-a]pyrazin-2-yl]-2-(2-methylimidazo[1,2-b]pyridazin-6-yl)pyrido[1,2-a]pyrimidin-4-one;

7-[(8aS)-3,4,6,7,8,8a-hexahydro-TH-pyrrolo[1,2-a]pyrazin-2-yl]-2-(2,8-dimethylimidazo[1,2-b]pyridazin-6-yl)pyrido[1,2-a]pyrimidin-4-one;

7-[(8aR)-3,4,6,7,8,8a-hexahydro-TH-pyrrolo[1,2-a]pyrazin-2-yl]-2-(2,8-dimethylimidazo[1,2-b]pyridazin-6-yl)pyrido[1,2-a]pyrimidin-4-one;

2-(2,8-dimethylimidazo[1,2-b]pyridazin-6-yl)-7-[(3S,5R)-3,5-dimethylpiperazin-1-yl]pyrido[1,2-a]pyrimidin-4-one;

7-[(3R,5S)-3,5-dimethylpiperazin-1-yl]-2-(2-methylimidazo[1,2-b]pyridazin-6-yl)pyrido[1,2-a]pyrimidin-4-one;

7-[(8aS)-3,4,6,7,8,8a-hexahydro-TH-pyrrolo[1,2-a]pyrazin-2-yl]-2-(2-methylimidazo[1,2-b]pyridazin-6-yl)pyrido[1,2-a]pyrimidin-4-one;

7-(4,7-diazaspiro[2.5]octan-7-yl)-2-(2-methylimidazo[1,2-b]pyridazin-6-yl)pyrido[1,2-a]pyrimidin-4-one;

7-(4,7-diazaspiro[2.5]octan-7-yl)-2-(2,8-dimethylimidazo[1,2-b]pyridazin-6-yl)pyrido[1,2-a]pyrimidin-4-one;

2-(2,8-dimethylimidazo[1,2-b]pyridazin-6-yl)-9-methyl-7-[(3S)-3-methylpiperazin-1-yl]pyrido[1,2-a]pyrimidin-4-one;

7-(4,7-diazaspiro[2.5]octan-7-yl)-2-(2,8-dimethylimidazo[1,2-b]pyridazin-6-yl)-9-methyl-pyrido[1,2-a]pyrimidin-4-one;

7-[(3R,5S)-3,5-dimethylpiperazin-1-yl]-9-methyl-2-(2-methylimidazo[1,2-b]pyridazin-6-yl)pyrido[1,2-a]pyrimidin-4-one;

7-(4,7-diazaspiro[2.5]octan-7-yl)-9-methyl-2-(2-methylimidazo[1,2-b]pyridazin-6-yl)pyrido[1,2-a]pyrimidin-4-one;

and pharmaceutically acceptable salts thereof.

A particular compound of formula (I) of the present invention is 7-[(8aR)-3,4,6,7,8,8a-hexahydro-1H-pyrrolo[1,2-a]pyrazin-2-yl]-2-(2-methylimidazo[1,2-b]pyridazin-6-yl)pyrido[1,2-a]pyrimidin-4-one or pharmaceutically acceptable salts thereof.

A particular embodiment of the present invention relates to a pharmaceutical composition comprising 7-[(8aR)-3,4,6,7,8,8a-hexahydro-H-pyrrolo[1,2-a]pyrazin-2-yl]-2-(2-methylimidazo[1,2-b]pyridazin-6-yl)pyrido[1,2-a]pyrimidin-4-one or a pharmaceutically acceptable salt thereof.

A particular compound of formula (I) of the present invention is 7-(4,7-diazaspiro[2.5]octan-7-yl)-2-(2,8-dimethylimidazo[1,2-b]pyridazin-6-yl)pyrido[1,2-a]pyrimidin-4-one or pharmaceutically acceptable salts thereof.

A particular embodiment of the present invention relates to a pharmaceutical composition comprising 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof.

Manufacturing Processes

Compounds of formula (I) and pharmaceutically acceptable salts thereof as defined above can be prepared following standard methods known in the art.

As illustrated in Scheme 1, the commercially available amino-pyridine of formula (II) can be reacted with a malonic ester to afford the intermediate of formula (III), wherein Y and $R^3$ are as described herein and R is $C_{1-2}$-alkyl, particularly methyl. The compound of formula (III) is then treated with a chlorinating reagent (such as $POCl_3$ and the like) to provide a compound of formula (IV). The compound of formula (IV) is then reacted in a Suzuki cross-coupling reaction with a compound of formula (V), wherein R¹ and R² are as described herein and Z is B(OH)₂ or an C₁₋₇-alkyl boronic acid ester such as 4,4,5,5-tetramethyl-1,3,2-dioxaborolan-2-yl, in the presence of a catalyst (such as (1,1'-bis (diphenylphosphino)ferrocene)palladium(II) dichloride (Pd (dppf)Cl₂) and the like) and a base (such as K₂CO₃ and the like) in a suitable solvent (such as DMF and the like), to afford the compound of formula (VI). Finally, the compound of formula (VI) is reacted with a compound M-A either in:

a) an aromatic nucleophilic substitution reaction (particularly if Y is fluoro) by heating at a temperature from 80° C. to 200° C.; or b) a Buchwald-Hartwig amination reaction in the presence of a palladium catalyst (e.g. tetrakis(triphenylphosphine)palladium (Pd(PPh₃)₄) or bis(dibenzylideneacetone)palladium (Pd(dba)₂) by heating at a temperature from 20° C. to 100° C.;

in a solvent (e.g. dimethyl sulfoxide (DMSO), N-methylpyrrolidone (NMP), or dimethylformamide (DMF)) to give a compound of formula (I), wherein A is as defined herein, M is hydrogen, sodium or potassium, particularly hydrogen, and wherein M is linked to A via a nitrogen atom of A.

Scheme 1.

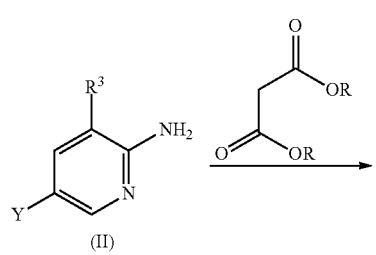

(II)

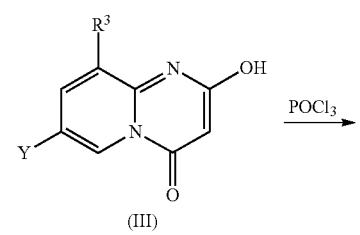

(III)

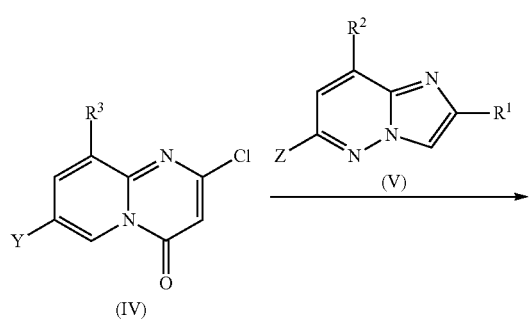

(IV)

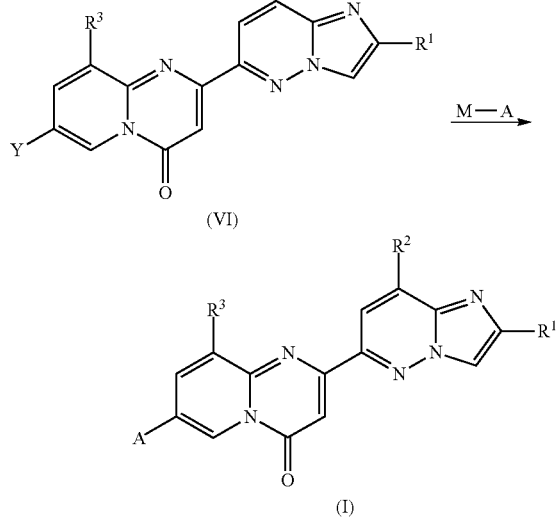

(VI)

In one embodiment, the invention relates to a process for the manufacture of compounds of formula (I) and pharmaceutically acceptable salts thereof as defined above, comprising the reaction of a compound of formula (VI) with a compound M-A either in:

a) an aromatic nucleophilic substitution reaction (particularly if Y is fluoro) by heating at a temperature from 80° C. to 200° C.; or b) a Buchwald-Hartwig amination reaction in the presence of a palladium catalyst (e.g. tetrakis(triphenylphosphine)palladium (Pd(PPh₃)₄) or bis(dibenzylideneacetone)palladium Pd(dba)₂) by heating at a temperature from 20° C. to 100° C.;

in a solvent (e.g. dimethyl sulfoxide (DMSO), N-methylpyrrolidone (NMP), or dimethylformamide (DMF)), wherein A, Y, R¹, R² and R³ are as defined herein, M is hydrogen, sodium or potassium, particularly hydrogen, and wherein M is linked to A via a nitrogen atom of A.

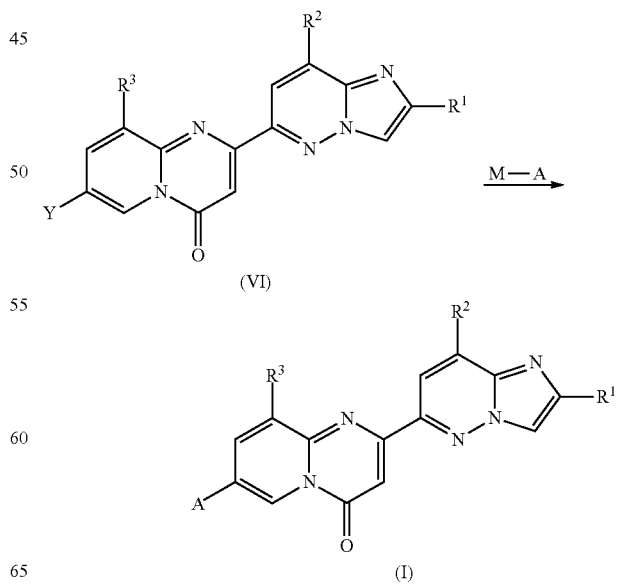

A particular embodiment of the invention relates to a process for the preparation of compounds of formula (I) and pharmaceutically acceptable salts thereof as defined above, comprising an aromatic nucleophilic substitution reaction between a compound of formula (VI) as described above with a compound of formula M-A by heating in a solvent, wherein A, $R^1$, $R^2$, $R^3$ and Y are as defined above, M is hydrogen, sodium or potassium, and wherein M is linked to A via a nitrogen atom of A.

A particular embodiment of the invention relates to a process for the preparation of compounds of formula (I) and pharmaceutically acceptable salts thereof as defined above, wherein the aromatic nucleophilic substitution reaction is performed at a temperature from 80° C. to 200° C.

A particular embodiment of the invention relates to a process for the preparation of compounds of formula (I) and pharmaceutically acceptable salts thereof as defined above, wherein the solvent of the aromatic nucleophilic substitution reaction is selected from dimethyl sulfoxide (DMSO), N-methylpyrrolidone (NMP), and dimethylformamide (DMF).

A particular embodiment of the invention relates to a process for the preparation of compounds of formula (I) and pharmaceutically acceptable salts thereof as defined above, wherein M is hydrogen.

Particularly, compounds of formula (I) and pharmaceutically acceptable salts thereof can be prepared in accordance to the methods described in the examples herein.

Medical Uses

As described above, the compounds of formula (I) and their pharmaceutically acceptable salts possess valuable pharmacological properties and have been found to enhance inclusion of exon 7 of SMN1 and/or SMN2 into mRNA transcribed from the SMN1 and/or SMN2 gene, thereby increasing expression of SMN protein in a human subject in need thereof.

The compounds of the present invention can be used, either alone or in combination with other drugs, for the treatment, prevention, delaying progression and/or amelioration of diseases caused by an inactivating mutation or deletion in the SMN1 gene and/or associated with loss or defect of SMN1 gene function. These diseases include, but are not limited to spinal muscular atrophy (SMA).

A particular embodiment of the present invention relates to a pharmaceutical composition comprising a compound of formula (I) or a pharmaceutically acceptable salt thereof as defined above and one or more pharmaceutically acceptable excipients for the treatment, prevention, delaying progression and/or amelioration of diseases caused by an inactivating mutation or deletion in the SMN1 gene and/or associated with loss or defect of SMN1 gene function, particularly for the treatment, prevention, delaying progression and/or amelioration of SMA.

A particular embodiment of the present invention relates to a pharmaceutical composition comprising a compound of formula (I) or a pharmaceutically acceptable salt thereof as defined above for use as therapeutically active substances, especially for use as therapeutically active substances for the treatment, prevention, delaying progression and/or amelioration of diseases caused by an inactivating mutation or deletion in the SMN1 gene and/or associated with loss or defect of SMN1 gene function, particularly for the treatment, prevention, delaying progression and/or amelioration of spinal muscular atrophy (SMA).

A particular embodiment of the present invention relates to a pharmaceutical composition comprising a compound of formula (I) or a pharmaceutically acceptable salt thereof as defined above for the use in the treatment, prevention, delaying progression and/or amelioration of diseases caused by an inactivating mutation or deletion in the SMN1 gene and/or associated with loss or defect of SMN1 gene function, particularly for use in the treatment, prevention, delaying progression and/or amelioration of spinal muscular atrophy (SMA).

A particular embodiment of the present invention relates to a method for the treatment, prevention, delaying progression and/or amelioration of diseases caused by an inactivating mutation or deletion in the SMN1 gene and/or associated with loss or defect of SMN1 gene function, particularly for the treatment, prevention, delaying progression and/or amelioration of spinal muscular atrophy (SMA), which method comprises administering a pharmaceutical composition comprising a compound of formula (I) or a pharmaceutically acceptable salt thereof as defined above to a subject.

A particular embodiment of the present invention relates to the use of a pharmaceutical composition comprising a compound of formula (I) or a pharmaceutically acceptable salt thereof as defined above for the treatment, prevention, delaying progression and/or amelioration of diseases caused by an inactivating mutation or deletion in the SMN1 gene and/or associated with loss or defect of SMN1 gene, particularly for the treatment, prevention, delaying progression and/or amelioration of spinal muscular atrophy (SMA).

A particular embodiment of the present invention relates to the use of a pharmaceutical composition comprising a compound of formula (I) or a pharmaceutically acceptable salt thereof as defined above for the preparation of medicaments for the treatment, prevention, delaying progression and/or amelioration of diseases caused by an inactivating mutation or deletion in the SMN1 gene and/or associated with loss or defect of SMN1 gene function, particularly for the treatment, prevention, delaying progression and/or amelioration of spinal muscular atrophy (SMA). Such medicaments comprise compounds of formula (I) or their pharmaceutically acceptable salts as defined above.

Combinations

Cytoprotectors (such as olesoxime) and SMN2 gene splicing modulators (such as the compounds of formula (I)) are complementary approaches to treating Spinal Muscular Atrophy (SMA). There is supportive evidence to suggest that co-administration of cytoprotectors and SMN2 gene splicing modulators as a combination treatment will provide additional benefit to all types of SMA patients. The extent of added benefit can be quantified through studies of combination treatment in SMA mouse models.

A particular SMN2 gene splicing modulator of the invention is a compound of formula (I) as described herein or a pharmaceutically acceptable salt thereof.

A particular cytoprotector of the invention is olesoxime.

Systemically low levels of SMN protein cause SMA. α-Motor neurons of the spinal cord are considered particularly vulnerable in this genetic disorder and their dysfunction and loss cause progressive muscle weakness, paralysis and eventually premature death of afflicted individuals. Historically, SMA was therefore considered a motor neuron-autonomous disease. However, depletion of SMN in motor neurons of normal mice elicited only a very mild phenotype (Park et al, J Neurosci. 2010 Sep. 8; 30(36):12005-19). Conversely, restoration of SMN to motor neurons in an SMA mouse model had only modest effects on the SMA phenotype and survival (Hua et al Nature. 2011 Oct. 5; 478(7367):123-6). Collectively, these results suggest that additional cell types contribute to the pathogenesis of SMA, and understanding the non-autonomous requirements is crucial for developing effective therapies.

Current research points to SMA as a multi-cell, -tissue, -system disorder. There are several in vitro, in vivo studies, as well as human case studies showing that a variety of tissues are affected in SMA, such as: afferent nerves, muscle, vasculature, brain, heart and pancreas (Hamilton and Gillingwater, et al, Trends Mol Med. 2013 January; 19(1):40-50. For example, there is a body of work that shows a muscle intrinsic defects in SMA, indicating that SMN plays a role in muscle development and regeneration (Boyer et al, Front Physiol. 2013 Dec. 18; 4:356; Hayhurst M et al., Dev Biol. 2012 Aug. 15; 368(2):323-34; Briccino et al, Hum Mol Genet. 2014 Sep. 15; 23(18):4745-57; Shafey et al, Exp Cell Res. 2005 Nov. 15; 311(1):49-61., Cifuentes-Diaz et al, J Cell Biol. 2001 Mar. 5; 152(5):1107-14; Martinez et al J Neurosci. 2012 Jun. 20; 32(25):8703-15. This highlights the importance of muscle-targeted treatments for SMA patients. Many therapeutic strategies target restoring SMN protein. Antisense oligonucleotides and gene therapy potential treatments target increasing SMN in the CNS tissue alone. Effectively targeting treatment to other key affected cells and tissues remains a challenge.

The cytoprotector olesoxime and the SMN2 gene splicing modulators of formula (I) can both be administered orally and are distributed systemically. Moreover, they have complementary mechanisms of action. Olesoxime is cytoprotective by preserving the mitochondrial membrane and preventing mitochondrial dysfunction, an important element of disease pathophysiology in SMA. Mitochondria are particularly abundant in energy-demanding cells, such as motor neurons and muscle cells, both identified as target treatment tissues in SMA. The SMN2 gene splicing modulators of formula (I) target increasing SMN protein systemically.

The SMN2 gene splicing modulators of formula (I) correct SMN protein at the RNA level through correcting mis-splicing of the SMN pre-mRNA. The maximal increase in SMN protein in SMA motor neurons and fibroblasts above untreated cells resulted in a similar increase in both cell types (60-80%). Moreover, in both the severe and mild models of SMA, mice treated with SMN2 gene splicing modulators of formula (I) had an increase in SMN protein reaching approximately 43% (brain) and 55% (muscle) of protein levels in heterozygous mice. The increase in protein was sufficient to provide substantial benefit, restoring connectivity at the neuromuscular junctions (NMJ), and on survival in the severe mice treated with compounds of formula (I). Given that the increase in protein is not corrected to 100% of heterozygous mice or wildtype mice, it is reasonable to believe that there may be additional improvements with co-treatments, especially treatments that target other mechanisms of disease pathogenesis.

In vitro binding studies and oxidative stress assays indicate that the cytoprotector olesoxime preserves the mitochondrial membrane in a disease where there is evidence of mitochondrial dysfunction (SMA), thereby preventing cell death. In vitro fluorescence imaging experiments showed that olesoxime accumulates at the membrane level of mitochondria in neurons. In addition, in olesoxime treated SOD1 mice (severe familial ALS model) the neuromuscular junctions (NMJ) were preserved when treated early. Thus, olesoxime could provide additional and complementary benefit through mitochondrial and cytoprotective mechanisms.

The additional benefit of the combination treatment of the cytoprotector olesoxime and the SMN2 gene splicing modulators of formula (I) are being confirmed in a mild mouse model of SMA. The mild model was generated by treating the severe SMA delta7 mouse model with a low dose of an SMN splicing modulator. In the study, the cytoprotector olesoxime and the SMN2 gene splicing modulators of formula (I) are tested alone and in combination. The impact of treatment on mouse NMJs is the primary endpoint of these studies, given the importance of this phenotype. Oxidative stress markers in muscle tissues are also evaluated.

A compound of formula (I) or a pharmaceutically acceptable salt thereof can be combined with olesoxime in one single pharmaceutical composition (e.g. a fixed dose combination) or a compound of formula (I) or a pharmaceutically acceptable salt thereof and olesoxime can be co-administered sequentially one after the other.

As described herein, the co-administration of a compound of formula (I) and olesoxime can have beneficial and synergistic effects for the treatment, prevention, delaying progression and/or amelioration of diseases caused by an inactivating mutation or deletion in the SMN1 gene and/or associated with loss or defect of SMN1 gene function, and additionally for the protection of cells implicated in the pathophysiology of the disease, particularly for the treatment, prevention, delaying progression and/or amelioration of spinal muscular atrophy (SMA).

In the context of the present invention, the term "co-administration" of two API can be simultaneous, almost simultaneous, or delayed in time by a few days or weeks, for example by up to 4 or 5 weeks.

The compounds of the present invention can be used in combination with cytoprotectors such as olesoxime for the treatment, prevention, delaying progression and/or amelioration of diseases caused by an inactivating mutation or deletion in the SMN1 gene and/or associated with loss or defect of SMN1 gene function, and additionally for the protection of cells implicated in the pathophysiology of the disease. These diseases include, but are not limited to spinal muscular atrophy (SMA).

In a particular embodiment, the present invention would show a synergy of a combination of a compound of formula (I) with olesoxime either alone or in combination thereof in the treatment, prevention, delaying progression and/or amelioration of diseases caused by an inactivating mutation or deletion in the SMN1 gene and/or associated with loss or defect of SMN1 gene function, and additionally for the protection of cells implicated in the pathophysiology of the disease, particularly for the treatment, prevention, delaying progression and/or amelioration of spinal muscular atrophy (SMA).

A particular embodiment of the present invention relates to a pharmaceutical composition comprising a compound of formula (I) or a pharmaceutically acceptable salt thereof and olesoxime and one or more pharmaceutically acceptable excipients for use in the treatment, prevention, delaying progression and/or amelioration of diseases caused by an inactivating mutation or deletion in the SMN1 gene and/or associated with loss or defect of SMN1 gene function, and additionally for the protection of cells implicated in the pathophysiology of the disease, particularly for the treatment, prevention, delaying progression and/or amelioration of SMA.

A particular embodiment of the present invention relates to a pharmaceutical composition comprising a compound of formula (I) or a pharmaceutically acceptable salt thereof and olesoxime for use as therapeutically active substances, especially for use as therapeutically active substances for the treatment, prevention, delaying progression and/or amelioration of diseases caused by an inactivating mutation or deletion in the SMN1 gene and/or associated with loss or defect of SMN1 gene function, and additionally for the protection of cells implicated in the pathophysiology of the disease, particularly for the treatment, prevention, delaying progression and/or amelioration of spinal muscular atrophy (SMA).

A particular embodiment of the present invention relates to a pharmaceutical composition comprising a compound of formula (I) or a pharmaceutically acceptable salt thereof and olesoxime for use in the treatment, prevention, delaying progression and/or amelioration of diseases caused by an inactivating mutation or deletion in the SMN1 gene and/or associated with loss or defect of SMN1 gene function and additionally for the protection of cells implicated in the pathophysiology of the disease, particularly for use in the treatment, prevention, delaying progression and/or amelioration of spinal muscular atrophy (SMA).

A particular embodiment of the present invention relates to a method for the treatment, prevention, delaying progression and/or amelioration of diseases caused by an inactivating mutation or deletion in the SMN1 gene and/or associated with loss or defect of SMN1 gene function and additionally for the protection of cells implicated in the pathophysiology of the disease, particularly for the treatment, prevention, delaying progression and/or amelioration of spinal muscular atrophy (SMA), which method comprises administering a pharmaceutical composition comprising a compound of formula (I) or a pharmaceutically acceptable salt thereof and olesoxime to a subject.

A particular embodiment of the present invention relates to the use of a pharmaceutical composition comprising a compound of formula (I) or a pharmaceutically acceptable salt thereof and olesoxime for the treatment, prevention, delaying progression and/or amelioration of diseases caused by an inactivating mutation or deletion in the SMN1 gene and/or associated with loss or defect of SMN1 gene function and additionally for the protection of cells implicated in the pathophysiology of the disease, particularly for the treatment, prevention, delaying progression and/or amelioration of spinal muscular atrophy (SMA).

A particular embodiment of the present invention relates to the use of a compound of formula (I) or a pharmaceutically acceptable salt thereof and olesoxime for the preparation of medicaments for the treatment, prevention, delaying progression and/or amelioration of diseases caused by an inactivating mutation or deletion in the SMN1 gene and/or associated with loss or defect of SMN1 gene function, and additionally for the protection of cells implicated in the pathophysiology of the disease, particularly for the treatment, prevention, delaying progression and/or amelioration of spinal muscular atrophy (SMA). Such medicaments comprise compounds of formula (I) or their pharmaceutically acceptable salts and olesoxime.

The present invention therefore also encompasses a kit for the preparation of pharmaceutical compositions comprising a compound of formula (I) or a pharmaceutically acceptable salt thereof and olesoxime.

In one embodiment the invention provides a kit comprising (a) a first pharmaceutical composition comprising a therapeutically effective amount of (i) a compound of formula (I), and (ii) a pharmaceutically acceptable carrier, (b) a second pharmaceutical composition comprising (i) olesoxime, and (ii) a pharmaceutically acceptable carrier, (c) prescribing information, and (d) a container, wherein the prescribing information includes advice to a patient regarding co-administration of the two API.

In another embodiment the invention provides a kit comprising a composition comprising a therapeutically effective amount of a compound of formula (I) and olesoxime, prescribing information also known as "leaflet", a blister package or bottle (HDPE or glass) and a container.

The term "kit" as used herein refers to a collection of the aforementioned components which may be provided separately or within a single container. The container optionally comprises instructions for carrying out the method of the present disclosure.

One embodiment of the invention provides a combination of a SMN2 gene splicing modulator and a cytoprotector.

One embodiment of the invention provides a combination of a SMN2 gene splicing modulator and a cytoprotector, for use in the treatment, prevention, delaying progression and/or amelioration of diseases caused by an inactivating mutation or deletion in the SMN1 gene and/or associated with loss or defect of SMN1 gene function, and/or for the protection of cells implicated in the pathophysiology of the disease.

One embodiment of the invention provides a combination of a compound of formula (I) according to any of claims 1 to 9 or a pharmaceutically acceptable salt thereof and olesoxime, for use in the treatment, prevention, delaying progression and/or amelioration of diseases caused by an inactivating mutation or deletion in the SMN1 gene and/or associated with loss or defect of SMN1 gene function, and/or for the protection of cells implicated in the pathophysiology of the disease.

One embodiment of the invention provides a method for the treatment, prevention, delaying progression and/or amelioration of diseases caused by an inactivating mutation or deletion in the SMN1 gene and/or associated with loss or defect of SMN1 gene function, and/or for the protection of cells implicated in the pathophysiology of the disease, which method comprises administering a combination of a SMN2 gene splicing modulator and a cytoprotector to a subject.

One embodiment of the invention provides a method for the treatment, prevention, delaying progression and/or amelioration of diseases caused by an inactivating mutation or deletion in the SMN1 gene and/or associated with loss or defect of SMN1 gene function, and/or for the protection of cells implicated in the pathophysiology of the disease, which method comprises administering a combination of a compound of formula (I) according to any of claims 1 to 9 or a pharmaceutically acceptable salt thereof and olesoxime to a subject.

One embodiment of the invention provides the use of a combination of a SMN2 gene splicing modulator and a cytoprotector for the treatment, prevention, delaying progression and/or amelioration of diseases caused by an inactivating mutation or deletion in the SMN1 gene and/or associated with loss or defect of SMN1 gene function, and/or for the protection of cells implicated in the pathophysiology of the disease.

One embodiment of the invention provides the use of a combination of a compound of formula (I) according to any of claims 1 to 9 or a pharmaceutically acceptable salt thereof and olesoxime for the treatment, prevention, delaying progression and/or amelioration of diseases caused by an inactivating mutation or deletion in the SMN1 gene and/or associated with loss or defect of SMN1 gene function, and/or for the protection of cells implicated in the pathophysiology of the disease.

One embodiment of the invention provides the use of a combination of a SMN2 gene splicing modulator and a cytoprotector for the preparation of medicaments for the treatment, prevention, delaying progression and/or amelioration of diseases caused by an inactivating mutation or deletion in the SMN1 gene and/or associated with loss or defect of SMN1 gene function, and/or for the protection of cells implicated in the pathophysiology of the disease.

One embodiment of the invention provides the use of a combination of a compound of formula (I) according to any of claims 1 to 9 or a pharmaceutically acceptable salt thereof and olesoxime for the preparation of medicaments for the treatment, prevention, delaying progression and/or amelioration of diseases caused by an inactivating mutation or deletion in the SMN1 gene and/or associated with loss or defect of SMN1 gene function, and/or for the protection of cells implicated in the pathophysiology of the disease.

Pharmaceutical Compositions

It has been found, that the compounds of formula (I) of present invention have a high aqueous solubility. Due to the handicaps in swallowing of all age groups of SMA patients, administration of a solution has been found to be preferred.

The compounds of formula (I) can be formulated as oral aqueous solution by dissolving the drug substance in a buffer system at pH of less than pH 4, particularly less than pH 3.8, more particularly less than pH 3.6, most particularly pH 3.4, in order to provide sufficiently high drug concentration, e.g. citric buffer system, malate buffer system, maleate buffer system, or tartrate buffer system, most particularly tartrate buffer system.

Long term stability of formulations of the compounds of formula (I) can be achieved by preparing a dry powder or granulation for constitution of an oral solution. A buffer system can be incorporated into dry formulation by the selection of organic acid and salts thereof as fine powders, e.g. tribasic sodium citrate and citric acid, disodium malate and malic acid, potassium sodium tartrate and tartaric acid, or disodium tartrate and tartaric acid, particularly potassium sodium tartrate and tartaric acid. Alternatively, the organic acid (particularly tartaric acid) can be employed alone as acidifier instead of the combination of acid and the corresponding salt.

Powders or granules comprising a compound of formula (I) may comprise a diluent, such as sorbitol, isomalt, or particularly mannitol, and combinations thereof, which ensure fast dissolution of the powder blend during constitution of the oral solution. In introduction of a filler the powder blend can be granulated by dry compaction in order to improve the flowability and to ensure robust uniformity.

Ingredients for the constitution of a solvent system for the compounds of formula (I) can be formulated as separate formulation. The constituted solvent can be used for dissolution of the compounds of formula (I) in a bottle at the start of the in-use period of the oral solution.

A particular embodiment of the invention relates to a pharmaceutical composition comprising a compound of formula (I) or a pharmaceutically acceptable salt thereof in powder form for constitution of an oral solution.

In a particular embodiment of the invention, the pharmaceutical composition comprising a compound of formula (I) or a pharmaceutically acceptable salt thereof are filled in a multidose bottle with adapter for use of oral dispensers. It has been found that such multidose bottle with adapter for use of oral dispensers enables high dosing flexibility, e.g. body weight adjusted dosing and provides safe and convenient dose administration.

In a particular embodiment of the invention, the pharmaceutical composition comprising a compound of formula (I) or a pharmaceutically acceptable salt thereof is prepared through dry granulation by roller compaction followed bottle filling. It has been found that such processing is beneficial (particularly for water soluble fillers) to prevent demixing.

A particular embodiment of the invention relates to a pharmaceutical composition comprising a compound of formula (I) or a pharmaceutically acceptable salt thereof wherein the composition is an oral aqueous solution or a dry powder suitable for constitution of an oral aqueous solution.

A particular embodiment of the invention relates to a pharmaceutical composition comprising a compound of formula (I) or a pharmaceutically acceptable salt thereof wherein the composition is an oral aqueous solution not including aerosols or a dry powder suitable for constitution of an oral aqueous solution.

In a particular embodiment of the invention, the pharmaceutical composition comprising a compound of formula (I) or a pharmaceutically acceptable salt thereof is not an aerosol.

In a particular embodiment of the invention, the pharmaceutical composition comprising a compound of formula (I) or a pharmaceutically acceptable salt thereof does not comprise a tonicifier, e.g. a salt such as sodium chloride.

A particular embodiment of the invention relates to a pharmaceutical composition comprising a compound of formula (I) or a pharmaceutically acceptable salt thereof wherein the composition is an oral aqueous solution or a dry powder suitable for constitution of an oral aqueous solution, and wherein the oral aqueous solution has a pH of less than pH4, particularly less than pH3.8, more particularly less than pH 3.6, most particularly pH 3.4.

A particular embodiment of the invention relates to a pharmaceutical composition comprising a compound of formula (I) or a pharmaceutically acceptable salt thereof and a citrate, malate, maleate or tartrate buffer system, particularly a malate or tartrate buffer system, most particularly a tartrate buffer system; or alternatively the corresponding acid of a buffer system alone as acidifier, particularly tartaric acid; wherein the composition is an oral aqueous solution or a dry powder suitable for constitution of an oral aqueous solution.

A particular embodiment of the invention relates to a pharmaceutical composition comprising a compound of formula (I) or a pharmaceutically acceptable salt thereof wherein the composition is an oral aqueous solution.

A particular embodiment of the invention relates to a pharmaceutical composition comprising a compound of formula (I) or a pharmaceutically acceptable salt thereof wherein the composition is an oral aqueous solution in a buffer system at pH of less than pH4, particularly less than pH3.8, more particularly less than pH 3.6, most particularly pH 3.4.

A particular embodiment of the invention relates to a pharmaceutical composition comprising a compound of formula (I) or a pharmaceutically acceptable salt thereof wherein the composition is an oral aqueous solution in a citrate, malate, maleate or tartrate buffer system, particularly in a malate or tartrate buffer system, most particularly in a tartrate buffer system; or alternatively the corresponding acid of a buffer system alone as acidifier, particularly tartaric acid.

A particular embodiment of the invention relates to a pharmaceutical composition comprising a compound of formula (I) or a pharmaceutically acceptable salt thereof wherein the composition is dry powder suitable for constitution of an oral aqueous solution.

A particular embodiment of the invention relates to a pharmaceutical composition comprising a compound of formula (I) or a pharmaceutically acceptable salt thereof wherein the composition is dry powder comprising a buffer system suitable for constitution of an oral aqueous solution at pH of less than pH4, particularly less than pH3.8, more particularly less than pH 3.6, most particularly pH 3.4.

A particular embodiment of the invention relates to a pharmaceutical composition comprising a compound of formula (I) or a pharmaceutically acceptable salt thereof wherein the composition is dry powder comprising citrate, malate, maleate or tartrate buffer system, particularly in a malate or tartrate buffer system, most particularly in a tartrate buffer system; or alternatively the corresponding acid of a buffer system alone as acidifier, particularly tartaric acid; suitable for constitution of an oral aqueous solution.

In one embodiment of the invention, the pharmaceutical composition comprising a compound of formula (I) or a pharmaceutically acceptable salt thereof optionally further comprises an extragranular filler, such as lactose, starch, hydrolyzed starch, maltodextrin, microcrystalline cellulose, mannitol, sorbitol, sucrose, dextrose, dibasic calcium phosphate, calcium sulfate, or combinations thereof.

In a particular embodiment of the invention, the extragranular filler is sorbitol, isomalt, mannitol, or combinations thereof, particularly mannitol, more particularly crystalline mannitol, most particularly crystalline mannitol with mean diameter of 160 m (Pearlitol® 160C).

In introduction of a diluent, the powder blend can be granulated by dry compaction in order to improve the flowability and to ensure robust uniformity.

In one embodiment of the invention, the pharmaceutical composition comprising a compound of formula (I) or a pharmaceutically acceptable salt thereof optionally further comprises a diluent, such as lactose, starch, hydrolyzed starch, maltodextrin, microcrystalline cellulose, mannitol, isomalt (E 953, (2ξ)-6-O-α-D-Glucopyranosyl-D-arabino-hexitol), sorbitol, sucrose, dextrose, dibasic calcium phosphate, calcium sulfate, or combinations thereof.

In one embodiment of the invention, the pharmaceutical composition comprising a compound of formula (I) or a pharmaceutically acceptable salt thereof optionally further comprises a diluent, such as lactose, starch, hydrolyzed starch, microcrystalline cellulose, mannitol, sorbitol, sucrose, dextrose, dibasic calcium phosphate, calcium sulfate, or combinations thereof.

In a particular embodiment of the invention, the diluent is mannitol, particularly D-mannitol suitable for direct compression such as Parteck® M100.

In a particular embodiment of the invention, the diluent is a mixture of mannitol and isomalt, particularly D-mannitol and (2ξ)-6-O-α-D-Glucopyranosyl-D-arabino-hexitol).

Isomalt as second diluent has been found by the inventors of present invention to improve the granule properties.

The constituted oral solution of the compounds of formula (I) in a buffer can provide in-use times of more than two weeks by the use of preservatives, stabilizers and antioxidants, such as vitamin A, vitamin C, vitamin E, vitamin E TPGS, retinyl palmitate, selenium, cysteine, methionine, citric acid, sodium citrate, methyl paraben, propyl paraben, disodium edetate, butyl hydroxyl toluol, riboflavin, ascorbic acid or combinations thereof.

The constituted oral solution of the compounds of formula (I) in a buffer can provide in-use times of more than two weeks by the use of preservatives, stabilizers and antioxidants, such as vitamin E TPGS, disodium edetate, butyl hydroxyl toluol, riboflavin, ascorbic acid, or combinations thereof.

In one embodiment of the invention, the pharmaceutical composition comprising a compound of formula (I) or a pharmaceutically acceptable salt thereof optionally further comprises a preservative, antioxidant and/or stabilizer, such as vitamin E TPGS (D-alpha tocopheryl polyethylene glycol 1000 succinate), disodium ethylenediaminetetraacetate (disodium edetate, $Na_2$ EDTA), butyl hydroxyl toluol, riboflavin, ascorbic acid, or combinations thereof. It has been found that a preservative, antioxidant and/or stabilizer can be beneficial for prolonged use time in multidose containers or to improve drug stability in solution over in-use period.

In a particular embodiment of the invention, the preservative is sorbic acid or sodium benzoate (E211), particularly sodium benzoate.

For pediatric formulations the amount of preservative included should be as low as possible. It has been found that compositions of the inventions with preservative concentrations as low as 1% wt are yielding stable solutions.

In a particular embodiment of the invention, the antioxidant is ascorbic acid ((5R)-[(1S)-1,2-dihydroxyethyl]-3,4-dihydroxyfuran-2(5H)-one).

In a particular embodiment of the invention, the stabilizer is disodium ethylenediaminetetraacetate (disodium edetate, $Na_2$ EDTA).

In one embodiment of the invention, the pharmaceutical composition comprising a compound of formula (I) or a pharmaceutically acceptable salt thereof optionally further comprises a lubricant. It has been found that a lubricant can be used as processing aid for roller compaction. Further a lubricant can be used for water soluble ingredients such as PEG to ensure acceptability of appearance.

In a particular embodiment of the invention, the lubricant is poly(ethylene glycol), particularly poly(ethylene glycol) with number average molecular weight Mn 6,000 (PEG 6000).

In one embodiment of the invention, the pharmaceutical composition comprising a compound of formula (I) or a pharmaceutically acceptable salt thereof optionally further comprises a sweetener and/or flavor to improve palatability.

In a particular embodiment of the invention, the flavor is strawberry flavor or vanilla flavor.

In a particular embodiment of the invention, the sweetener is sucralose (1,6-dichloro-1,6-dideoxy-β-D-fructofuranosyl-4-chloro-4-deoxy-α-D-galactopyranoside, E955) or sodium saccharin.

In a particular embodiment of the invention, the compound of formula (I) is 7-(4,7-diazaspiro[2.5]octan-7-yl)-2-(2,8-dimethylimidazo[1,2-b]pyridazin-6-yl)pyrido[1,2-a]pyrimidin-4-one.

In a particular embodiment of the invention, the pharmaceutical composition comprises:
a compound of formula (I) or a pharmaceutically acceptable salt thereof; and
a buffer system selected from citrate, malate, maleate or tartrate, particularly malate or tartrate, most particularly tartrate; or alternatively the corresponding acid of a buffer system alone as acidifier, particularly tartaric acid.

In a particular embodiment of the invention, the pharmaceutical composition comprises:
- a compound of formula (I) or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid; and
- a diluent, particularly mannitol or a mixture of mannitol and isomalt, more particularly mannitol.

In a particular embodiment of the invention, the pharmaceutical composition comprises:
- a compound of formula (I) or a pharmaceutically acceptable salt thereof; and
- a diluent, particularly mannitol or a mixture of mannitol and isomalt, more particularly mannitol.

In a particular embodiment of the invention, the pharmaceutical composition comprises:
- a compound of formula (I) or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- an antioxidant, particularly ascorbic acid; and
- a stabilizer, particularly disodium edetate.

In a particular embodiment of the invention, the pharmaceutical composition comprises:
- a compound of formula (I) or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid; and
- a stabilizer, particularly disodium edetate.

In a particular embodiment of the invention, the pharmaceutical composition comprises:
- a compound of formula (I) or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate; and
- a lubricant, particularly PEG6000.

In a particular embodiment of the invention, the pharmaceutical composition comprises:
- a compound of formula (I) or a pharmaceutically acceptable salt thereof;
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000; and
- a preservative, particularly sorbic acid or sodium benzoate, most particularly sodium benzoate.

In a particular embodiment of the invention, the pharmaceutical composition comprises:
- a compound of formula (I) or a pharmaceutically acceptable salt thereof
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000;
- a preservative, particularly sorbic acid or sodium benzoate, most particularly sodium benzoate,
- optionally a sweetener, particularly sucralose or sodium saccharin, most particularly sucralose; and
- optionally a flavor, particularly strawberry flavor or vanilla flavor.

In a particular embodiment of the invention, the pharmaceutical composition comprises:
- 1 to 10% wt of a compound of formula (I) or a pharmaceutically acceptable salt thereof;
- 5 to 15% wt of a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- 40 to 70% wt of a diluent, particularly mannitol or a mixture of mannitol and isomalt, more particularly mannitol;
- 1 to 4% wt of an antioxidant, particularly ascorbic acid;
- 0.5 to 2% wt of a stabilizer, particularly disodium edetate;
- 0.5 to 2% w of a lubricant, particularly PEG6000;
- 1 to 8% wt of a preservative, particularly sorbic acid or sodium benzoate, most particularly sodium benzoate,
- 0 to 3% wt of a sweetener, particularly sucralose or sodium saccharin, most particularly sucralose; and
- 0 to 20% wt of a flavor, particularly strawberry flavor or vanilla flavor; wherein the total amount of ingredients does not exceed 100% wt.

In a particular embodiment of the invention, the pharmaceutical composition comprises:
- 2 to 6% wt of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;
- 9 to 13% wt of a tartrate buffer system;
- 45 to 55% wt of a mannitol as first diluent and 8 to 10% wt of isomalt as second diluent;
- 1 to 3% wt of ascorbic acid as antioxidant;
- 0.5 to 2% wt of disodium edetate as stabilizer;
- 0.5 to 2% w of PEG6000 as lubricant;
- 1 to 7% wt of sodium benzoate as preservative,
- 1.5 to 2% wt of sucralose as sweetener; and
- 13 to 17% wt of strawberry flavor;
- wherein the total amount of ingredients does not exceed 100% wt.

Another embodiment of the invention relates to a kit for the preparation of pharmaceutical compositions comprising a compound of formula (I) or a pharmaceutically acceptable salt thereof, wherein the kit comprises:
- a powder blend comprising a compound of formula (I) or a pharmaceutically acceptable salt thereof, and
- water as solvent for constitution.

Another embodiment of the invention relates to a kit for the preparation of pharmaceutical compositions comprising a compound of formula (I) or a pharmaceutically acceptable salt thereof, wherein the kit comprises:
- a compound of formula (I) or a pharmaceutically acceptable salt thereof,
- a powder blend as vehicle for constitution, and
- optionally water as solvent for constitution.

Another embodiment relates to a power blend as vehicle suitable for constitution of a compound of formula (I) as described herein or a pharmaceutically acceptable salt thereof, comprising:
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid; and
- a diluent, particularly mannitol or a mixture of mannitol and isomalt, more particularly mannitol.

Another embodiment relates to a power blend as vehicle suitable for constitution of a compound of formula (I) as described herein or a pharmaceutically acceptable salt thereof, comprising:
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000; and
- a preservative, particularly sorbic acid or sodium benzoate, most particularly sodium benzoate.

Another embodiment relates to a power blend as vehicle suitable for constitution of a compound of formula (I) as described herein or a pharmaceutically acceptable salt thereof, comprising:
- a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- a diluent, particularly mannitol or a mixture of mannitol and isomalt, more particularly mannitol;
- an antioxidant, particularly ascorbic acid;
- a stabilizer, particularly disodium edetate;
- a lubricant, particularly PEG6000;
- a preservative, particularly sorbic acid or sodium benzoate, most particularly sodium benzoate,
- optionally a sweetener, particularly sucralose or sodium saccharin, most particularly sucralose; and
- optionally a flavor, particularly strawberry flavor or vanilla flavor.

Another embodiment relates to a power blend as vehicle suitable for constitution of a compound of formula (I) as described herein or a pharmaceutically acceptable salt thereof, comprising:
- 4 to 15% wt of a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
- 40 to 70% wt of a diluent, particularly mannitol or a mixture of mannitol and isomalt, more particularly mannitol;
- 1 to 4% wt of an antioxidant, particularly ascorbic acid;
- 0.2 to 2% wt of a stabilizer, particularly disodium edetate;
- 0.5 to 2% w of a lubricant, particularly PEG6000;
- 1 to 8% wt of a preservative, particularly sorbic acid or sodium benzoate, most particularly sodium benzoate,
- 0 to 3% wt of a sweetener, particularly sucralose or sodium saccharin, most particularly sucralose; and
- 0 to 20% wt of a flavor, particularly strawberry flavor or vanilla flavor; wherein the total amount of ingredients does not exceed 100% wt.

Another embodiment relates to a power blend as vehicle suitable for constitution of a compound of formula (I) as described herein or a pharmaceutically acceptable salt thereof, comprising:
- 9 to 13% wt of a tartrate buffer system or tartaric acid;
- 45 to 55% wt of a mannitol as first diluent and 8 to 10% wt of isomalt as second diluent;
- 1 to 3% wt of ascorbic acid as antioxidant;
- 0.3 to 0.9% wt of disodium edetate as stabilizer;
- 0.5 to 2% w of PEG6000 as lubricant;
- 3 to 7% wt of sodium benzoate as preservative,
- 0.8 to 2.0% wt of sucralose as sweetener; and
- 7.5 to 19% wt of strawberry flavor;
wherein the total amount of ingredients does not exceed 100% wt.

A particular embodiment of the invention relates to a pharmaceutical composition comprising a compound of formula (I) or a pharmaceutically acceptable salt thereof as described herein and further olesoxime.

In a particular embodiment of the invention olesoxime has a particle size distribution with d90 value smaller 200 μm, particularly d90 value smaller 100 μm, more particularly d90 value of 50-100 μm.

The term "d90 value" denotes the diameter where 90 wt % of the particles of the ensemble have a smaller equivalent spherical diameter than the value.

A particular embodiment of the invention relates to a pharmaceutical composition comprising a compound of formula (I) or a pharmaceutically acceptable salt thereof as described herein, olesoxime and an oil selected from sesame oil, olive oil, soya oil, cotton oil, castor oril, nut oil, rapeseed oil, corn oil, almond oil, sunflower oil, and combinations thereof.

A particular embodiment of the invention relates to a pharmaceutical composition comprising a compound of formula (I) or a pharmaceutically acceptable salt thereof as described herein; olesoxime; an oil selected from sesame oil, olive oil, soya oil, cotton oil, castor oril, nut oil, rapeseed oil, corn oil, almond oil, sunflower oil, and combinations thereof; an emulsifying and/or lipophilic solubilizing agents selected from glyceryl mono-oleate (Peceol™, Inwitor 948™ Capmul GMO™), glyceryl mono-linoleate (Maisine 35-1™), sorbitan mono-oleate (Span 80™), oleic acid, and combinations thereof; and optionally a polar surfactant, particularly a surfactant with a HLB value of less than 7, more particularly polysorbate 80 (Tween 80™) caprylocaproyl polyoxyl glycerides (Labrasol™), and combinations thereof.

In a particular embodiment of the invention, the pharmaceutical composition comprises:

a compound of formula (I) or a pharmaceutically acceptable salt thereof;
a buffer system selected from citrate, malate, maleate or tartrate, particularly malate or tartrate, most particularly tartrate; or alternatively the corresponding acid of a buffer system alone as acidifier, particularly tartaric acid;
olesoxime;
an oil, particularly sesame oil, olive oil, soya oil, cotton oil, castor oril, nut oil, rapeseed oil, corn oil, almond oil, sunflower oil, or combinations thereof, most particularly sesame oil;
an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof; and
optionally a polar surfactant, particularly a surfactant with a HLB value of less than 7, more particularly polysorbate 80 (Tween 80™), caprylocaproyl polyoxyl glycerides (Labrasol™), or combinations thereof.

In a particular embodiment of the invention, the pharmaceutical composition comprises:
a compound of formula (I) or a pharmaceutically acceptable salt thereof
a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
a diluent, particularly mannitol or a mixture of mannitol and isomalt, more particularly mannitol;
olesoxime;
an oil, particularly sesame oil, olive oil, soya oil, cotton oil, castor oril, nut oil, rapeseed oil, corn oil, almond oil, sunflower oil, or combinations thereof, most particularly sesame oil;
an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof; and
optionally a polar surfactant, particularly a surfactant with a HLB value of less than 7, more particularly polysorbate 80 (Tween 80™), caprylocaproyl polyoxyl glycerides (Labrasol™), or combinations thereof.

In a particular embodiment of the invention, the pharmaceutical composition comprises:
a compound of formula (I) or a pharmaceutically acceptable salt thereof;
a diluent, particularly mannitol or a mixture of mannitol and isomalt, more particularly mannitol;
olesoxime;
an oil, particularly sesame oil, olive oil, soya oil, cotton oil, castor oril, nut oil, rapeseed oil, corn oil, almond oil, sunflower oil, or combinations thereof, most particularly sesame oil;
an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof; and
optionally a polar surfactant, particularly a surfactant with a HLB value of less than 7, more particularly polysorbate 80 (Tween 80™), caprylocaproyl polyoxyl glycerides (Labrasol™), or combinations thereof.

In a particular embodiment of the invention, the pharmaceutical composition comprises:
a compound of formula (I) or a pharmaceutically acceptable salt thereof;
a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
an antioxidant, particularly ascorbic acid;
a stabilizer, particularly disodium edetate;
olesoxime,
an oil, particularly sesame oil, olive oil, soya oil, cotton oil, castor oril, nut oil, rapeseed oil, corn oil, almond oil, sunflower oil, or combinations thereof, most particularly sesame oil;
an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof; and
optionally a polar surfactant, particularly a surfactant with a HLB value of less than 7, more particularly polysorbate 80 (Tween 80™), caprylocaproyl polyoxyl glycerides (Labrasol™), or combinations thereof.

In a particular embodiment of the invention, the pharmaceutical composition comprises:
a compound of formula (I) or a pharmaceutically acceptable salt thereof;
a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
a diluent, particularly mannitol or a mixture of mannitol and isomalt, more particularly mannitol;
an antioxidant, particularly ascorbic acid;
a stabilizer, particularly disodium edetate;
olesoxime;
an oil, particularly sesame oil, olive oil, soya oil, cotton oil, castor oril, nut oil, rapeseed oil, corn oil, almond oil, sunflower oil, or combinations thereof, most particularly sesame oil;
an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof; and
optionally a polar surfactant, particularly a surfactant with a HLB value of less than 7, more particularly polysorbate 80 (Tween 80™), caprylocaproyl polyoxyl glycerides (Labrasol™), or combinations thereof.

In a particular embodiment of the invention, the pharmaceutical composition comprises:
a compound of formula (I) or a pharmaceutically acceptable salt thereof;
a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;
a diluent, particularly mannitol or a mixture of mannitol and isomalt, more particularly mannitol;
an antioxidant, particularly ascorbic acid;
a stabilizer, particularly disodium edetate;
a lubricant, particularly PEG6000;
olesoxime;

an oil, particularly sesame oil, olive oil, soya oil, cotton oil, castor oil, nut oil, rapeseed oil, corn oil, almond oil, sunflower oil, or combinations thereof, most particularly sesame oil;

an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof; and optionally a polar surfactant, particularly a surfactant with a HLB value of less than 7, more particularly polysorbate 80 (Tween 80™), caprylocaproyl polyoxyl glycerides (Labrasol™), or combinations thereof.

In a particular embodiment of the invention, the pharmaceutical composition comprises:

a compound of formula (I) or a pharmaceutically acceptable salt thereof;

a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;

a diluent, particularly mannitol or a mixture of mannitol and isomalt, more particularly mannitol;

an antioxidant, particularly ascorbic acid;

a stabilizer, particularly disodium edetate;

a lubricant, particularly PEG6000;

a preservative, particularly sorbic acid or sodium benzoate, most particularly sodium benzoate;

olesoxime;

an oil, particularly sesame oil, olive oil, soya oil, cotton oil, castor oril, nut oil, rapeseed oil, corn oil, almond oil, sunflower oil, or combinations thereof, most particularly sesame oil;

an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof; and optionally a polar surfactant, particularly a surfactant with a HLB value of less than 7, more particularly polysorbate 80 (Tween 80™), caprylocaproyl polyoxyl glycerides (Labrasol™), or combinations thereof.

In a particular embodiment of the invention, the pharmaceutical composition comprises:

a compound of formula (I) or a pharmaceutically acceptable salt thereof;

a buffer system, particularly a buffer system selected from citrate, malate, maleate or tartrate, more particularly malate or tartrate, most particularly tartrate; or alternatively the corresponding acid of a buffer system alone as acidifier, particularly tartaric acid;

a diluent, particularly mannitol or a mixture of mannitol and isomalt, more particularly mannitol;

an antioxidant, particularly ascorbic acid;

a stabilizer, particularly disodium edetate;

a lubricant, particularly PEG6000;

a preservative, particularly sorbic acid or sodium benzoate, most particularly sodium benzoate;

optionally a sweetener, particularly sucralose or sodium saccharin, most particularly sucralose;

optionally a flavor, particularly strawberry flavor or vanilla flavor;

olesoxime;

an oil, particularly sesame oil, olive oil, soya oil, cotton oil, castor oril, nut oil, rapeseed oil, corn oil, almond oil, sunflower oil, or combinations thereof, most particularly sesame oil;

an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof; and optionally a polar surfactant, particularly a surfactant with a HLB value of less than 7, more particularly polysorbate 80 (Tween 80™), caprylocaproyl polyoxyl glycerides (Labrasol™), or combinations thereof.

Another embodiment of the invention relates to a kit for the preparation of pharmaceutical compositions comprising a compound of formula (I) or a pharmaceutically acceptable salt thereof and olexosime, wherein the kit comprises:

a powder blend comprising a compound of formula (I) or a pharmaceutically acceptable salt thereof;

water as solvent for constitution;

olesoxime;

an oil, particularly sesame oil, olive oil, soya oil, cotton oil, castor oril, nut oil, rapeseed oil, corn oil, almond oil, sunflower oil, or combinations thereof, most particularly sesame oil;

an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof, and optionally a polar surfactant, particularly a surfactant with a HLB value of less than 7, more particularly polysorbate 80 (Tween 80™), caprylocaproyl polyoxyl glycerides (Labrasol™), or combinations thereof.

Another embodiment of the invention relates to a kit for the preparation of pharmaceutical compositions comprising a compound of formula (I) or a pharmaceutically acceptable salt thereof and olesoxime, wherein the kit comprises:

a compound of formula (I) or a pharmaceutically acceptable salt thereof, a powder blend as vehicle for constitution;

optionally water as solvent for constitution;

olesoxime;

an oil, particularly sesame oil, olive oil, soya oil, cotton oil, castor oril, nut oil, rapeseed oil, corn oil, almond oil, sunflower oil, or combinations thereof, most particularly sesame oil;

an emulsifying and/or lipophilic solubilizing agents, particularly glyceryl mono-oleate (Peceol™, Inwitor 948™, Capmul GMO™), glyceryl mono-linoleate (Maisine 35-1™), sorbitan mono-oleate (Span 80™), oleic acid, or combinations thereof, and optionally a polar surfactant, particularly a surfactant with a HLB value of less than 7, more particularly polysorbate 80 (Tween 80™), caprylocaproyl polyoxyl glycerides (Labrasol™), or combinations thereof.

FIGURES

FIG. 1. 7-(4,7-diazaspiro[2.5]octan-7-yl)-2-(2,8-dimethylimidazo[1,2-b]pyridazin-6-yl)pyrido[1,2-a]pyrimidin-4-one (Example 20) increases SMN mRNA and protein production in vitro.

(A) SMN2 splicing in SMA Type 1 fibroblasts. (B) SMN protein in SMA Type 1 fibroblasts. (C) SMN protein in SMA Type 1 motor neurons. (D) SMN1 and SMN2 splicing in whole blood derived from HV. Fibroblasts from SMA Type 1 patients were cultured for 24 hours (A) or 48 hours (B); motor neurons from SMA Type 1 patient iPSCs (induced Pluripotent Stem Cells) were cultured for 72 hours (C) and whole blood cells from healthy volunteers (HV) for 4 hours (D) in the presence of the compound of Example 20. SMN splicing was assessed by RT-PCR, and SMN protein levels were assessed by homogenous time-resolved fluorescence (HTRF) in fibroblast lysates, and by immunostaining for SMN in motor neurons. Data represent means standard error (SEM) of 3 evaluations per data point and are expressed as fold change vs. untreated controls.

Figure 2:
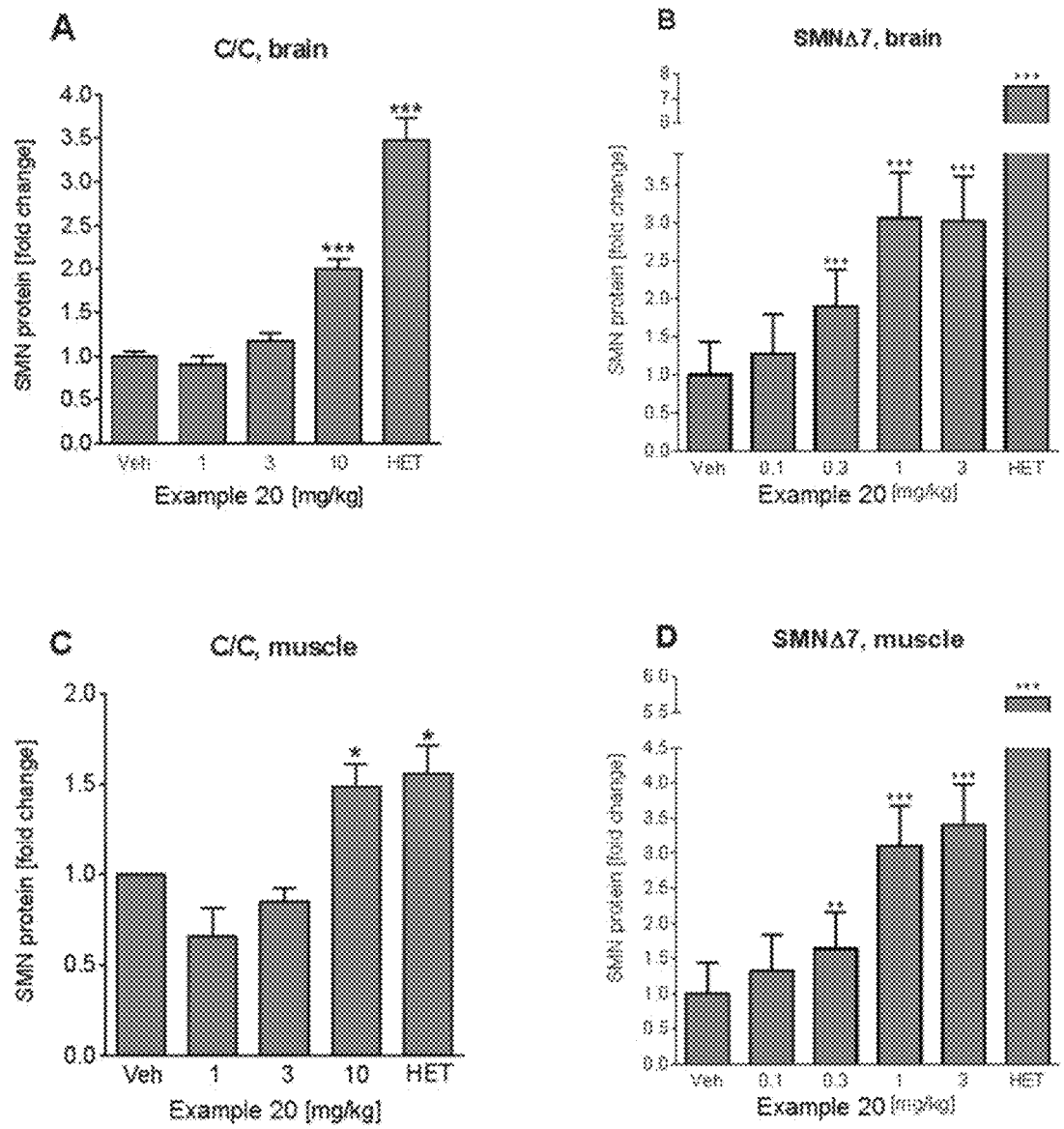

FIG. 2. 7-(4,7-diazaspiro[2.5]octan-7-yl)-2-(2,8-dimethylimidazo[1,2-b]pyridazin-6-yl)pyrido[1,2-a]pyrimidin-4-one (Example 20) induces SMN Protein Expression in vivo. (A) SMN protein in brains of C/C-allele mice. (B) SMN protein in brains of SMNΔ7 mice. (C) SMN protein in quadriceps muscle of C/C-allele mice. (D) SMN protein in quadriceps muscle of SMNΔ7 mice. C/C-allele mice and SMNΔ7 mice were treated with the compound of Example 20. One hour after the last dose, brains and quadriceps muscles were collected and levels of SMN protein were assessed by HTRF. Data represent means SEM of 5-6 animals per group and are expressed as fold change vs. vehicle-treated controls. *=p<0.05, =p<0.01, *=p<0.001 vs. untreated controls.

Figure 3:
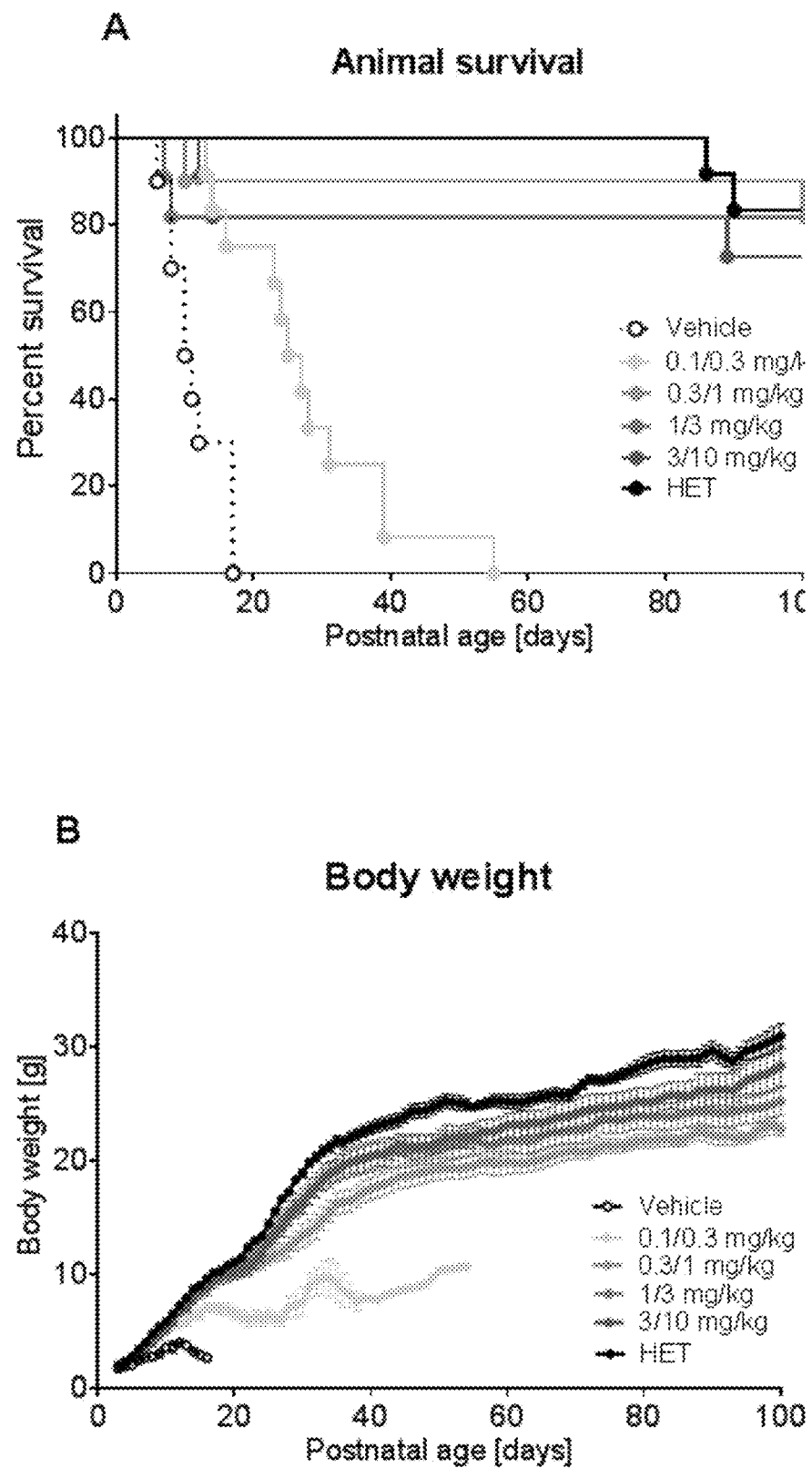

FIG. 3. in vivo Effects of treatment SMNΔ7 mice with 7-(4,7-diazaspiro[2.5]octan-7-yl)-2-(2,8-dimethylimidazo[1,2-b]pyridazin-6-yl)pyrido[1,2-a]pyrimidin-4-one (Example 20). SMNΔ7 mice were treated with the compound of Example 20 from P3 onwards and animal survival (A) and body weight (B) were assessed daily until P100. Data represent means SEM of 10-12 mice per group. HET=heterozygous littermates.

Figure 4:
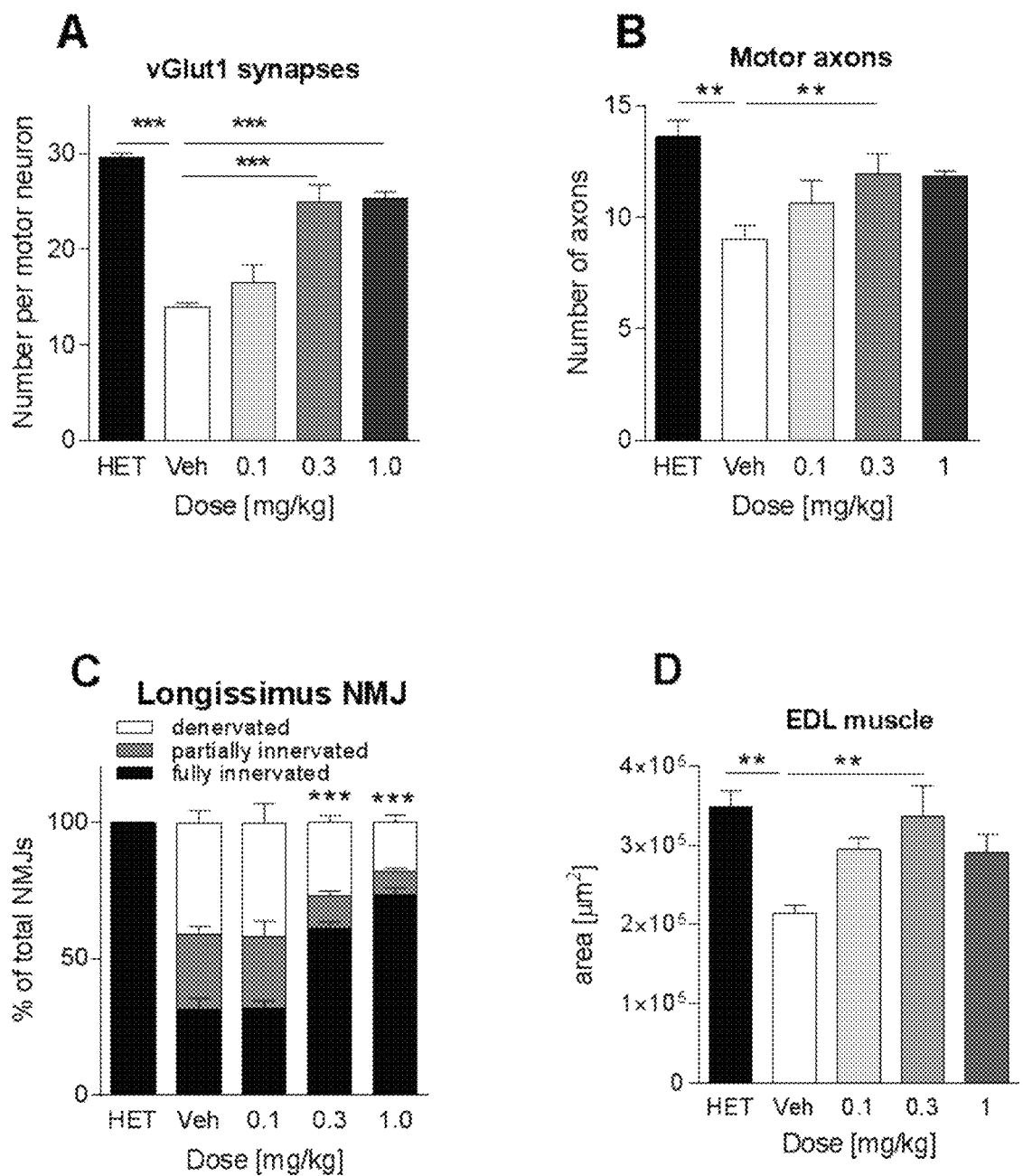

FIG. 4. Protection of Motor Circuits and Muscle Atrophy by 7-(4,7-diazaspiro[2.5]octan-7-yl)-2-(2,8-dimethylimidazo[1,2-b]pyridazin-6-yl)pyrido[1,2-a]pyrimidin-4-one (Example 20) in SMNΔ7 mice in vivo. SMNΔ7 mice were treated with the compound of Example 20 from P3 to P14, and neuromuscular connectivity and muscle atrophy were assessed by immunohistochemistry. (A) vGlut1-positive proprioceptive inputs in L3-5 spinal cord. (B) Ventral motor axons in L3-5 spinal cord. (C) NMJ innervation onto longissimus muscle. (D) EDL muscle cross-sectional area. Data represent means SEM of 4-5 mice per group. *=p<0.05; =p<0.01; *=p<0.001 vs. vehicle-treated SMNΔ7 mice.

Figure 5:
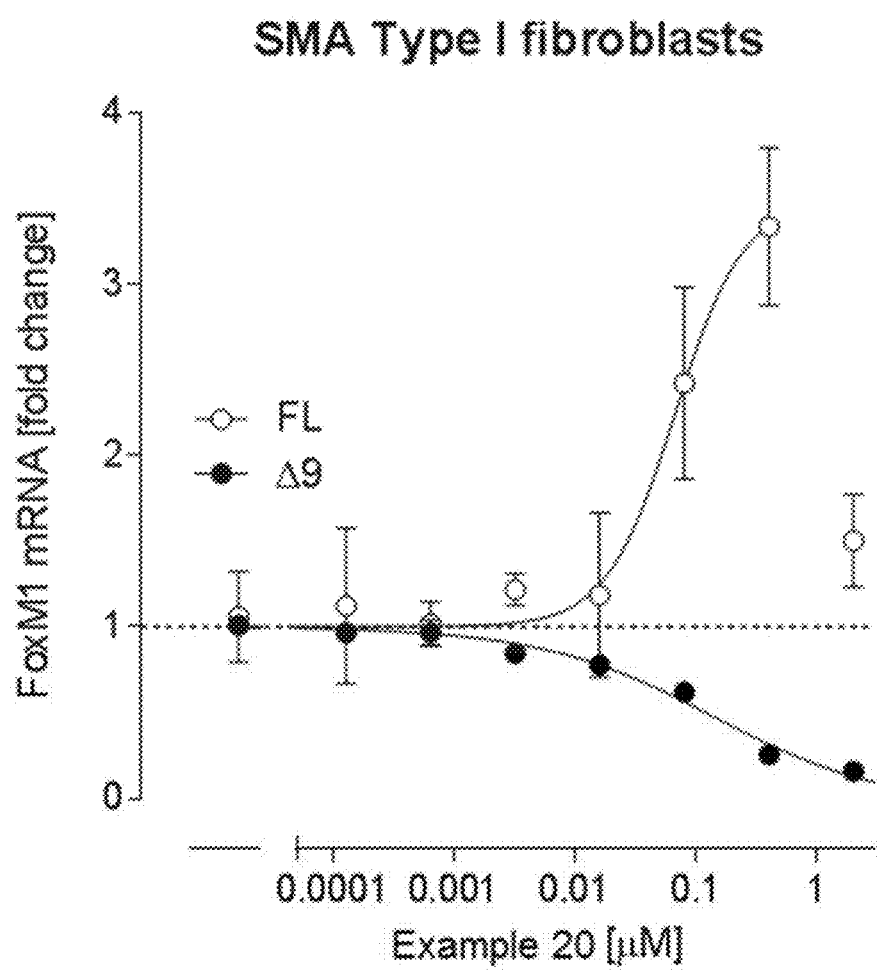

FIG. 5. Alternative Splicing of FoxM1 in vitro SMA Type I patient fibroblasts were treated with the compound of Example 20 for 24 hours, and FoxM1 full-length (FL) and exon 9-lacking (Δ9) mRNAs were analyzed by RT-qPCR. Data represent means SEM of 6 repetitions and are expressed as fold change vs. untreated controls.

Figure 6:
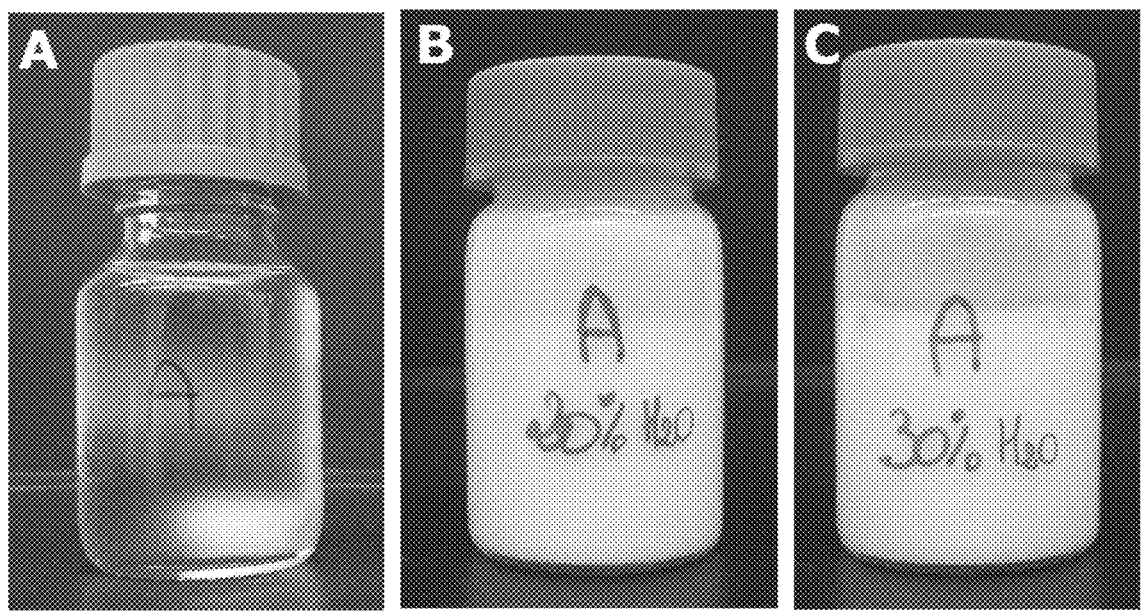

FIG. 6. Oil-in-water emulsions Photographs of composition 4A prior to (A) and immediately after the addition of 20% (B) or 30% (C) of tartrate buffer solution (composition 5A) and thereby resulting water-in-oil emulsions.

Figure 7:
Figure 7:
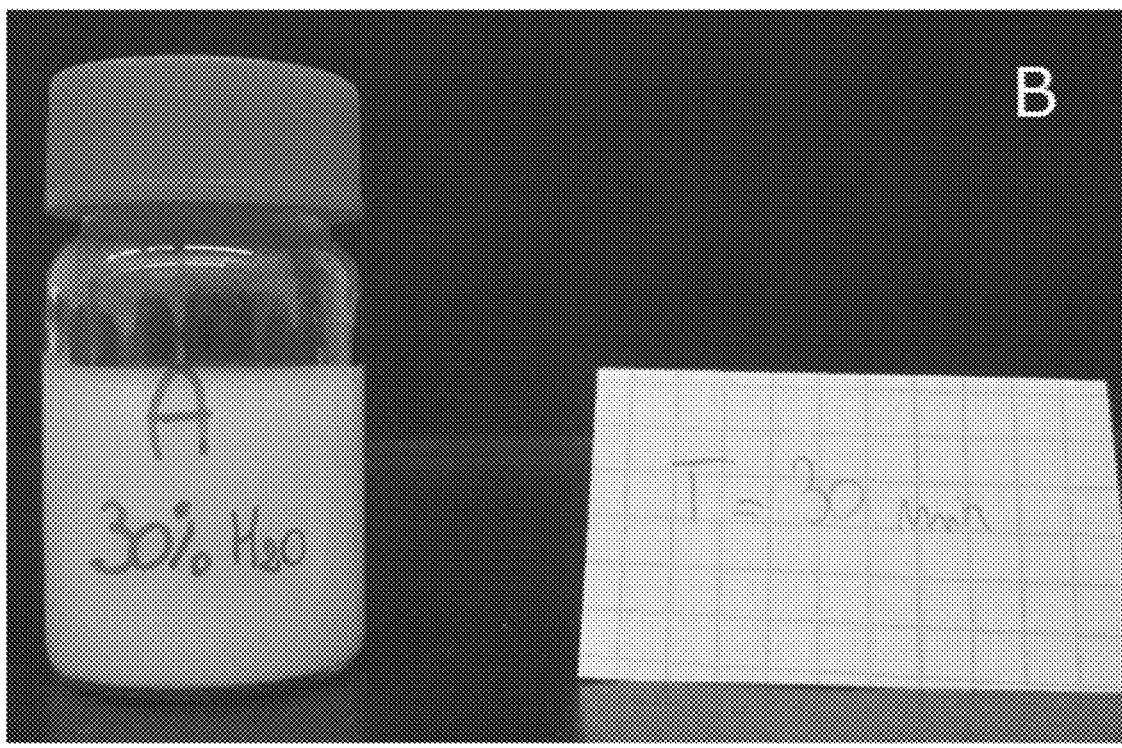

FIG. 7. Stability of Oil-in-water emulsions Photographs of water-in-oil emulsions comprising 70% composition 4A and 30% composition 5A 15 minutes after constitution (A) (10 times shaking) and 30 min after constitution (B) (10 times shaking).

Figure 8:
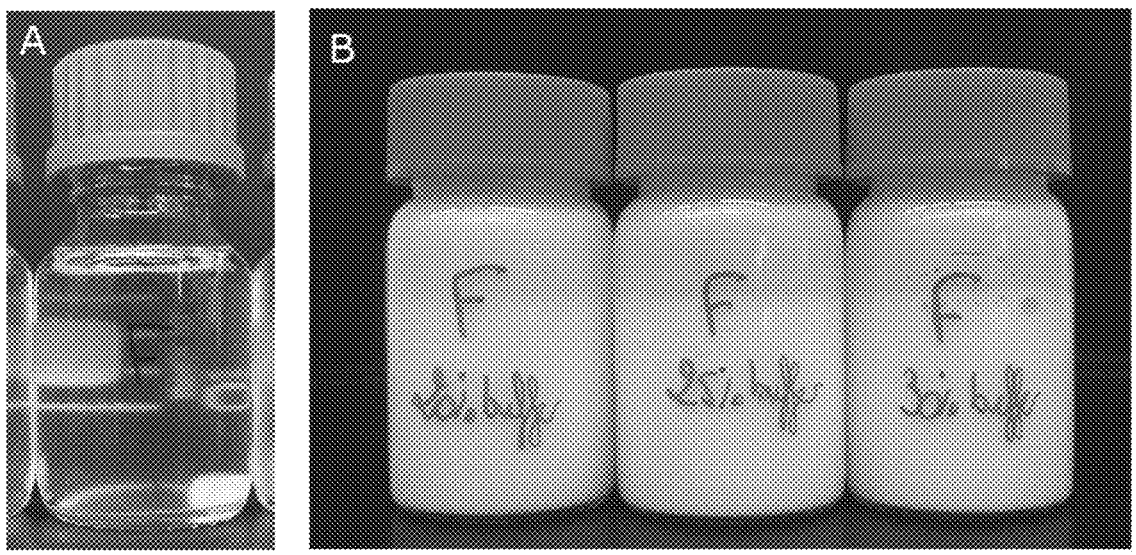

FIG. 8. Oil-in-water emulsions Photographs of composition 4F prior to (A) and immediately after the addition of 20% (B left), 25% (B middle) or 30% (B right) of tartrate buffer solution (composition 5A) and thereby resulting water-in-oil emulsions.

Figure 9:
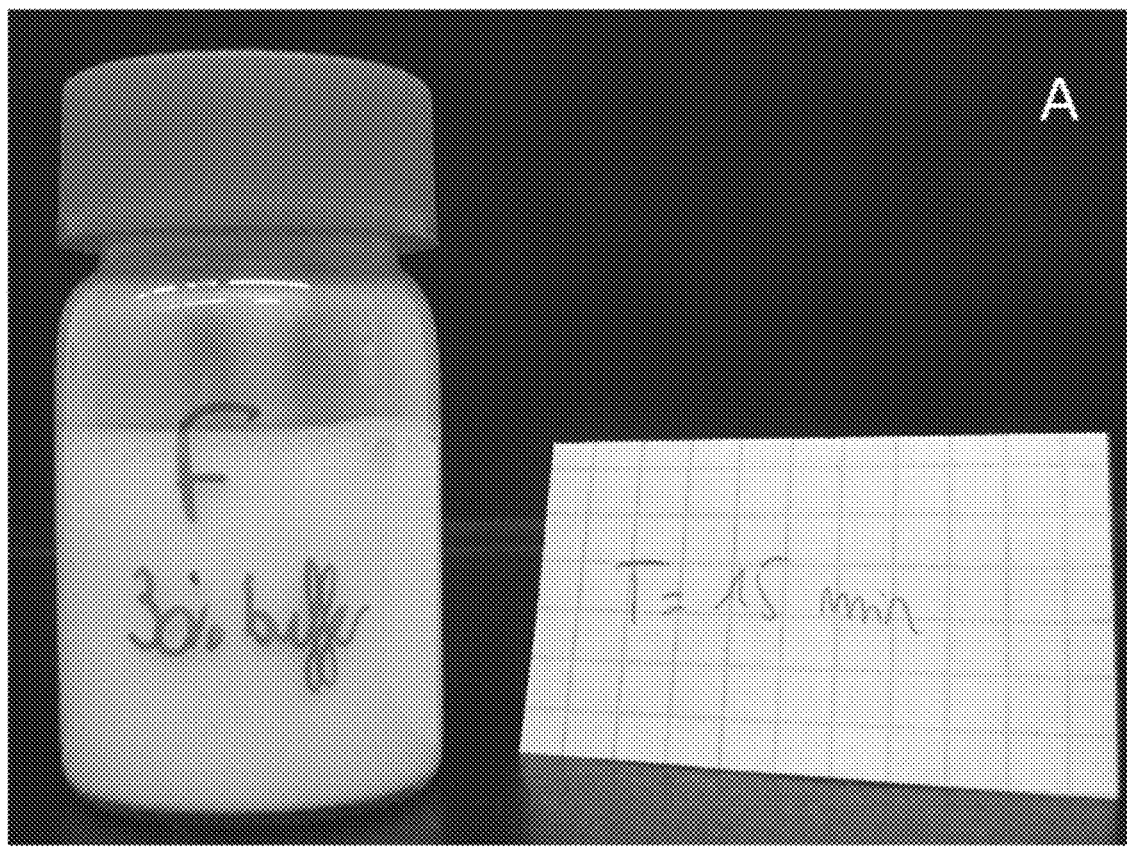
Figure 9:

FIG. 9. Stability of Oil-in-water emulsions Photographs of water-in-oil emulsions comprising 70% composition 4F and 30% composition 5A 15 minutes after constitution (A) (10 times shaking) and 30 min after constitution (B) (10 times shaking).

EXAMPLES

The invention will be more fully understood by reference to the following examples. They should however not be construed as limiting the scope of the invention.

Abbreviations Used

ACN: Acetonitrile; $CH_2Cl_2$: dichloromethane (DCM); DIPEA: diisopropyl ethylamine; DMA: dimethyl acetamide; TEA: triethylamine; RT: room temperature; $B_2(pin)_2$: bis(pinacolato)diboron; $Pd(dppf)Cl_2$: (1,1'-Bis(diphenylphosphino)ferrocene)palladium(II) dichloride; PPTS: Pyridinium p-toluenesulfonate.

Intermediate 1

7-fluoro-2-(2-methylimidazo[1,2-b]pyridazin-6-yl)pyrido[1,2-a]pyrimidin-4-one a) 2-chloro-7-fluoro-pyrido[1,2-a]pyrimidin-4-one

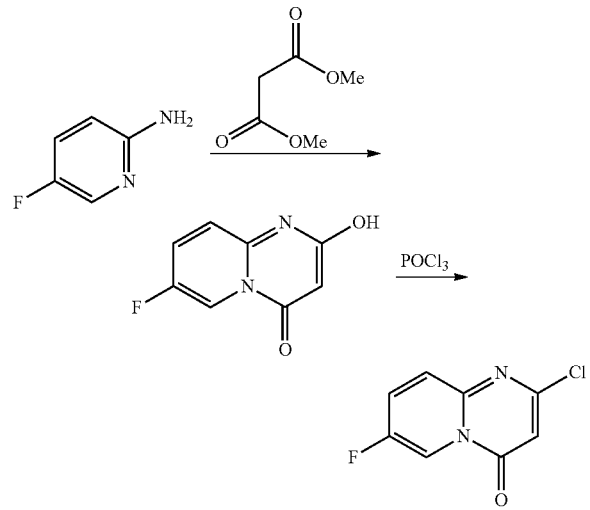

A mixture of 2-amino-5-fluoropyridine (11.20 g, 0.10 mol) and dimethyl malonate (57.0 mL, 0.50 mol) was heated at 230° C. for 1.5 h. After cooling to room temperature, the precipitate was filtered and washed with ACN (3×) to give 7-fluoro-2-hydroxy-4H-pyrido[1,2-a]pyrimidin-4-one as a dark solid (14 g), which was used directly in the next step. MS m/z 181.3 [M+H]+.

A dark mixture of crude 7-fluoro-2-hydroxy-4H-pyrido[1,2-a]pyrimidin-4-one (14 g, ~77 mmol) in $POCl_3$ (50 mL) and DIPEA (13.3 mL, 77 mmol) was heated at 110° C. for 15 hours. The solvent was removed and the dark residue was treated with ice-water, washed with water (3×) and dried to give a brown solid. The crude brown solid was chromatographed (5% MeOH in $CH_2Cl_2$) to give 2-chloro-7-fluoro-4H-pyrido[1,2-a]pyrimidin-4-one as a yellow solid (9.84 g, 50%, 2 steps), MS m/z 199.2 [M+H]+.

b) 2-methyl-6-(4,4,5,5-tetramethyl-1,3,2-dioxaborolan-2-yl)imidazo[1,2-b]pyridazine

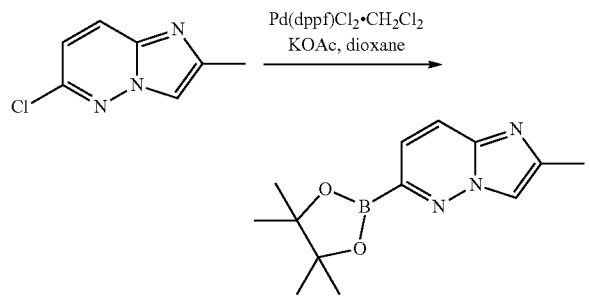

A mixture of 6-chloro-2-methylimidazo[1,2-b]pyridazine (900 mg, 5.37 mmol), 4,4,4',4',5,5,5',5'-octamethyl-2,2'-bi(1,3,2-dioxaborolane) (1.36 g, 5.37 mmol, 1.0 eq.), KOAc (1.05 g, 10.7 mmol) and Pd(dppf)Cl₂CH₂Cl₂ (393 mg, 0.54 mmol) in dioxane (50 mL) was degassed and heated under N₂ at 95° C. After 15 hours, the mixture was diluted with EtOAc, filtered through celite and concentrated under vacuum to give 2-methyl-6-(4,4,5,5-tetramethyl-1,3,2-dioxaborolan-2-yl)imidazo[1,2-b]pyridazine which was used directly in the next step.

c) 7-fluoro-2-(2-methylimidazo[1,2-b]pyridazin-6-yl)pyrido[1,2-a]pyrimidin-4-one

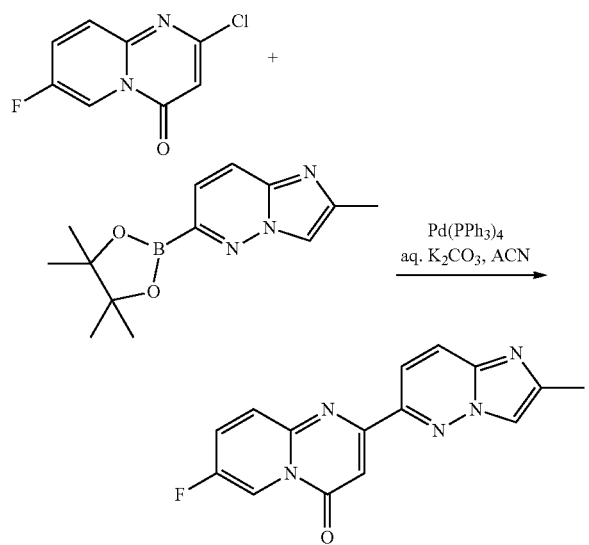

To a solution of 2-chloro-7-fluoro-4H-pyrido[1,2-a]pyrimidin-4-one (750 mg, 3.78 mmol) in ACN (36 m) was added 2-methyl-6-(4,4,5,5-tetramethyl-1,3,2-dioxaborolan-2-yl)imidazo[1,2-b]pyridazine (1.17 g, 4.53 mmol, Eq: 1.2), Pd(Ph₃P)₄ (218 mg, 0.189 mmol, 0.05 eq.) and an aqueous solution of K₂CO₃ (3.78 mL, 7.55 mmol, 2.0 eq.). The mixture was degassed and heated under argon at 105° C. overnight. The reaction was cooled to RT, and filtered. The precipitate was washed with Et₂O and then water, dried in vacuo to give 250 mg (22%) of 7-fluoro-2-(2-methylimidazo[1,2-b]pyridazin-6-yl)pyrido[1,2-a]pyrimidin-4-one as a light brown solid. MS m/z 296.1 [M+H]⁺.

Intermediate 2

2-(2,8-dimethylimidazo[1,2-b]pyridazin-6-yl)-7-fluoro-pyrido[1,2-a]pyrimidin-4-one a) 2,8-dimethyl-6-(4,4,5,5-tetramethyl-1,3,2-dioxaborolan-2-yl)imidazo[1,2-b]pyridazine

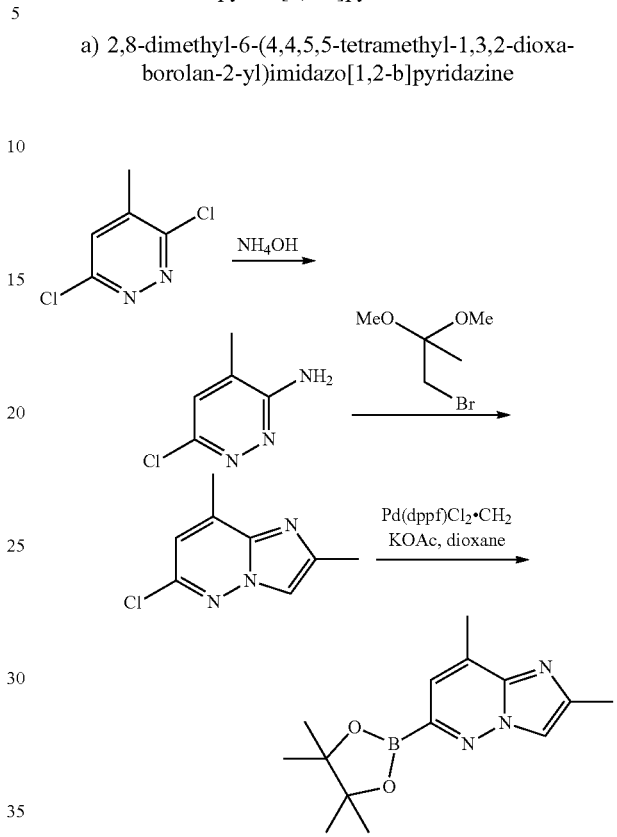

In a sealed flask, 3,6-dichloro-4-methylpyridazine (27 g, 161 mmol) was suspended in aqueous ammonia (25%, 300 mL). The reaction mixture was heated at 110° C. for 48 hours (turned into solution after 1 hour). After cooling to room temperature, the reaction was poured into CH₂Cl₂, and the organic phase was separated, dried over Na₂SO₄, and concentrated under vacuum, to give 22.4 g of 6-chloro-4-methyl-pyridazin-3-amine and 6-chloro-5-methyl-pyridazin-3-amine as a mixture of regioisomers which were used directly in the next step.

The mixture of regioisomers 6-chloro-4-methyl-pyridazin-3-amine and 6-chloro-5-methyl-pyridazin-3-amine (22.4 g) was suspended in 2-propanol (300 mL). 1-bromo-2,2-dimethoxypropane (36.0 g, 26.6 mL, 193 mmol, 1.2 eq.) and PPTS (2.96 g, 11.6 mmol, 0.0725 eq.) were added, and the resulting solution was heated at 105° C. overnight. The solvent was removed in vacuo and the residue was taken up in CH₂Cl₁₂ and washed with NaHCO₃. The organic phases were dried over Na₂SO₄, concentrated in vacuo and the crude light brown solid was chromatographed (EtOAc/Heptane 1/2-1/1) to give separately 6.1 g of 6-chloro-2,8-dimethyl-imidazo[1,2-b]pyridazine MS m/z 182.1 [M+H]⁺(21%) as a white solid and 5.9 g of 6-chloro-2,7-dimethyl-imidazo[1,2-b]pyridazine MS m/z 182.1 [M+H]⁺(20%) as a white solid.

A mixture of 6-chloro-2,8-dimethylimidazo[1,2-b]pyridazine (0.9 g, 4.96 mmol), 4,4,4',4',5,5,5',5'-octamethyl-2,2'-bi(1,3,2-dioxaborolane) (1.26 g, 4.96 mmol, 1.0 eq.), KOAc (0.97 g, 9.91 mmol) and Pd(dppf)Cl₂•CH₂Cl₂ (363 mg, 0.49 mmol) in dioxane (50 mL) was degassed and heated under N₂ at 110° C. After 15 hours, the mixture was diluted with EtOAc, filtered through celite and concentrated under vacuum to give 2,8-dimethyl-6-(4,4,5,5-tetramethyl-1,3,2-dioxaborolan-2-yl)imidazo[1,2-b]pyridazine which was used directly in the next step.

b) 2-(2,8-dimethylimidazo[1,2-b]pyridazin-6-yl)-7-fluoro-pyrido[1,2-a]pyrimidin-4-one

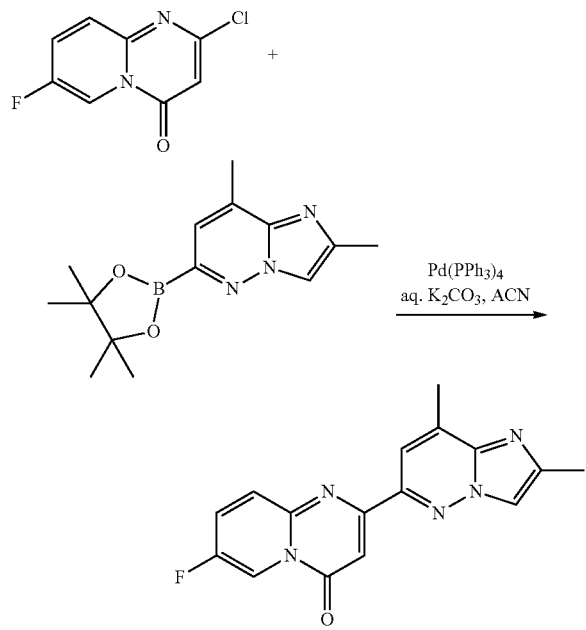

To a solution of 2-chloro-7-fluoro-4H-pyrido[1,2-a]pyrimidin-4-one (750 mg, 3.78 mmol, described herein above) in ACN (36 mL) was added 2,8-dimethyl-6-(4,4,5,5-tetramethyl-1,3,2-dioxaborolan-2-yl)imidazo[1,2-b]pyridazine (1.24 g, 4.53 mmol, 1.2 eq.), Pd(Ph₃P)₄ (218 mg, 0.189 mmol, 0.05 eq.) and an aqueous solution of K₂CO₃ (3.78 mL, 7.55 mmol, 2.0 eq.). The mixture was degassed and heated under argon at 100° C. for 6 hours. The reaction was cooled to RT, and filtered. The precipitate was washed with Et₂O and then water, dried in vacuo to give 700 mg (60%) of 2-(2,8-dimethylimidazo[1,2-b]pyridazin-6-yl)-7-fluoro-pyrido[1,2-a]pyrimidin-4-one as a light brown solid. MS m/z 310.1 [M+H]⁺.

Intermediate 3

7-fluoro-9-methyl-2-(2-methylimidazo[1,2-b]pyridazin-6-yl)pyrido[1,2-a]pyrimidin-4-one a) 2-chloro-7-fluoro-9-methyl-pyrido[1,2-a]pyrimidin-4-one

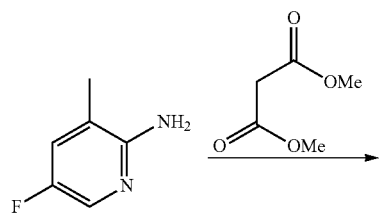

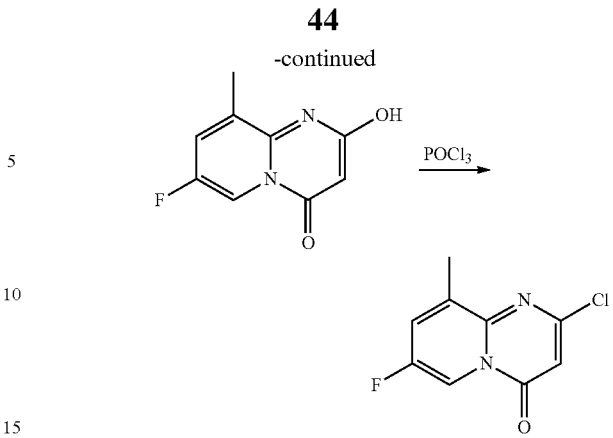

A mixture of 5-fluoro-3-methylpyridin-2-amine (3.3 g, 26.2 mmol) and dimethyl malonate (15.0 mL, 0.13 mol, 5.0 eq.) was heated at 210° C. for 1.5 hours. After cooling to room temperature, the precipitate was filtered and washed with ACN (3×) to give 7-fluoro-2-hydroxy-9-methyl-pyrido[1,2-a]pyrimidin-4-one as a dark solid (2.3 g), which was used directly in the next step. MS m/z 195.1 [M+H]⁺.

A mixture of crude 7-fluoro-2-hydroxy-9-methyl-pyrido[1,2-a]pyrimidin-4-one (2.3 g, 11.8 mmol) in POCl₃ (7.7 mL, 82.9 mmol) and DIEA (2.07 mL, 11.8 mmol) was heated at 110° C. for 15 hours. The solvent was removed and the residue was treated with ice-water, washed with water (3×) and dried to give a brown solid. The crude brown solid was chromatographed (5% MeOH in CH₂Cl₂) to give 2-chloro-7-fluoro-9-methyl-pyrido[1,2-a]pyrimidin-4-one as a yellow solid (1.77 g, 70% over 2 steps), MS m/z 213.1 [M+H]⁺.

b) 7-fluoro-9-methyl-2-(2-methylimidazo[1,2-b]pyridazin-6-yl)pyrido[1,2-a]pyrimidin-4-one

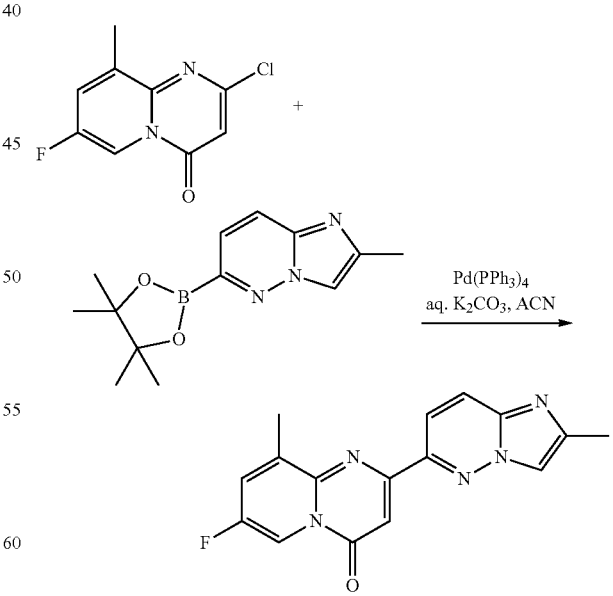

To a solution of 2-chloro-7-fluoro-9-methyl-4H-pyrido[1,2-a]pyrimidin-4-one (2.2 g, 10.3 mmol) in ACN (80 mL) was added 2-methyl-6-(4,4,5,5-tetramethyl-1,3,2-dioxaborolan-2-yl)imidazo[1,2-b]pyridazine (3.22 g, 12.4 mmol, 1.2 eq., described herein above), Pd(Ph₃P)₄ (1.20 g, 1.03 mmol, 0.1 eq.) and an aqueous solution of K₂CO₃ (10.3 mL, 20.7 mmol, 2.0 eq.). The mixture was degassed and heated under argon at 100° C. for 6 hours. The reaction was cooled to RT, and filtered. The precipitate was washed with Et₂O and then water, dried in vacuo to give 1.80 g (56%) of 7-fluoro-9-methyl-2-(2-methylimidazo[1,2-b]pyridazin-6-yl)pyrido[1,2-a]pyrimidin-4-one as a light brown solid. MS m/z 310.1 [M+H]⁺.

Intermediate 4

2-(2,8-dimethylimidazo[1,2-b]pyridazin-6-yl)-7-fluoro-9-methyl-pyrido[1,2-a]pyrimidin-4-one

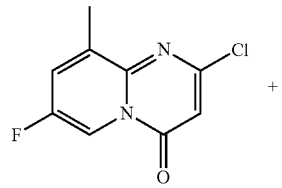

+

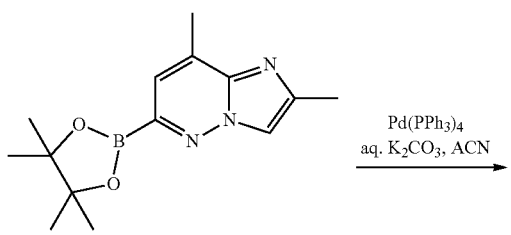

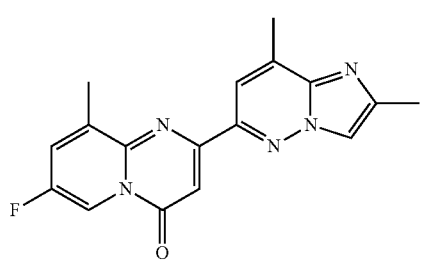

To a solution of 2-chloro-7-fluoro-9-methyl-4H-pyrido[1,2-a]pyrimidin-4-one (0.98 g, 4.61 mmol, described herein above) in ACN (50 mL) was added 2,8-dimethyl-6-(4,4,5,5-tetramethyl-1,3,2-dioxaborolan-2-yl)imidazo[1,2-b]pyridazine (1.51 g, 5.53 mmol, 1.2 eq., described herein above), Pd(Ph₃P)₄ (0.32 g, 0.277 mmol, 0.06 eq.) and an aqueous solution of K₂CO₃ (4.61 mL, 9.22 mmol, 2.0 eq.). The mixture was degassed and heated under argon at 100° C. for 6 hours. The reaction was cooled to RT, and filtered. The precipitate was washed with Et₂O and water, then dried in vacuo to give 0.89 g (60%) of 2-(2,8-dimethylimidazo[1,2-b]pyridazin-6-yl)-7-fluoro-9-methyl-pyrido[1,2-a]pyrimidin-4-one as a light brown solid. MS m/z 324.4 [M+H]⁺.

Example 1

2-(2-methylimidazo[1,2-b]pyridazin-6-yl)-7-(4-methylpiperazin-1-yl)pyrido[1,2-a]pyrimidin-4-one

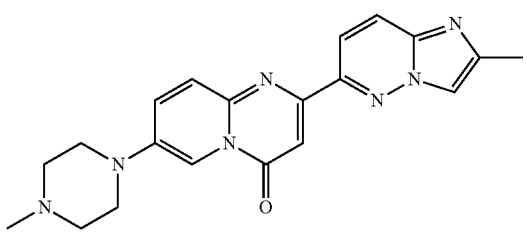

In a sealed tube, 7-fluoro-2-(2-methylimidazo[1,2-b]pyridazin-6-yl)-4H-pyrido[1,2-a]pyrimidin-4-one (Intermediate 1; 35 mg, 0.119 mmol) and 1-methylpiperazine (47.5 mg, 0.474 mmol, 4 eq.) were stirred in DMSO (1 mL) at 120° C. overnight. LC-MS showed total convertion. The solvent was removed under high vacuum. The crude product was purified by column chromatography (SiO₂, CH₂Cl₂/MeOH=95/5 to 9/1) to afford the title product (25 mg, 56%) as a light yellow solid. MS m/z 376.3 [M+H⁺].

Example 2

7-[(8aR)-3,4,6,7,8,8a-hexahydro-1H-pyrrolo[1,2-a]pyrazin-2-yl]-2-(2-methylimidazo[1,2-b]pyridazin-6-yl)pyrido[1,2-a]pyrimidin-4-one

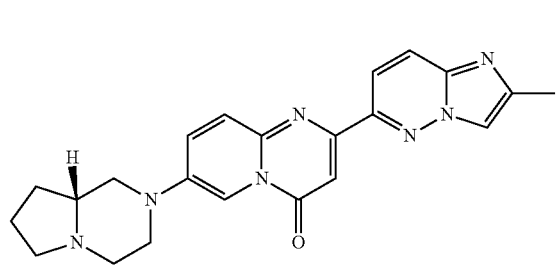 [SMILES: Cc1cn2nc(-c3cc(=O)n4cc(N5CCN6CCC[C@@H]6C5)ccc4n3)ccc2n1]

In a sealed tube, 7-fluoro-2-(2-methylimidazo[1,2-b]pyridazin-6-yl)-4H-pyrido[1,2-a]pyrimidin-4-one (Intermediate 1; 125 mg, 0.426 mmol) and (R)-octahydropyrrolo-[1,2-a]pyrazine (160 mg, 1.27 mmol, 3 eq.) were stirred in DMSO (5 mL) at 125° C. overnight. The solvent was removed under high vacuum. The residue was taken up in CH₂Cl₂ and washed with an aqueous saturated solution of NaHCO₃. The organic layer was separated and dried over Na₂SO₄ and concentrated in vacuo. The crude was purified by column chromatography (SiO₂, CH₂Cl₂/MeOH=98/2 to 95/5) to afford the title product (65 mg, 38%) as a light yellow solid. MS m/z 402.5 [M+H⁺].

Example 3

7-[(8aS)-3,4,6,7,8,8a-hexahydro-1H-pyrrolo[1,2-a]pyrazin-2-yl]-2-(2,8-dimethylimidazo[1,2-b]pyridazin-6-yl)pyrido[1,2-a]pyrimidin-4-one

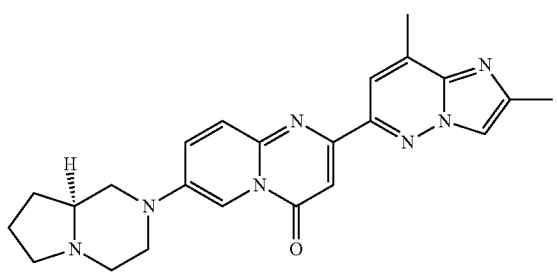 [SMILES: Cc1cn2nc(-c3cc(=O)n4cc(N5CCN6CCC[C@H]6C5)ccc4n3)cc(C)c2n1]

In a sealed tube, 2-(2,8-dimethylimidazo[1,2-b]pyridazin-6-yl)-7-fluoro-pyrido[1,2-a]pyrimidin-4-one (Intermediate 2; 200 mg, 0.647 mmol) and (S)-octahydropyrrolo-[1,2-a]pyrazine (286 mg, 2.26 mmol, 3.5 eq.) were stirred in DMSO (5 mL) at 125° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=98/2 to 95/5) to afford the title product (115 mg, 43%) as a light yellow solid. MS m/z 416.3 [M+H$^+$].

Example 4

7-[(8aR)-3,4,6,7,8,8a-hexahydro-1H-pyrrolo[1,2-a]pyrazin-2-yl]-2-(2,8-dimethylimidazo[1,2-b]pyridazin-6-yl)pyrido[1,2-a]pyrimidin-4-one

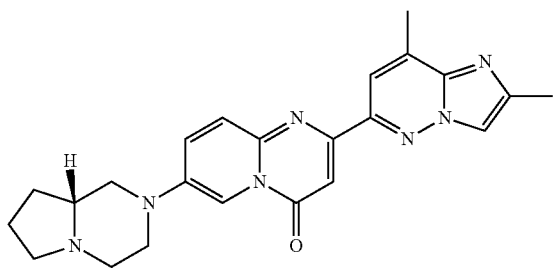 [SMILES: Cc1cn2nc(-c3cc(=O)n4cc(N5CCN6CCC[C@@H]6C5)ccc4n3)cc(C)c2n1]

In a sealed tube, 2-(2,8-dimethylimidazo[1,2-b]pyridazin-6-yl)-7-fluoro-pyrido[1,2-a]pyrimidin-4-one (Intermediate 2; 200 mg, 0.647 mmol), DIPEA (0.113 mL, 0.67 mmol, 1 eq.) and (R)-octahydropyrrolo-[1,2-a]pyrazine (245 mg, 1.95 mmol, 3.0 eq.) were stirred in DMSO (2.5 mL) at 125° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=98/2 to 95/5) to afford the title product (132 mg, 49%) as a light yellow solid. MS m/z 416.3 [M+H$^+$].

Example 5

7-[(8aS)-8a-methyl-1,3,4,6,7,8-hexahydropyrrolo[1,2-a]pyrazin-2-yl]-2-(2,8-dimethylimidazo[1,2-b]pyridazin-6-yl)pyrido[1,2-a]pyrimidin-4-one

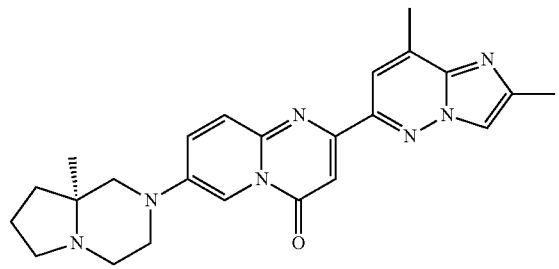 [SMILES: Cc1cn2nc(-c3cc(=O)n4cc(N5CCN6CCC[C@@]6(C)C5)ccc4n3)cc(C)c2n1]

In a sealed tube, 2-(2,8-dimethylimidazo[1,2-b]pyridazin-6-yl)-7-fluoro-pyrido[1,2-a]pyrimidin-4-one (Intermediate 2; 90 mg, 0.291 mmol), DIPEA (0.05 mL, 0.29 mmol, 1 eq.) and (S)-8a-methyloctahydropyrrolo[1,2-a]pyrazine (81 mg, 0.58 mmol, 2.0 eq.) were stirred in DMSO (2.5 mL) at 125° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (55 mg, 44%) as a light yellow solid. MS m/z 430.3 [M+H$^+$].

Example 6

7-[(8aR)-8a-methyl-1,3,4,6,7,8-hexahydropyrrolo[1,2-a]pyrazin-2-yl]-2-(2,8-dimethylimidazo[1,2-b]pyridazin-6-yl)pyrido[1,2-a]pyrimidin-4-one

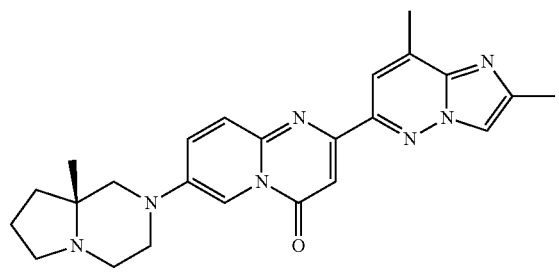 [SMILES: Cc1cn2nc(-c3cc(=O)n4cc(N5CCN6CCC[C@]6(C)C5)ccc4n3)cc(C)c2n1]

In a sealed tube, 2-(2,8-dimethylimidazo[1,2-b]pyridazin-6-yl)-7-fluoro-pyrido[1,2-a]pyrimidin-4-one (Intermediate 2; 90 mg, 0.291 mmol), DIPEA (0.05 mL, 0.29 mmol, 1 eq.) and (R)-8a-methyloctahydropyrrolo[1,2-a]pyrazine (81 mg, 0.58 mmol, 2.0 eq.) were stirred in DMSO (2.5 mL) at 125° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (50 mg, 40%) as a light yellow solid. MS m/z 430.4 [M+H$^+$].

Example 7

2-(2,8-dimethylimidazo[1,2-b]pyridazin-6-yl)-7-[(3S,5R)-3,5-dimethylpiperazin-1-yl]pyrido[1,2-a]pyrimidin-4-one

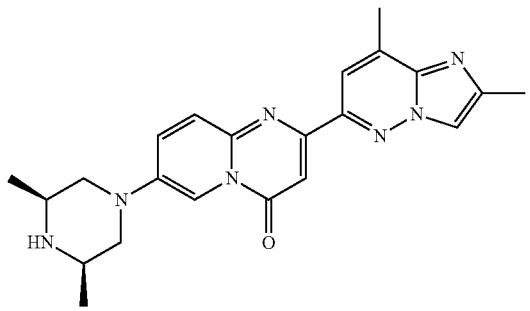

In a sealed tube, 2-(2,8-dimethylimidazo[1,2-b]pyridazin-6-yl)-7-fluoro-pyrido[1,2-a]pyrimidin-4-one (Intermediate 2; 50 mg, 0.162 mmol), and cis-2,6-dimethylpiperazine (74 mg, 0.647 mmol, 4.0 eq.) were stirred in DMSO (1.5 mL) at 110° C. overnight. The solvent was removed under high vacuum. The residue was taken up in $CH_2Cl_{12}$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (32 mg, 49%) as a light yellow solid. MS m/z 404.4 [M+H$^+$].

Example 8

2-(2,8-dimethylimidazo[1,2-b]pyridazin-6-yl)-7-[(3S)-3-methylpiperazin-1-yl]pyrido[1,2-a]pyrimidin-4-one

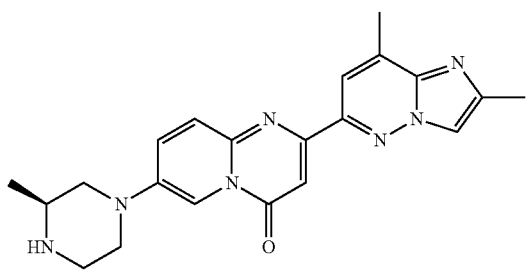

In a sealed tube, 2-(2,8-dimethylimidazo[1,2-b]pyridazin-6-yl)-7-fluoro-pyrido[1,2-a]pyrimidin-4-one (Intermediate 2; 33 mg, 0.107 mmol), and (S)-2-methylpiperazine (43 mg, 0.427 mmol, 4.0 eq.) were stirred in DMSO (2 mL) at 120° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (18 mg, 43%) as a light yellow solid. MS m/z 390.3 [M+H$^+$].

Example 9

2-(2,8-dimethylimidazo[1,2-b]pyridazin-6-yl)-7-[(3R)-3-methylpiperazin-1-yl]pyrido[1,2-a]pyrimidin-4-one

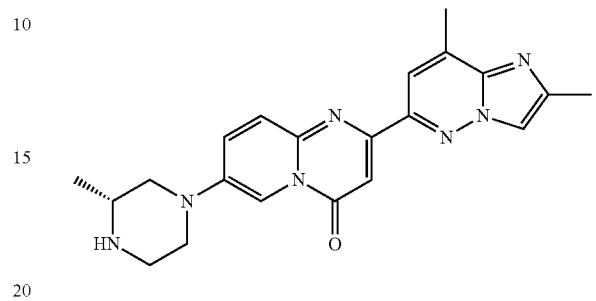

In a sealed tube, 2-(2,8-dimethylimidazo[1,2-b]pyridazin-6-yl)-7-fluoro-pyrido[1,2-a]pyrimidin-4-one (Intermediate 2; 85 mg, 0.275 mmol), and (R)-2-methylpiperazine (110 mg, 1.10 mmol, 4.0 eq.) were stirred in DMSO (5 mL) at 120° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (35 mg, 33%) as a light yellow solid. MS m/z 390.3 [M+H$^+$].

Example 10

7-(1,4-diazepan-1-yl)-(2,8-dimethylimidazo[1,2-b]pyridazin-6-yl)pyrido[1,2-a]pyrimidin-4-one

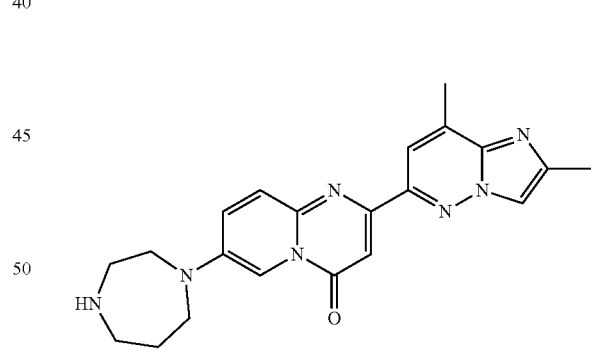

In a sealed tube, 2-(2,8-dimethylimidazo[1,2-b]pyridazin-6-yl)-7-fluoro-pyrido[1,2-a]pyrimidin-4-one (Intermediate 2; 33 mg, 0.107 mmol), and 1,4-diazepane (32 mg, 0.320 mmol, 3.0 eq.) were stirred in DMSO (2 mL) at 120° C. overnight. The solvent was removed under high vacuum. The residue was taken up in $CH_2Cl_{12}$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (20 mg, 48%) as a light yellow solid. MS m/z 390.3 [M+H$^+$].

Example 11

2-(2-methylimidazo[1,2-b]pyridazin-6-yl)-7-[(3S)-3-methylpiperazin-1-yl]pyrido[1,2-a]pyrimidin-4-one

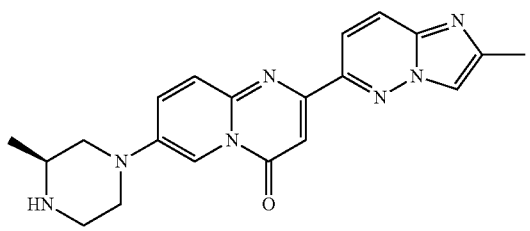

In a sealed tube, 7-fluoro-2-(2-methylimidazo[1,2-b]pyridazin-6-yl)-4H-pyrido[1,2-a]pyrimidin-4-one (Intermediate 1; 50 mg, 0.169 mmol), and (S)-2-methylpiperazine (68 mg, 0.677 mmol, 4.0 eq.) were stirred in DMSO (2 mL) at 110° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (40 mg, 63%) as a light yellow solid. MS m/z 376.2 [M+H$^+$].

Example 12

2-(2-methylimidazo[1,2-b]pyridazin-6-yl)-7-[(3R)-3-methylpiperazin-1-yl]pyrido[1,2-a]pyrimidin-4-one

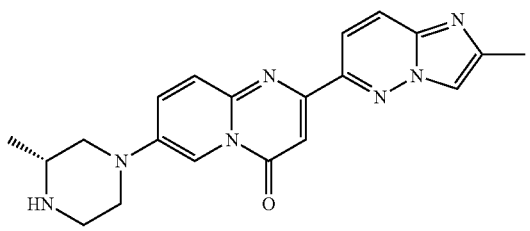

In a sealed tube, 7-fluoro-2-(2-methylimidazo[1,2-b]pyridazin-6-yl)-4H-pyrido[1,2-a]pyrimidin-4-one (Intermediate 1; 50 mg, 0.169 mmol), and (R)-2-methylpiperazine (68 mg, 0.677 mmol, 4.0 eq.) were stirred in DMSO (2 mL) at 110° C. overnight. The solvent was removed under high vacuum. The residue was taken up in $CH_2Cl_{12}$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (48 mg, 75%) as a light yellow solid. MS m/z 376.3 [M+H$^+$].

Example 13

7-(1,4-diazepan-1-yl)-2-(2-methylimidazo[1,2-b]pyridazin-6-yl)pyrido[1,2-a]pyrimidin-4-one

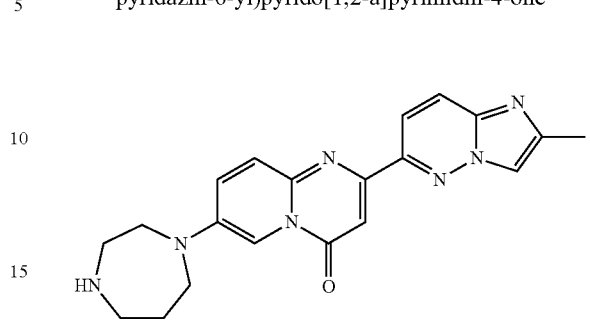

In a sealed tube, 7-fluoro-2-(2-methylimidazo[1,2-b]pyridazin-6-yl)-4H-pyrido[1,2-a]pyrimidin-4-one (Intermediate 1; 50 mg, 0.169 mmol), and 1,4-diazepane (68 mg, 0.677 mmol, 4.0 eq.) were stirred in DMSO (2 mL) at 110° C. overnight. The solvent was removed under high vacuum. The residue was taken up in $CH_2Cl_{12}$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (41 mg, 65%) as a light yellow solid. MS m/z 376.2 [M+H$^+$].

Example 14

7-[(3R,5S)-3,5-dimethylpiperazin-1-yl]-2-(2-methylimidazo[1,2-b]pyridazin-6-yl)pyrido[1,2-a]pyrimidin-4-one

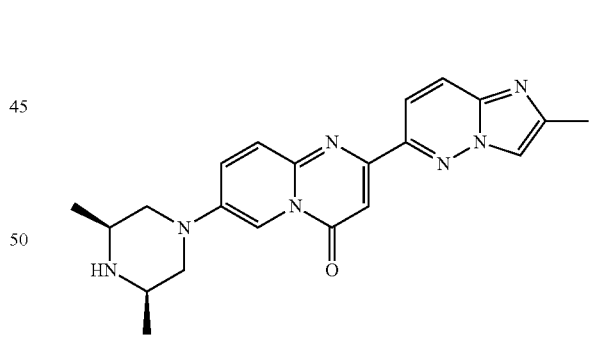

In a sealed tube, 7-fluoro-2-(2-methylimidazo[1,2-b]pyridazin-6-yl)-4H-pyrido[1,2-a]pyrimidin-4-one (Intermediate 1; 50 mg, 0.169 mmol), and cis-2,6-dimethylpiperazine (77 mg, 0.677 mmol, 4.0 eq.) were stirred in DMSO (2 mL) at 110° C. overnight. The solvent was removed under high vacuum. The residue was taken up in $CH_2Cl_{12}$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (41 mg, 62%) as a light yellow solid. MS m/z 390.3 [M+H$^+$].

Example 15

7-[(8aS)-3,4,6,7,8,8a-hexahydro-1H-pyrrolo[1,2-a]pyrazin-2-yl]-2-(2-methylimidazo[1,2-b]pyridazin-6-yl)pyrido[1,2-a]pyrimidin-4-one

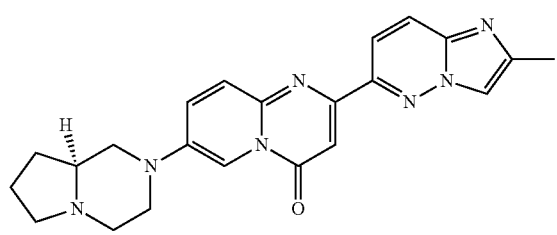 [SMILES: Cc1cn2nc(-c3cc(=O)n4cc(N5CCN6CCC[C@H]6C5)ccc4n3)ccc2n1]

In a sealed tube, 7-fluoro-2-(2-methylimidazo[1,2-b]pyridazin-6-yl)-4H-pyrido[1,2-a]pyrimidin-4-one (Intermediate 1; 50 mg, 0.169 mmol), and (S)-octahydropyrrolo[1,2-a]pyrazine (85 mg, 0.677 mmol, 4.0 eq.) were stirred in DMSO (2 mL) at 125° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 90/10) to afford the title product (36 mg, 53%) as a light yellow solid. MS m/z 402.3 [M+H$^+$].

Example 16

7-[(8aS)-8a-methyl-1,3,4,6,7,8-hexahydropyrrolo[1,2-a]pyrazin-2-yl]-2-(2-methylimidazo[1,2-b]pyridazin-6-yl)pyrido[1,2-a]pyrimidin-4-one

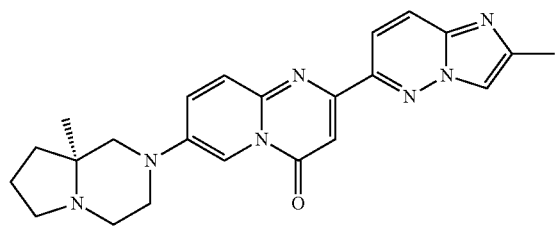 [SMILES: Cc1cn2nc(-c3cc(=O)n4cc(N5CCN6CCC[C@@]6(C)C5)ccc4n3)ccc2n1]

In a sealed tube, 7-fluoro-2-(2-methylimidazo[1,2-b]pyridazin-6-yl)-4H-pyrido[1,2-a]pyrimidin-4-one (Intermediate 1; 50 mg, 0.169 mmol) and (S)-8a-methyloctahydropyrrolo[1,2-a]pyrazine (95 mg, 0.677 mmol, 4.0 eq.) were stirred in DMSO (2 mL) at 125° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 90/10) to afford the title product (45 mg, 64%) as a light yellow solid. MS m/z 416.3 [M+H$^+$].

Example 17

7-[(8aR)-8a-methyl-1,3,4,6,7,8-hexahydropyrrolo[1,2-a]pyrazin-2-yl]-2-(2-methylimidazo[1,2-b]pyridazin-6-yl)pyrido[1,2-a]pyrimidin-4-one

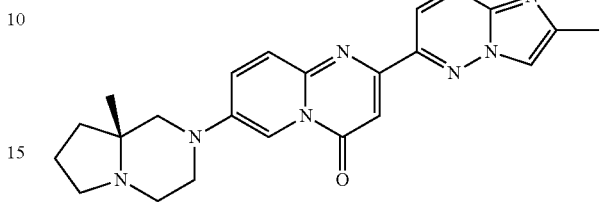

In a sealed tube, 7-fluoro-2-(2-methylimidazo[1,2-b]pyridazin-6-yl)-4H-pyrido[1,2-a]pyrimidin-4-one (Intermediate 1; 100 mg, 0.339 mmol) and (R)-8a-methyloctahydropyrrolo[1,2-a]pyrazine (190 mg, 1.35 mmol, 4.0 eq.) were stirred in DMSO (4 mL) at 125° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 90/10) to afford the title product (45 mg, 64%) as a light yellow solid. MS m/z 416.3 [M+H$^+$].

Example 18

2-(2,8-dimethylimidazo[1,2-b]pyridazin-6-yl)-7-[(3R)-3-pyrrolidin-1-ylpyrrolidin-1-yl]pyrido[1,2-a]pyrimidin-4-one

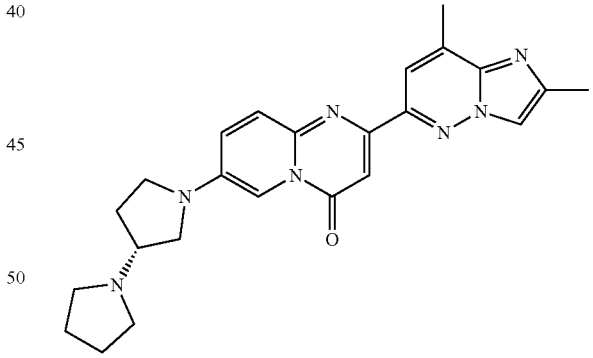

In a microwave reactor, 2-(2,8-dimethylimidazo[1,2-b]pyridazin-6-yl)-7-fluoro-pyrido[1,2-a]pyrimidin-4-one (Intermediate 2; 45 mg, 0.145 mmol), (R)-1,3'-bipyrrolidine dihydrochloride (62 mg, 0.291 mmol, 2.0 eq.) and DIPEA (0.20 mL, 1.16 mmol, 8 eq.) were stirred in NMP (3 mL) at 220° C. for 1 hour. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=98/2 to 90/10) to afford the title product (25 mg, 40%) as a light yellow solid. MS m/z 430.3 [M+H$^+$].

Example 19

7-(4,7-diazaspiro[2.5]octan-7-yl)-2-(2-methylimidazo[1,2-b]pyridazin-6-yl)pyrido[1,2-a]pyrimidin-4-one

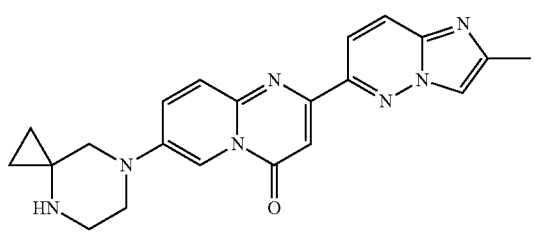 [SMILES: Cc1cn2nc(-c3cc(=O)n4cc(N5CCNC6(CC6)C5)ccc4n3)ccc2n1]

In a sealed tube, 7-fluoro-2-(2-methylimidazo[1,2-b]pyridazin-6-yl)-4H-pyrido[1,2-a]pyrimidin-4-one (Intermediate 1; 50 mg, 0.169 mmol), DIPEA (0.24 mL, 1.35 mmol, 8 eq.) and 4,7-diazaspiro[2.5]octane dihydrochloride (62.7 mg, 0.339 mmol, 2.0 eq.) were stirred in DMSO (2 mL) at 125° C. for 2 days. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (22 mg, 33%) as a light yellow solid. MS m/z 388.3 [M+H$^+$].

Example 20

7-(4,7-diazaspiro[2.5]octan-7-yl)-2-(2,8-dimethylimidazo[1,2-b]pyridazin-6-yl)pyrido[1,2-a]pyrimidin-4-one

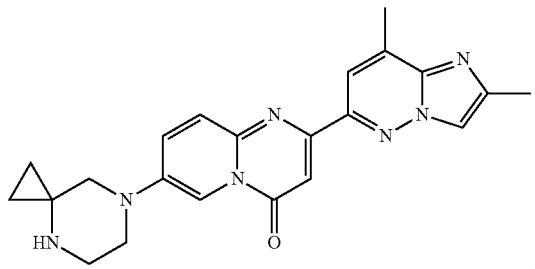 [SMILES: Cc1cn2nc(-c3cc(=O)n4cc(N5CCNC6(CC6)C5)ccc4n3)cc(C)c2n1]

In a sealed tube, 2-(2,8-dimethylimidazo[1,2-b]pyridazin-6-yl)-7-fluoro-pyrido[1,2-a]pyrimidin-4-one (Intermediate 2; 50 mg, 0.162 mmol), DIPEA (0.22 mL, 1.29 mmol, 4 eq.) and 4,7-diazaspiro[2.5]octane dihydrochloride (32 mg, 0.320 mmol, 3.0 eq.) were stirred in DMSO (2 mL) at 130° C. for 48 hours. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=98/2 to 95/5) to afford the title product (12 mg, 18%) as a light yellow solid. MS m/z 402.3 [M+H$^+$].

Example 21

2-(2-methylimidazo[1,2-b]pyridazin-6-yl)-7-[(3R)-3-pyrrolidin-1-ylpyrrolidin-1-yl]pyrido[1,2-a]pyrimidin-4-one

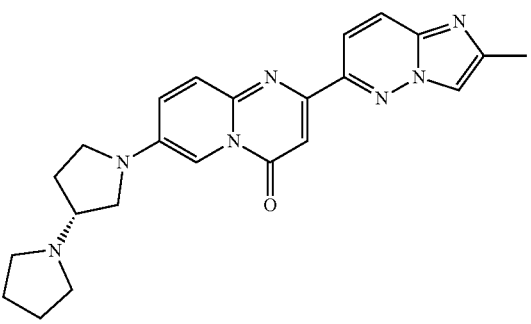 [SMILES: Cc1cn2nc(-c3cc(=O)n4cc(N5CC[C@@H](N6CCCC6)C5)ccc4n3)ccc2n1]

In a sealed tube, 7-fluoro-2-(2-methylimidazo[1,2-b]pyridazin-6-yl)-4H-pyrido[1,2-a]pyrimidin-4-one (Intermediate 1; 40 mg, 0.135 mmol), DIPEA (0.19 mL, 1.08 mmol, 8 eq.) and (R)-1,3'-bipyrrolidine dihydrochloride (58 mg, 0.271 mmol, 2.0 eq.) were stirred in DMSO (4 mL) and heated at 220° C. for 40 minutes in a microwave. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=98/2 to 90/10) to afford the title product (30 mg, 53%) as a light yellow solid. MS m/z 416.3 [M+H$^+$].

Example 22

2-(2,8-dimethylimidazo[1,2-b]pyridazin-6-yl)-7-(3,3-dimethylpiperazin-1-yl)pyrido[1,2-a]pyrimidin-4-one

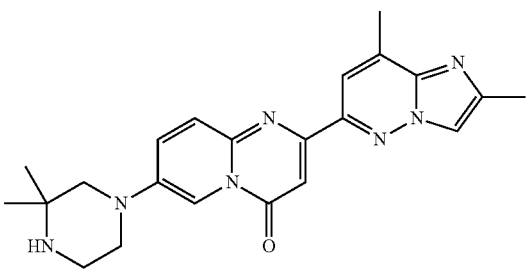

In a sealed tube, 2-(2,8-dimethylimidazo[1,2-b]pyridazin-6-yl)-7-fluoro-pyrido[1,2-a]pyrimidin-4-one (Intermediate 2; 40 mg, 0.129 mmol) and 2,2-dimethylpiperazine (59 mg, 0.517 mmol, 4.0 eq.) were stirred in DMSO (1.6 mL) at 130° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 9/1) to afford the title product (29 mg, 55%) as a light yellow solid. MS m/z 404.3 [M+H$^+$].

Example 23

7-(3,3-dimethylpiperazin-1-yl)-2-(2-methylimidazo[1,2-b]pyridazin-6-yl)pyrido[1,2-a]pyrimidin-4-one

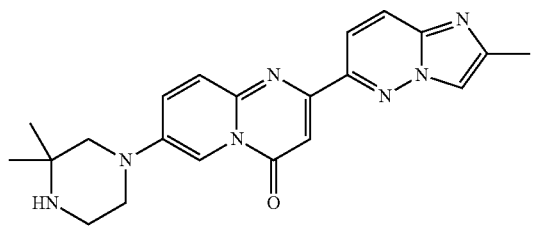

In a sealed tube, 7-fluoro-2-(2-methylimidazo[1,2-b]pyridazin-6-yl)-4H-pyrido[1,2-a]pyrimidin-4-one (Intermediate 1; 40 mg, 0.135 mmol) and 2,2-dimethylpiperazine (62 mg, 0.542 mmol, 4.0 eq.) were stirred in DMSO (2 mL) at 130° C. overnight. The solvent was removed under high vacuum. The residue was taken up in $CH_2Cl_{12}$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (26 mg, 49%) as a light yellow solid. MS m/z 390.3 [M+H$^+$].

Example 24

2-(2,8-dimethylimidazo[1,2-b]pyridazin-6-yl)-9-methyl-7-[(3S)-3-methylpiperazin-1-yl]pyrido[1,2-a]pyrimidin-4-one

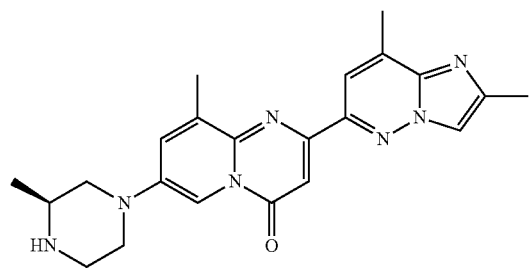

In a sealed tube, 2-(2,8-dimethylimidazo[1,2-b]pyridazin-6-yl)-7-fluoro-9-methyl-pyrido[1,2-a]pyrimidin-4-one (Intermediate 4; 50 mg, 0.155 mmol) and (S)-2-methylpiperazine (62 mg, 0.619 mmol, 4.0 eq.) were stirred in DMSO (2 mL) at 125° C. overnight. The solvent was removed under high vacuum. The residue was taken up in $CH_2Cl_{12}$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (45 mg, 72%) as a light yellow solid. MS m/z 404.3 [M+H$^+$].

Example 25

2-(2,8-dimethylimidazo[1,2-b]pyridazin-6-yl)-9-methyl-7-[(3R)-3-methylpiperazin-1-yl]pyrido[1,2-a]pyrimidin-4-one

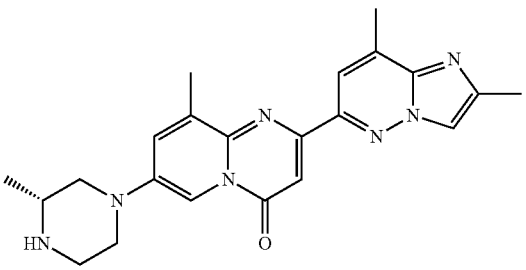

In a sealed tube, 2-(2,8-dimethylimidazo[1,2-b]pyridazin-6-yl)-7-fluoro-9-methyl-pyrido[1,2-a]pyrimidin-4-one (Intermediate 4; 50 mg, 0.155 mmol) and (R)-2-methylpiperazine (62 mg, 0.619 mmol, 4.0 eq.) were stirred in DMSO (2 mL) at 125° C. overnight. The solvent was removed under high vacuum. The residue was taken up in $CH_2Cl_{12}$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (40 mg, 70%) as a light yellow solid. MS m/z 404.3 [M+H$^+$].

Example 26

2-(2,8-dimethylimidazo[1,2-b]pyridazin-6-yl)-7-[(3R,5S)-3,5-dimethylpiperazin-1-yl]-9-methyl-pyrido[1,2-a]pyrimidin-4-one

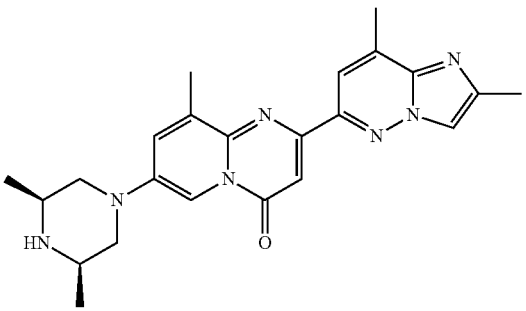

In a sealed tube, 2-(2,8-dimethylimidazo[1,2-b]pyridazin-6-yl)-7-fluoro-9-methyl-pyrido[1,2-a]pyrimidin-4-one (Intermediate 4; 50 mg, 0.155 mmol) and cis-2,6-dimethylpiperazine (70 mg, 0.619 mmol, 4.0 eq.) were stirred in DMSO (2 mL) at 125° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (26 mg, 40%) as a light yellow solid. MS m/z 418.3 [M+H$^+$].

Example 27

2-(2,8-dimethylimidazo[1,2-b]pyridazin-6-yl)-7-(3,3-dimethylpiperazin-1-yl)-9-methyl-pyrido[1,2-a]pyrimidin-4-one

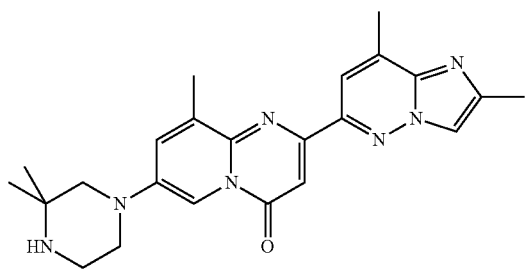

In a sealed tube, 2-(2,8-dimethylimidazo[1,2-b]pyridazin-6-yl)-7-fluoro-9-methyl-pyrido[1,2-a]pyrimidin-4-one (Intermediate 4; 50 mg, 0.155 mmol) and 2,2-dimethylpiperazine (35 mg, 0.309 mmol, 2.0 eq.) were stirred in DMSO (2 mL) at 125° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (36 mg, 56%) as a light yellow solid. MS m/z 418.3 [M+H⁺].

Example 28

7-(4,7-diazaspiro[2.5]octan-7-yl)-2-(2,8-dimethyl-imidazo[1,2-b]pyridazin-6-yl)-9-methyl-pyrido[1,2-a]pyrimidin-4-one

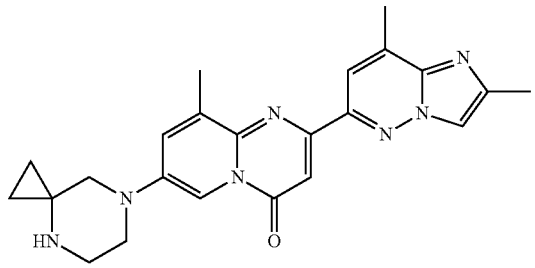 [SMILES: Cc1cn2nc(-c3cc(=O)n4cc(N5CCNC6(CC6)C5)cc(C)c4n3)cc(C)c2n1]

In a sealed tube, 2-(2,8-dimethylimidazo[1,2-b]pyridazin-6-yl)-7-fluoro-9-methyl-pyrido[1,2-a]pyrimidin-4-one (Intermediate 4; 50 mg, 0.155 mmol), DIPEA (0.21 mL, 1.24 mmol, 8 eq.) and 4,7-diazaspiro[2.5]octane dihydrochloride (57 mg, 0.309 mmol, 2.0 eq.) were stirred in DMSO (2 mL) at 125° C. for 2 days. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 90/10) to afford the title product (17 mg, 26%) as a light yellow solid. MS m/z 416.3 [M+H⁺].

Example 29

2-(2,8-dimethylimidazo[1,2-b]pyridazin-6-yl)-7-[(3S,5S)-3,5-dimethylpiperazin-1-yl]pyrido[1,2-a]pyrimidin-4-one

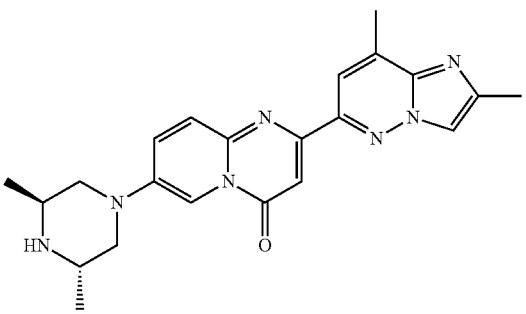

In a sealed tube, 2-(2,8-dimethylimidazo[1,2-b]pyridazin-6-yl)-7-fluoro-pyrido[1,2-a]pyrimidin-4-one (Intermediate 2; 50 mg, 0.162 mmol), TEA (0.18 mL, 1.29 mmol, 8 eq.) and (2S,6S)-2,6-dimethylpiperazine dihydrochloride (90 mg, 0.485 mmol, 3.0 eq.) were stirred in DMSO (2 mL) at 140° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography ($SiO_2$, $CH_2Cl_2$/MeOH=95/5 to 9/1) to afford the title product (20 mg, 30%) as a light yellow solid. MS m/z 404.3 [M+H⁺].

Example 30

2-(2,8-dimethylimidazo[1,2-b]pyridazin-6-yl)-7-[(3S)-3-pyrrolidin-1-ylpyrrolidin-1-yl]pyrido[1,2-a]pyrimidin-4-one

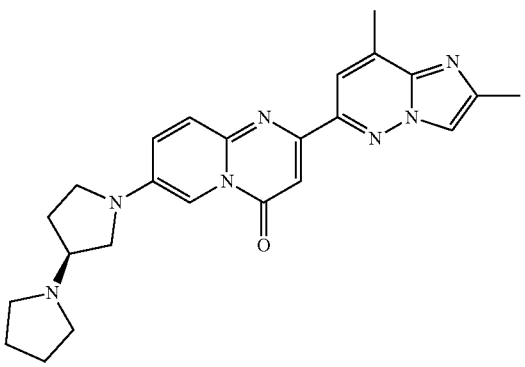 [SMILES: Cc1cn2nc(-c3cc(=O)n4cc(N5CC[C@H](N6CCCC6)C5)ccc4n3)cc(C)c2n1]

In a sealed tube, 2-(2,8-dimethylimidazo[1,2-b]pyridazin-6-yl)-7-fluoro-pyrido[1,2-a]pyrimidin-4-one (Intermediate 2; 50 mg, 0.162 mmol), DIPEA (0.22 mL, 1.29 mmol, 8 eq.) and (S)-1,3'-bipyrrolidine dihydrochloride (103 mg, 0.485 mmol, 3.0 eq.) were stirred in NMP (2 mL) at 140° C. overnight. The solvent was removed under high vacuum. The residue was taken up in $CH_2Cl_2$ and washed with an aqueous saturated solution of $NaHCO_3$. The organic layer was separated and dried over $Na_2SO_4$ and concentrated in vacuo. The crude was purified by column chromatography (SiO$_2$, CH$_2$Cl$_2$/MeOH=95/5 to 9/1) to afford the title product (22 mg, 32%) as a light yellow solid. MS m/z 430.3 [M+H$^+$].

Example 31

2-(2-methylimidazo[1,2-b]pyridazin-6-yl)-7-[(3S)-3-pyrrolidin-1-ylpyrrolidin-1-yl]pyrido[1,2-a]pyrimidin-4-one

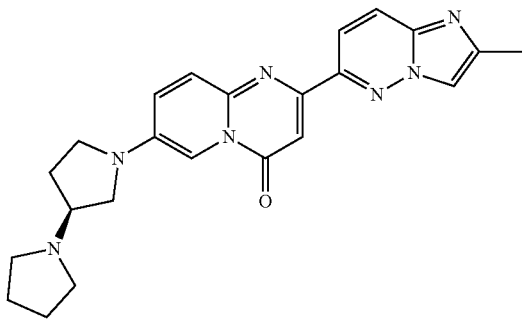 [SMILES: Cc1cn2nc(-c3cc(=O)n4cc(N5CC[C@H](N6CCCC6)C5)ccc4n3)ccc2n1]

In a sealed tube, 7-fluoro-2-(2-methylimidazo[1,2-b]pyridazin-6-yl)-4H-pyrido[1,2-a]pyrimidin-4-one (Intermediate 1; 75 mg, 0.254 mmol), TEA (0.28 mL, 2.03 mmol, 8 eq.) and (S)-1,3'-bipyrrolidine dihydrochloride (162 mg, 0.762 mmol, 3.0 eq.) were stirred in NMP (4 mL) and heated at 220° C. for 1 hour in a microwave. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 90/10) to afford the title product (12 mg, 11%) as a light yellow solid. MS m/z 416.2 [M+H$^+$].

Example 32

7-[(3S,5S)-3,5-dimethylpiperazin-1-yl]-2-(2-methylimidazo[1,2-b]pyridazin-6-yl)pyrido[1,2-a]pyrimidin-4-one

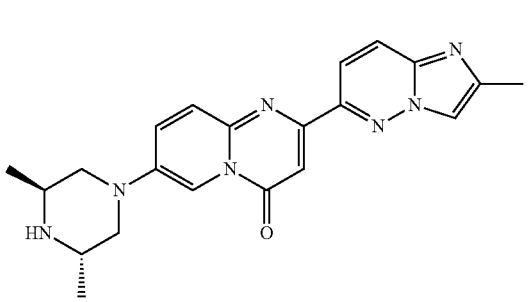

In a sealed tube, 7-fluoro-2-(2-methylimidazo[1,2-b]pyridazin-6-yl)-4H-pyrido[1,2-a]pyrimidin-4-one (Intermediate 1; 75 mg, 0.254 mmol), TEA (0.28 mL, 2.03 mmol, 8 eq.) and (2S,6S)-2,6-dimethylpiperazine dihydrochloride (143 mg, 0.762 mmol, 3.0 eq.) were stirred in DMSO (3 mL) and heated at 140° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 90/10) to afford the title product (10 mg, 10%) as a light yellow solid. MS m/z 390.3 [M+H$^+$].

Example 33

9-methyl-2-(2-methylimidazo[1,2-b]pyridazin-6-yl)-7-[(3S)-3-methylpiperazin-1-yl]pyrido[1,2-a]pyrimidin-4-one

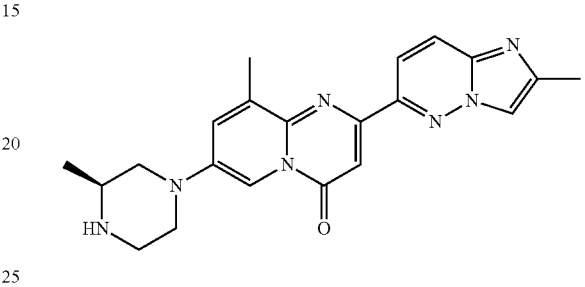

In a sealed tube, 7-fluoro-9-methyl-2-(2-methylimidazo[1,2-b]pyridazin-6-yl)pyrido[1,2-a]pyrimidin-4-one (Intermediate 3; 250 mg, 0.808 mmol), and (S)-2-methylpiperazine (405 mg, 4.04 mmol, 5.0 eq.) were stirred in DMSO (6 mL) and heated at 130° C. overnight. The solvent was removed under high vacuum. The residue was taken up in CH$_2$Cl$_{12}$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 85/15) to afford the title product (135 mg, 43%) as a light yellow solid. MS m/z 390.3 [M+H$^+$].

Example 34

9-methyl-2-(2-methylimidazo[1,2-b]pyridazin-6-yl)-7-[(3R)-3-methylpiperazin-1-yl]pyrido[1,2-a]pyrimidin-4-one

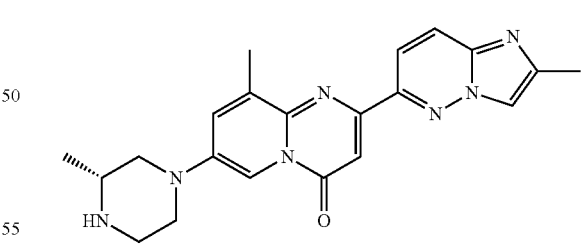

In a sealed tube, 7-fluoro-9-methyl-2-(2-methylimidazo[1,2-b]pyridazin-6-yl)pyrido[1,2-a]pyrimidin-4-one (Intermediate 3; 250 mg, 0.808 mmol), and (R)-2-methylpiperazine (405 mg, 4.04 mmol, 5.0 eq.) were stirred in DMSO (6 mL) and heated at 130° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to

Example 35

7-[(3R,5S)-3,5-dimethylpiperazin-1-yl]-9-methyl-2-(2-methylimidazo[1,2-b]pyridazin-6-yl)pyrido[1,2-a]pyrimidin-4-one

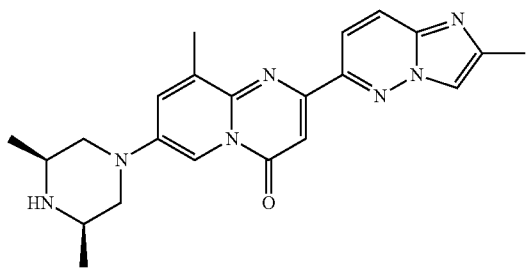

In a sealed tube, 7-fluoro-9-methyl-2-(2-methylimidazo[1,2-b]pyridazin-6-yl)pyrido[1,2-a]pyrimidin-4-one (Intermediate 3; 250 mg, 0.808 mmol), and (2S,6R)-2,6-dimethylpiperazine (461 mg, 4.04 mmol, 5.0 eq.) were stirred in DMSO (6 mL) and heated at 130° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 85/15) to afford the title product (101 mg, 31%) as a light yellow solid. MS m/z 404.3 [M+H$^+$].

Example 36

7-(3,3-dimethylpiperazin-1-yl)-9-methyl-2-(2-methylimidazo[1,2-b]pyridazin-6-yl)pyrido[1,2-a]pyrimidin-4-one

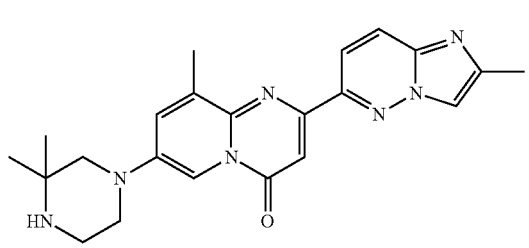

In a sealed tube, 7-fluoro-9-methyl-2-(2-methylimidazo[1,2-b]pyridazin-6-yl)pyrido[1,2-a]pyrimidin-4-one (Intermediate 3; 250 mg, 0.808 mmol), and 2,2-dimethylpiperazine (461 mg, 4.04 mmol, 5.0 eq.) were stirred in DMSO (6 mL) and heated at 130° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 85/15) to afford the title product (120 mg, 36%) as a light yellow solid. MS m/z 404.3 [M+H$^+$].

Example 37

7-(4,7-diazaspiro[2.5]octan-7-yl)-9-methyl-2-(2-methylimidazo[1,2-b]pyridazin-6-yl)pyrido[1,2-a]pyrimidin-4-one

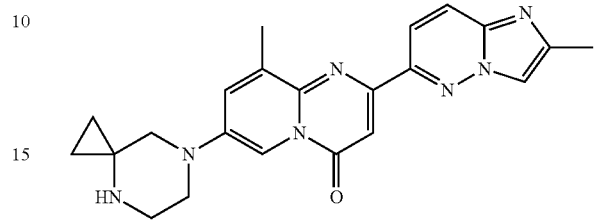

In a sealed tube, 7-fluoro-9-methyl-2-(2-methylimidazo[1,2-b]pyridazin-6-yl)pyrido[1,2-a]pyrimidin-4-one (Intermediate 3; 125 mg, 0.404 mmol), K$_2$CO$_3$ (223 mg, 1.62 mmol, 4 eq.) and 4,7-diazaspiro[2.5]octane dihydrochloride (112 mg, 0.606 mmol, 1.5 eq.) were stirred in DMA (2 mL) and heated at 130° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 90/10) to afford the title product (75 mg, 46%) as a light yellow solid. MS m/z 402.2 [M+H$^+$].

Example 38

7-[(3S,5S)-3,5-dimethylpiperazin-1-yl]-9-methyl-2-(2-methylimidazo[1,2-b]pyridazin-6-yl)pyrido[1,2-a]pyrimidin-4-one

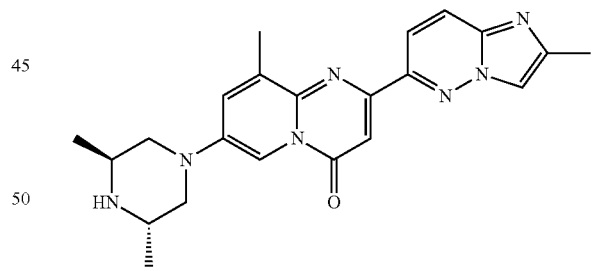

In a sealed tube, 7-fluoro-9-methyl-2-(2-methylimidazo[1,2-b]pyridazin-6-yl)pyrido[1,2-a]pyrimidin-4-one (Intermediate 3; 125 mg, 0.404 mmol), K$_2$CO$_3$ (223 mg, 1.62 mmol, 4 eq.) and (2S,6S)-2,6-dimethylpiperazine dihydrochloride (113 mg, 0.606 mmol, 1.5 eq.) were stirred in DMA (2 mL) and heated at 130° C. overnight. The solvent was removed under high vacuum. The residue was taken up in CH$_2$Cl$_2$ and washed with an aqueous saturated solution of NaHCO$_3$. The organic layer was separated and dried over Na$_2$SO$_4$ and concentrated in vacuo. The crude was purified by column chromatography (SiO$_2$, CH$_2$Cl$_2$/MeOH=95/5 to 90/10) to afford the title product (50 mg, 31%) as a light yellow solid. MS m/z 404.3 [M+H$^+$].

Example 39

7-[(3R)-3-ethylpiperazin-1-yl]-2-(2-methylimidazo[1,2-b]pyridazin-6-yl)pyrido[1,2-a]pyrimidin-4-one

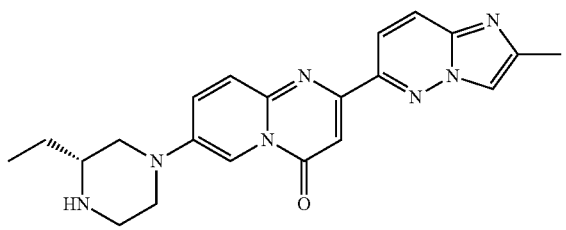 [SMILES: CC[C@@H]1CN(c2ccc3nc(-c4ccc5nc(C)cn5n4)cc(=O)n3c2)CCN1]

In a sealed tube, 7-fluoro-2-(2-methylimidazo[1,2-b]pyridazin-6-yl)-4H-pyrido[1,2-a]pyrimidin-4-one (Intermediate 1; 200 mg, 0.677 mmol), $K_2CO_3$ (374 mg, 2.71 mmol, 4 eq.) and (R)-2-ethylpiperazine dihydrochloride (238 mg, 0.606 mmol, 1.5 eq.) were stirred in DMA (3 mL) at 100° C. for 4 days. The solvent was removed under high vacuum. The crude was purified by column chromatography ($SiO_2$, $CH_2Cl_2$/MeOH=95/5 to 8/2) to afford the title product (168 mg, 64%) as a light yellow solid. MS m/z 390.2 [M+H$^+$].

Example 40

SMN2 Minigene mRNA Splicing RT-qPCR Assay in Cultured Cells

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed. These examples illustrate the testing of certain compounds described herein in vitro and/or in vivo and demonstrate the usefulness of the compounds for treating of SMA by enhancing the inclusion of exon 7 of SMN2 into mRNA transcribed from the SMN2 gene. Compounds of formula (I) enhance inclusion of exon 7 of SMN2 into mRNA transcribed from the SMN2 gene and increase levels of SMN protein produced from the SMN2 gene, and thus can be used to treat SMA in a human subject in need thereof. These examples further illustrate the testing of certain compounds described herein in vitro and/or in vivo and demonstrate the usefulness of the compounds for enhancing the inclusion of exon 7 of SMNI into mRNA transcribed from the SMN1 gene. Accordingly, compounds of formula (I) also enhance the inclusion of exon 7 of SMN1 into mRNA transcribed from the SMN1 gene and increase levels of SMN protein produced from the SMN1 gene.

The reverse transcription-quantitative PCR-based (RT-qPCR) assay is used to quantify the level of the full length SMN2 minigene (referred to herein by the term "FL SMN2mini") mRNA containing SMN2 exon 7 in a HEK293H cell line stably transfected with said minigene and treated with a test compound. Materials used and respective sources are listed below in Table 1.

TABLE 1

Materials and their respective sources used in the SMN2 minigene mRNA splicing RT-qPCR assay in cultured cells.

| Material | Source |
| --- | --- |
| HEK293H cells | Life Technologies, Inc. (formerly Invitrogen) Catalog No. 11631-017 |
| Cells-To-Ct lysis buffer | Life Technologies, Inc. (formerly Applied Biosystems) part No. 4399002 |
| DMEM | Life Technologies, Inc. (formerly Invitrogen) Catalog No. 11960-044 |
| 96-well flat-bottom plates | Becton Dickinson Catalog No. 353072 |
| RT-PCR Enzyme Mix | Life Technologies, Inc. (formerly Applied Biosystems) part No. 4388520 |
| RT-PCR buffer | Life Technologies, Inc. (formerly Applied Biosystems) part No. 4388519 |
| AgPath-ID One-Step RT-PCR kit | Life Technologies, Inc. (formerly Applied Biosystems) part No. 4387391 |
| Thermocycler | Life Technologies, Inc. (formerly Applied Biosystems) 7900HT |

The SMN2-A minigene construct was prepared as described in International Patent Application WO2009/151546A1 page 145 paragraph [00400] to page 147 paragraph [00412](incl. FIG. 1 and FIG. 3 therein).

HEK293H cells stably transfected with the SMN2-A minigene construct (10,000 cells/well) are seeded in 200 µL of cell culture medium (DMEM plus 10% FBS, with 200 µg/mL hygromycin) in 96-well flat-bottom plates and the plate is immediately swirled to ensure proper dispersal of cells and the formation of an even monolayer of cells. Cells are allowed to attach for 6 hours. Test compounds are serially diluted 3.16-fold in 100% DMSO to generate a 7-point concentration curve. A solution of test compound (1 µL, 200× in DMSO) is added to each cell-containing well and the plate is incubated for 24 hours in a cell culture incubator (37° C., 5% $CO_2$, 100% relative humidity). 2 replicates are prepared for each test compound concentration. The cells are then lysed in the Cells-To-Ct lysis buffer and the lysate is stored at −80° C.

Full length SMN2-A minigene and GAPDH mRNA are quantified using the primers and probes referenced in WO2014/209841A2 on page 80 in Table 1. Primer SMN Forward A (SEQ ID NO.1) hybridizes to a nucleotide sequence in exon 7 (nucleotide 22 to nucleotide 40), primer SMN Reverse A (SEQ ID NO.2) hybridizes to a nucleotide sequence in the coding sequence of Firefly luciferase, SMN Probe A (SEQ ID NO.3) hybridizes to a nucleotide sequence in exon 7 (nucleotide 50 to nucleotide 54) and exon 8 (nucleotide 1 to nucleotide 21). The combination of these three oligonucleotides detects only SMN1 or SMN2 minigenes (RT-qPCR) and will not detect endogenous SMN1 or SMN2 genes.

The SMN forward and reverse primers are used at final concentrations of 0.4 µM. The SMN probe is used at a final concentration of 0.15 µM. The GAPDH primers are used at final concentrations of 0.2 µM and the probe at 0.15 µM.

The SMN2-minigene GAPDH mix (15 µL total volume) is prepared by combining 7.5 µL of 2×RT-PCR buffer, 0.4 µL of 25×RT-PCR enzyme mix, 0.75 µL of 20×GAPDH primer-probe mix, 4.0075 µL of water, 2 µL of 10-fold diluted cell lysate, 0.06 µL of 100 µM SMN forward primer, 0.06 µL of 100 µM SMN reverse primer, and 0.225 µL of 100 µM SMN probe.

PCR is carried out at the following temperatures for the indicated time: Step 1: 48° C. (15 min); Step 2: 95° C. (10 min); Step 3: 95° C. (15 sec); Step 4: 60° C. (1 min); then repeat Steps 3 and 4 for a total of 40 cycles.

Each reaction mixture contains both SMN2-A minigene and GAPDH primers/probe sets (multiplex design), allowing simultaneous measurement of the levels of two transcripts.

The increase in the abundance of the FL SMN2mini mRNA relative to that in cells treated with vehicle control is determined from real-time PCR data using a modified ΔΔCt method (as described in Livak and Schmittgen, *Methods*, 2001, 25:402-8). The amplification efficiency E is calculated from the slope of the amplification curve for FL SMN2mini and GAPDH individually. The abundance of FL SMN2mini and GAPDH mRNA are then calculated as $(1+E)^{-Ct}$, where Ct is the threshold value for each amplicon. The abundance of FL SMN2mini mRNA is normalized to GAPDH mRNA abundance. The normalized FL SMN2mini mRNA abundance from test compound-treated samples is then divided by normalized FL SMN2mini mRNA abundance from vehicle-treated cells to determine the level of FL SMN2mini mRNA relative to vehicle control.

Table 2 provides $EC_{1.5x}$ concentrations for production of full length SMN2 minigene mRNA that was obtained from the 7-point concentration data generated according to the above procedure for particular compounds of the present invention.

Particular compounds of the present invention exhibit an $EC_{1.5x}$ concentration for production of full length SMN2 minigene mRNA≤1 μM.

More particular compounds of the present invention exhibit an $EC_{1.5x}$ concentration for production of full length SMN2 minigene mRNA≤0.1 μM.

Most particular compounds of the present invention exhibit an EC1.5× concentration for production of full length SMN2 minigene mRNA≤0.02 μM.

TABLE 2

$EC_{1.5x}$ concentrations for production of full length SMN2 minigene mRNA.

| Example | $EC_{1.5x}$ minigene (nM) |
| --- | --- |
| 1 | 3.5 |
| 2 | 3.8 |
| 3 | 3.2 |
| 4 | 1.8 |
| 5 | 0.6 |
| 6 | 2.8 |
| 7 | 3.7 |
| 8 | 0.3 |
| 9 | 0.1 |
| 10 | 6.4 |
| 11 | 1.4 |
| 12 | 1.2 |
| 13 | 5 |
| 14 | 4.1 |
| 15 | 4 |
| 16 | 1.1 |
| 17 | 6.4 |
| 18 | 3.6 |
| 19 | 10.2 |
| 20 | 4.3 |
| 21 | 9.6 |
| 22 | 0.9 |
| 23 | 3.4 |
| 24 | 0.4 |
| 25 | 0.5 |
| 26 | 327 |
| 27 | 39.9 |
| 28 | 5 |
| 29 | 0.3 |
| 30 | 3 |

TABLE 2-continued $EC_{1.5x}$ concentrations for production of full length SMN2 minigene mRNA.

| Example | $EC_{1.5x}$ minigene (nM) |
| --- | --- |
| 31 | 6.7 |
| 32 | 1.6 |
| 33 | 0.5 |
| 34 | 0.9 |
| 35 | 4.7 |
| 36 | 5 |
| 37 | 4.4 |
| 38 | 0.3 |
| 39 | 0.9 |

Example 41

SMN Protein Assay in Cultured Cells

The SMN HTRF (homogeneous time resolved fluorescence) assay is used to quantify the level of SMN protein in SMA patient fibroblast cells treated with test compounds. Materials used and respective sources are listed below in Table 3.

TABLE 3

Materials and their respective sources used in the SMN protein assay in cultured cells.

| Material | Source |
| --- | --- |
| SMA Type 1 human cells | GM03813 (Coriell Institute) |
| Protease inhibitor cocktail | Roche Applied Science Catalog No. 11836145001 |
| Anti-SMN d2 | Blue cap Cisbio Catalog No. 63IDC002-SMN |
| Anti-SMN kryptate | Red cap Cisbio Catalog No. 63IDC002-SMN |
| SMN reconstitution buffer | Cisbio Catalog No. 63IDC002-SMN-Buffer |
| DMEM | Life Technologies (formerly Invitrogen) Catalog No. 11960-044 |
| RIPA Lysis Buffer | 20 mM Tris-HCl pH 7.5, 150 mM NaCl, 1 mM EDTA, 1% Thermo Scientific NP-40 Surfact-Amps Detergent Solution (Fisher Scientific, Pittsburgh/PA), 1% Sodium deoxycholate |
| Diluent Buffer | 20 mM Tris-HCl pH 7.5, 150 mM NaCl |
| Envision Plate Reader | Perkin Elmer Model # 2103 |

Cells are thawed and cultured in DMEM-10% FBS for 72 hours. Cells are trypsinized, counted and re-suspended to a concentration of 25,000 cells/mL in DMEM-10% FBS. The cell suspensions are plated at 5,000 cells per well in a 96 well microtiter plate and incubated for 3 to 5 hours. Test compounds are serially diluted 3.16-fold in 100% DMSO to generate a 7-point concentration curve. 1 μL of test compound solution is transferred to cell-containing wells and cells are incubated for 48 hours in a cell culture incubator (37° C., 5% $CO_2$, 100% relative humidity). Triplicate samples are set up for each test compound concentration. After 48 hours, the supernatant is removed from the wells and 25 μL of the RIPA lysis buffer, containing protease inhibitors, is added to the wells and incubated with shaking at room temperature for 1 hour. 25 μL of the diluent is added and then 35 μL of the resulting lysate is transferred to a 384-well plate, where each well contains 5 μL of the antibody solution (1:100 dilution of anti-SMN d2 and anti-SMN kryptate in SMN reconstitution buffer). The plate is centrifuged for 1 minute to bring the solution to the bottom of the wells, then incubated overnight at room temperature. Fluorescence for each well of the plate at 665 nm and 620 nm is measured on an EnVision multilabel plate reader (Perkin-Elmer).

The normalized fluorescence signal is calculated for each sample, Blank and vehicle control well by dividing the signal at 665 nm by the signal at 620 nm. Normalizing the signal accounts for possible fluorescence quenching due to the matrix effect of the lysate. The ΔF value (a measurement of SMN protein abundance as a percent value) for each sample well is calculated by subtracting the normalized average fluorescence for the Blank control wells from the normalized fluorescence for each sample well, then dividing this difference by the normalized average fluorescence for the Blank control wells and multiplying the resulting value by 100. The ΔF value for each sample well represents the SMN protein abundance from test compound-treated samples. The ΔF value for each sample well is divided by the ΔF value for the vehicle control wells to calculate the fold increase in SMN protein abundance relative to the vehicle control. Table 4 provides $EC_{1.5x}$ concentrations for SMN protein expression that was obtained from the 7-point concentration data generated according to the above procedure for particular compounds of the present invention.

Particular compounds of the present invention exhibit an $EC_{1.5x}$ concentration for SMN protein expression ≤1 μM.

More particular compounds of the present invention exhibit an $EC_{1.5x}$ concentration for SMN protein expression ≤100 nM.

Most particular compounds of the present invention exhibit an $EC_{1.5x}$ concentration for SMN protein expression ≤30 nM.

Table 5 provides the maximum fold increase of SMN protein that was obtained from the 7-point concentration data generated according to the above procedure for particular compounds of the present invention Particular compounds of the present invention exhibit a maximum fold increase >1.5.

More particular compounds of the present invention exhibit a maximum fold increase >1.7.

Most particular compounds of the present invention exhibit a maximum fold increase >1.8.

TABLE 4

$EC_{1.5x}$ concentrations for SMN protein expression.

| Example | EC1.5x SMN protein (nM) |
|---|---|
| 1 | 10.8 |
| 2 | 19.8 |
| 3 | 25.6 |
| 4 | 15.7 |
| 5 | 4.1 |
| 6 | 11 |
| 7 | 15.5 |
| 8 | 5.9 |
| 9 | 2.5 |
| 10 | 22.8 |
| 11 | 7 |
| 12 | 7.5 |
| 13 | 3 |
| 14 | 17.6 |
| 15 | 21.2 |
| 16 | 3 |
| 17 | 20.2 |
| 18 | 25 |
| 19 | 29.8 |
| 20 | 37 |
| 21 | 68.7 |
| 22 | 13.8 |

TABLE 4-continued $EC_{1.5x}$ concentrations for SMN protein expression.

| Example | EC1.5x SMN protein (nM) |
|---|---|
| 23 | 23.9 |
| 24 | 4.7 |
| 25 | 11.9 |
| 26 | 1230 |
| 27 | 126.5 |
| 28 | 49.7 |
| 29 | 2.1 |
| 30 | 13.6 |
| 31 | 27.7 |
| 32 | 4 |
| 33 | 4 |
| 34 | 4.4 |
| 35 | 19.5 |
| 36 | 34.4 |
| 37 | 45 |
| 38 | 3.1 |
| 39 | 15.8 |

TABLE 5

Maximum fold increase of SMN protein.

| Example | max. fold increase |
|---|---|
| 1 | 1.84 |
| 2 | 1.76 |
| 3 | 1.81 |
| 4 | 1.76 |
| 5 | 1.71 |
| 6 | 1.84 |
| 7 | 1.76 |
| 8 | 1.85 |
| 9 | 1.92 |
| 10 | 1.95 |
| 11 | 1.9 |
| 12 | 1.77 |
| 13 | 1.91 |
| 14 | 1.86 |
| 15 | 1.94 |
| 16 | 1.83 |
| 17 | 1.98 |
| 18 | 1.75 |
| 19 | 1.83 |
| 20 | 1.72 |
| 21 | 1.54 |
| 22 | 1.69 |
| 23 | 1.63 |
| 24 | 1.77 |
| 25 | 1.79 |
| 26 | 1.52 |
| 27 | 1.57 |
| 28 | 1.72 |
| 29 | 1.81 |
| 30 | 1.84 |
| 31 | 1.65 |
| 32 | 1.88 |
| 33 | 1.82 |
| 34 | 1.89 |
| 35 | 1.79 |
| 36 | 1.77 |
| 37 | 1.87 |
| 38 | 1.85 |
| 39 | 1.81 |

Example 42

In Vitro Assay of 7-(4,7-diazaspiro[2.5]octan-7-yl)-2-(2,8-dimethylimidazo[1,2-b]pyridazin-6-yl)pyrido[1,2-a]pyrimidin-4-one (Example 20)

The compound of Example 20 is an orally available small molecule SMN2 splicing modifier for the treatment of SMA.

It has been found, that the compound of Example 20 effectively corrects the dysfunctional splicing of the human SMN2 pre-mRNA in cultured patient cells (SMA Type 1 fibroblasts) by shifting the balance of the alternative splicing reaction completely towards the inclusion of SMN2 exon 7 and the production of the full-length mRNA (FIG. 1A: $EC_{50}$ 29±8 nM for FL, 12±1 nM for Δ7 mRNA). Treating cells expressing the SMN2 minigene with increasing concentrations of compound of Example 20 resulted in a dose-dependent increase in the amount of the SMN2 minigene full length mRNA. EC1.5× was 4.7±0.7 nM and the maximum induction was 20-fold. The minigene assay results confirm that compound of Example 20 is a potent SMN2 splicing modifier.

To investigate SMN protein production as a consequence of alternative splicing, an in vitro assay was performed to assess the levels of SMN protein in fibroblasts and in spinal motor neurons derived from SMA patient iPSCs (induced Pluripotent Stem Cells) ($EC_{50}$ of 123 nM, and $EC_{50}$ 182±114 nM, respectively). The maximal increase in SMN protein above untreated cells resulted in levels similar in both cell types (60-80%; FIGS. 1B and 1C), suggesting that in different cell types from SMA patients, compound of Example 20 increases SMN protein level similarly as a result of correcting the dysfunctional SMN2 splicing in vitro.

To further assess SMN2 splicing as a potential blood biomarker, an ex vivo assay was developed using whole blood cells from healthy volunteers in which SMN1 and SMN2 splicing was assessed after 4 hours treatment with the compound of Example 20 (at this time point, maximal splicing changes were achieved). Whereas SMN1 splicing was largely unaffected, SMN2 splicing was dose-dependently altered towards inclusion of exon 7 (FIG. 1D). Effects on splicing were evident at concentrations above 100 nM of compound of Example 20, suggesting that these levels in the blood are required to observe the in vivo pharmacodynamic (PD) effects on SMN2 splicing with this assay.

Example 43

In Vivo Assay of 7-(4,7-diazaspiro[2.5]octan-7-yl)-2-(2,8-dimethylimidazo[1,2-b]pyridazin-6-yl)pyrido[1,2-a]pyrimidin-4-one (Example 20)

In vivo, the compound of Example 20 increases SMN protein in the brain and muscle in the severe SMNΔ7 model and the milder C/C-allele model, carrying human SMN2 transgenes. Adult C/C-allele mice were treated for 10 days with vehicle or the compound of Example 20 (1, 3 or 10 mg/kg PO, daily), and 3 days old (P3) SMNΔ7 mice were treated for 7 days with vehicle or the compound of Example 20 (0.1, 0.3, 1 or 3 mg/kg IP, daily). The compound of Example 20 dose-dependently increased SMN protein levels in brain and muscle tissue, with a maximum effect of a 2-3 fold increase reached at 10 mg/kg in adult C/C-allele mice and at 1-3 mg/kg in neonatal SMNΔ7 mice (FIG. 2). Thus, in the muscle of C/C-allele mice at the 10 mg/kg dose, the SMN levels achieved were no different from those in heterozygous mice. In SMNΔ7 mice, the SMN protein increase was only partial in both brain and muscle, reaching approximately 43% (brain) and 55% (muscle) of protein levels in heterozygous mice. These data demonstrate that the compound of example 20 increases SMN protein in both brain and muscle tissues of transgenic mouse models of SMA.

Functional benefits were assessed in the severe and mild SMA mouse models. SMNΔ7 mice were treated from P3 to P23 once daily by IP injection of vehicle or the compound of Example 20, and from P24 onwards once daily by oral gavage. During the treatment period, body weight and animal survival were monitored. Over the 100-day observation period, only two heterozygous littermates died. In contrast, all vehicle-treated mice died before P21 with a median survival time (MST) of 10.5 days. Example 20 treatment dose-dependently prolonged animal survival (FIG. 3A). A minor but significant prolongation of MST to P26 was observed at a lower dose (0.1 mg/kg IP until P23 and 0.3 mg/kg PO thereafter). The mid- (0.3 mg/kg IP through P23 and 1 mg/kg PO thereafter), mid/high- (1 mg/kg IP through P23 and 3 mg/kg PO thereafter), and high-dose (3 mg/kg IP through P23 and 10 mg/kg PO thereafter) treatment groups resulted in 80%, 82%, and 73% respectively, of animals surviving up to P100, no different from heterozygous littermates with 83% surviving at P100.

Body weight increase of SMNΔ7 mice throughout the study was severely impaired and only mildly corrected by the low dose of the compound of Example 20. Treatment with the mid-, mid/high-, and high-doses of the compound of Example 20 resulted in a 71%, 82%, and 85% respectively, recovery in body weight gain as compared to heterozygous littermates that do not show any SMA-related phenotype (FIG. 3B). These data suggest that treatment with the compound of Example 20 dose-dependently prevents the manifestation of the SMA phenotype in the severely affected SMNΔ7 mice when dosing is started at P3.

Lastly, the compound of Example 20 improves neuromuscular connectivity in a severe SMA mouse model in vivo. SMNΔ7 mice were treated from P3 to P14 by IP application of vehicle or 0.1, 0.3, 1 mg/kg Example 20 once per day. At P14, 1 hour after the last dose spinal cord and muscle tissues were processed for histological assessment. Relative to heterozygous littermates, SMNΔ7 mice showed a significant loss of vesicular glutamate transporter 1 (vGlut1) proprioceptive motor neuron inputs, loss of motor axons, neuromuscular junction (NMJ) denervation in longissimus muscle, and muscle atrophy. Example 20 treatment dose-dependently and significantly increased the number of vGlut1 inputs, the number of motor axons, the percentage of fully innervated NMJs and the fiber size in extensor digitorum longus (EDL) muscles relative to vehicle-treated SMNΔ7 mice (FIG. 4). These data suggest that treatment with the compound of Example 20, when started at P3, protects both central and peripheral aspects of NMJ denervation and protects against muscle atrophy in severely affected SMNΔ7 mice.

Example 44

Transcriptional Profiling Analysis of 7-(4,7-diazaspiro[2.5]octan-7-yl)-2-(2,8-dimethylimidazo[1,2-b]pyridazin-6-yl)pyrido[1,2-a]pyrimidin-4-one (Example 20)

To identify other potential genes alternatively spliced by the compound of Example 20, a transcriptional profiling analysis was performed which revealed that the splicing events of a few genes were also affected at therapeutically relevant concentration of 121 nM ($EC_{90}$, 10-fold higher than $EC_{50}$): STRN3, SLC25A17 and GGCT compared to control. The specific function of STRN3, SLC25A17, and GGCT and consequences of their dysregulation have not been elucidated so far. These three genes are also consistently found to be affected at the higher dose (5-fold higher than the $EC_{90}$), a dose used in order to illustrate the maximum effect of this compound. Splicing events of 11 genes, including the genes FoxM1 and MADD, were affected at the higher dose but not by the lower dose. FoxM1 and MADD have been described as being involved in cell cycle regulation and apoptosis, respectively. A recent report on SMN2 splicing modifiers, suggests that the compound of Example 20 is relatively specific compared with another molecule, NVS-SM1, for which there were 39 candidate events where splicing changed in response to treatment [Palacino et al, Nat Chem Biol. 2015 July; 11(7):511-7].

In addition, the transcriptional profiling analysis demonstrated that the expression levels of 0 genes were changed ($p<0.01$) upon treatment with the compound of Example 20 at the 121 nM dose. These data demonstrate the relative specificity of the compound compared with published data on the expression level changes of another alternative SMN2 splicing molecule, NVS-SM1, in which there were 175 genes changed at greater than ±2-fold ($p<0.05$), and NVS-SM3 which significantly altered 23 genes [Palacino et al, Nat Chem Biol. 2015 July; 11(7):511-7].

FoxM1, a gene alternatively spliced by other splicing modifier compounds, encodes a cell cycle regulator. In humans and higher primates only, the transcriptionally inactive FoxM1a variant contains exon 9 (FL) and the transcriptionally active FoxM1b/c variants lack exon 9 (Δ9) [Ye et al, Future Oncol. 2007 February; 3(1):1-3. Laoukili et al, Biochim Biophys Acta. 2007 January; 1775(1):92-102]. Using RT qPCR with specific primers for FoxM1a (FL), and FoxM1b/c (Δ9), the modification of alternative splicing of FoxM1 after Example 20 treatment was confirmed ($EC_{50}$ 67±32 nM for FL, 139±43 nM for Δ9 mRNA; see FIG. 5). Increased expression of the FoxM1A isoform, together with decreased expression of FoxM1 isoforms lacking exon 9, has the capability to disturb and inhibit cell cycle progression if splicing changes are at a level that is biologically significant. Thus, the compound of Example 20 acts in a similar way on the SMN2 and FoxM1 splicing machinery, but with opposing outcomes with regard to protein function and at varying degrees. The $EC_{50}$ for MADD, a gene also identified as affected by splicing modifiers including the compound of Example 20 at high concentrations and known to be involved in apoptotic processes, is not known.

Example 46

Pharmaceutical Compositions Comprising Olesoxime

Examples of compositions comprising olexosime are described in US2010099652A1. Olesoxime is stable in the solid state (>36 months at 25° C./60% RH), exhibiting no change in purity profile under long-term and accelerated stress conditions. Olesoxime has low aqueous solubility (less than 5 μg/ml) across the physiological pH range. It is freely soluble or soluble in a range of non-aqueous solvents.

In order to provide an age-appropriate formulation for a wide age range, an oral liquid composition has been developed. It has been found that a particularly beneficial pharmaceutical composition can be achieved by preparing an oral or gastric suspension of olexosime powder in sesame oil due to superior stability performance. Olesoxime solubility in sesame oil (approximately 35 mg/ml) is insufficient to enable the preparation of a solution while limiting the amounts of oil absorbed by the subject. Palatability (taste, smell and texture) is acceptable without further excipients.

7.5 g crystalline olesoxime powder (particle size distribution with d90 value 70-90 μm) was suspended in 75 ml (61.6 g) sesame oil (refined) as vehicle through agitation (e.g. shaking) to yield a homogeneous suspension (final olesoxime concentration 100 mg/ml). Such oral suspension has been found to be stable for at least 3 months at 25° C./60% RH regarding degradation, appearance, color, content uniformity and microbial limits.

Example 45

Oral solutions comprising 7-(4,7-diazaspiro[2.5] octan-7-yl)-2-(2,8-dimethylimidazo[1,2-b]pyridazin-6-yl)pyrido[1,2-a]pyrimidin-4-one 7-(4,7-diazaspiro[2.5]octan-7-yl)-2-(2,8-dimethylimidazo[1,2-b]pyridazin-6-yl)pyrido[1,2-a]pyrimidin-4-one, the compound of Example 20, can be formulated as oral aqueous solution by dissolving the drug substance in a buffer system at pH of less than pH4, particularly pH 3.4, in order to provide sufficiently high drug concentration, e.g. citric buffer, malate, maleate, or tartrate buffer, more particularly malate or tartrate, most particularly tartrate buffer.

Long term stability of formulations of the compound of Example 20 by preparing a dry powder or granulation for constitution of an oral solution. Buffer system can be incorporated into dry formulation by the selection of organic acid and salts thereof as fine crystalline powders, e.g. tribasic sodium citrate dihydrate and citric acid anhydrous, sodium malate and malic acid, or preferably potassium sodium tartrate and tartaric acid.

Powders or granules comprising the compound of Example 20 may comprise a extragranular filler, such as sorbitol, isomalt, or mannitol, and combinations thereof, which ensure fast dissolution of the powder blend during constitution of the oral solution. In introduction of a diluent the powder blend can be granulated by dry compaction in order to improve the flowability and to ensure robust uniformity.

Ingredients for the constitution of a solvent system for the compound of Example 20 can be formulated as separate formulation. The constituted solvent can be used for dissolution of the compound of Example 20 in a bottle at the start of the in-use period of the oral solution.

The constituted oral solution of the compound of Example 20 in a buffer can be can provide in-use times of more than 2 weeks by the use of stabilizers and antioxidants, such as vitamin E TPGS, disodium edetate, butyl hydroxyl toluol, riboflavin, or preferably ascorbic acid, and in combinations thereof.

Table 6 provides a number of oral solutions providing stability in solution of more than 2 weeks.

TABLE 6

Oral solutions of 7-(4,7-diazaspiro[2.5]octan-7-yl)-2-(2,8-dimethylimidazo[1,2-b]pyridazin-6-yl)pyrido[1,2-a]pyrimidin-4-one at concentration of 0.1 mg/ml, 1.0 mg/ml and 3.0 mg/ml.

| Ingredients | Composition 1A 0.1 mg/ml (mg) | Composition 1B 1.0 mg/ml (mg) | Composition 1C 3.0 mg/ml (mg) | Composition 1D 1.0 mg/ml (mg) |
|---|---|---|---|---|
| 7-(4,7-diazaspiro[2.5]octan-7-yl)-2-(2,8-dimethylimidazo[1,2-b]pyridazin-6-yl)pyrido[1,2-a]pyrimidin-4-one | 20.0 | 200.0 | 600.0 | 200 |
| citric acid anhydrous | 1077.2 | 1077.2 | 1921.2 | — |
| sodium citrate dihydrate | 115.6 | 115.6 | 0.0 | — |
| Tartaric Acid anhydrous | — | — | — | 1274.0 |
| Potassium Sodium Tartrate x4H$_2$O | — | — | — | 347.6 |
| ascorbic acid | 70.5 | 70.5 | 211.5 | 70.5 |
| disodium edetate | 33.6 | 33.6 | 100.8 | 33.6 |
| water for injection | ad 200.0 ml | ad 200.0 ml | ad 200.0 ml | ad 200.0 ml |

Example 46

Powder Blends as Vehicles for Constitution of Oral Solutions of 7-(4,7-diazaspiro[2.5]octan-7-yl)-2-(2,8-dimethylimidazo[1,2-b]pyridazin-6-yl)pyrido[1,2-a]pyrimidin-4-one Table 7 represents a granulated powder blend for the constitution of a solvent, which is suitable to dissolve 7-(4,7-diazaspiro[2.5]octan-7-yl)-2-(2,8-dimethylimidazo[1,2-b]pyridazin-6-yl)pyrido[1,2-a]pyrimidin-4-one, and to obtain an oral solution at pH3.5 which is stable for more than 2 weeks. The blend contains polyethylene glycol 6000 as water soluble lubricant, sodium benzoate as preservative, sucralose as sweetener, and strawberry flavor for the purpose of improving the taste, particularly for use in pediatric patients.

The compositions of Table 7 together with 80 ml water provide constitution solvents suitable for the dissolution of 7-(4,7-diazaspiro[2.5]octan-7-yl)-2-(2,8-dimethylimidazo[1,2-b]pyridazin-6-yl)pyrido[1,2-a]pyrimidin-4-one (80 mg, 240 mg and 400 mg respectively).

TABLE 7

Powder blend of a vehicle for constitution of an oral solution of 7-(4,7-diazaspiro[2.5]octan-7-yl)-2-(2,8-dimethylimidazo[1,2-b]pyridazin-6-yl)pyrido[1,2-a]pyrimidin-4-one at pH 3.4 with API concentrations of 1.0, 3.0 and 5.0 mg/ml.

| Dedicated to concentration of 7-(4,7-diazaspiro[2.5]octan-7-yl)-2-(2,8-dimethylimidazo[1,2-b]pyridazin-6-yl)pyrido[1,2-a]pyrimidin-4-one in solution: | Composition 2A 1 mg/ml (mg) | Composition 2B 3 mg/ml (mg) | Composition 2C 5 mg/ml (mg) |
|---|---|---|---|
| intragranular: | | | |
| Mannitol | 1'525.78 | 1'554.58 | 1'566.58 |
| Tartaric Acid | 148.00 | 180.00 | 194.00 |
| Potassium Sodium Tartrate *4H$_2$O | 173.60 | 112.80 | 86.80 |
| Sodium Benzoate micronized | 80.00 | 80.00 | 80.00 |
| Ascorbic Acid fine powder | 28.18 | 28.18 | 28.18 |
| Disodium Edetate | 13.44 | 13.44 | 13.44 |
| PEG 6000 | 25.00 | 25.00 | 25.00 |
| Sucralose | 16.00 | 16.00 | 16.00 |
| Total intragranular: | 2'010.0 | 2'010.0 | 2'010.0 |
| extragranular: | | | |
| Mannitol 160C | 250.00 | 250.00 | 250.00 |
| Strawberry flavor | 240.00 | 240.00 | 240.00 |
| Total: | 2'500.0 | 2'500.0 | 2'500.0 |

Example 47

Powder blends comprising 7-(4,7-diazaspiro[2.5]octan-7-yl)-2-(2,8-dimethylimidazo[1,2-b]pyridazin-6-yl)pyrido[1,2-a]pyrimidin-4-one for constitution of oral solutions Table 8 represents an oral solutions comprising 7-(4,7-diazaspiro[2.5]octan-7-yl)-2-(2,8-dimethylimidazo[1,2-b]pyridazin-6-yl)pyrido[1,2-a]pyrimidin-4-one which have been constituted by the use of constituted vehicle solution from example 46 for the dissolution of the active compound. The vehicle is suitable for constitution of an oral solution at pH3.4 which is stable for more than 2 weeks. The compositions of Table 8 together with 80 m water provide oral solutions comprising 1 mg/ml, 3 mg/ml resp. 5 mg/ml of 7-(4,7-diazaspiro[2.5]octan-7-yl)-2-(2,8-dimethylimidazo[1,2-b]pyridazin-6-yl)pyrido[1,2-a]pyrimidin-4-one.

TABLE 8

Oral solution constitution of an oral solution comprising 7-(4,7-diazaspiro[2.5]octan-7-yl)-2-(2,8-dimethylimidazo[1,2-b]pyridazin-6-yl)pyrido[1,2-a]pyrimidin-4-one at pH 3.5 with API concentrations of 1.0, 3.0 and 5.0 mg/ml.

|  | Composition 2A 1 mg/ml (mg) | Composition 2B 3 mg/ml (mg) | Composition 2C 5 mg/ml (mg) |
|---|---|---|---|
| 7-(4,7-diazaspiro[2.5]octan-7-yl)-2-(2,8-dimethylimidazo[1,2-b]pyridazin-6-yl)pyrido[1,2-a]pyrimidin-4-one | 80 | 240 | 400 |
| Mannitol | 1'525.78 | 1'554.58 | 1'566.58 |
| Tartaric Acid | 148.00 | 180.00 | 194.00 |
| Potassium Sodium Tartrate *4H$_2$O | 173.60 | 112.80 | 86.80 |
| Sodium Benzoate micronized | 80.00 | 80.00 | 80.00 |
| Ascorbic Acid fine powder | 28.18 | 28.18 | 28.18 |
| Disodium Edetate | 13.44 | 13.44 | 13.44 |
| PEG 6000 | 25.00 | 25.00 | 25.00 |
| Sucralose | 16.00 | 16.00 | 16.00 |
| Mannitol 160C | 250.00 | 250.00 | 250.00 |
| Strawberry flavor | 240.00 | 240.00 | 240.00 |
| Water | ad 80 ml | ad 80 ml | ad 80 ml |
| Total: | 80 ml | 80 ml | 80 ml |

Example 48

Powder blends of 7-(4,7-diazaspiro[2.5]octan-7-yl)-2-(2,8-dimethylimidazo[1,2-b]pyridazin-6-yl)pyrido[1,2-a]pyrimidin-4-one for constitution of oral solutions Table 9 provides powder blends comprising 7-(4,7-diazaspiro[2.5]octan-7-yl)-2-(2,8-dimethylimidazo[1,2-b]pyridazin-6-yl)pyrido[1,2-a]pyrimidin-4-one which may be used to constitute oral solutions together with 90 m water. The compositions of Table 9 may also be constituted from solvent prepared from a vehicle powder blend (similar to example 46) followed by dissolution of API.

TABLE 9

Oral solutions of 7-(4,7-diazaspiro[2.5]octan-7-yl)-2-(2,8-dimethylimidazo[1,2-b]pyridazin-6-yl)pyrido[1,2-a]pyrimidin-4-one at concentration of 1.0 mg/ml in a bottle containing 90 ml.

|  | Composition 3A (mg) | Composition 3B (mg) |
|---|---|---|
| 7-(4,7-diazaspiro[2.5]octan-7-yl)-2-(2,8-dimethylimidazo[1,2-b]pyridazin-6-yl)pyrido[1,2-a]pyrimidin-4-one | 90.0 | 90.0 |
| Mannitol | 1200.0 | 1200.0 |
| Maltodextrin | — | 450.0 |
| Lactose | 450.0 | — |
| D-L tartaric acid | 573.3 | 573.3 |
| Disodium tartrate dihydrate | 156.4 | 156.4 |
| Ascorbic acid | 31.7 | 31.7 |
| Disodium edetate * 4H$_2$O | 15.1 | 15.1 |
| Sucralose | 18.0 | — |
| Sodium saccharin | — | 18.0 |
| Sodium benzoate | 90.0 | — |
| Sorbic acid | — | 90.0 |
| PEG 6000 | 18.0 | — |
| Strawberry flavor | 180.0 | — |
| Vanilla flavor | — | 180.0 |
| Total per bottle (mg): | 2822.5 | 2804.5 |

Example 49

Powder Blends of 7-(4,7-diazaspiro[2.5]octan-7-yl)-2-(2,8-dimethylimidazo[1,2-b]pyridazin-6-yl)pyrido[1,2-a]pyrimidin-4-one for constitution of oral solutions Table 10 provides powder blends comprising 7-(4,7-diazaspiro[2.5]octan-7-yl)-2-(2,8-dimethylimidazo[1,2-b]pyridazin-6-yl)pyrido[1,2-a]pyrimidin-4-one which may be used to constitute oral solutions together with 80 m 1 water.

The compositions of Table 10 may also be constituted from solvent prepared from vehicle powder blend (similar to example 46) followed by dissolution of API.

TABLE 10

Powder blend for the preparation of an oral solution of 7-(4,7-diazaspiro[2.5]octan-7-yl)-2-(2,8-dimethylimidazo[1,2-b]pyridazin-6-yl)pyrido[1,2-a]pyrimidin-4-one at concentration of 1 mg/ml in a bottle containing 80 ml water.

|  | Quantity per bottle (mg) | percentage solids (%) |
|---|---|---|
| intragranular: |  |  |
| 7-(4,7-diazaspiro[2.5]octan-7-yl)-2-(2,8-dimethylimidazo[1,2-b]pyridazin-6-yl)pyrido[1,2-a]pyrimidin-4-one | 80.00 | 3.20 |
| Mannitol (Parteck M100) | 1445.94 | 57.84 |
| D-L tartaric acid | 147.68 | 5.91 |
| Potassium sodium tartrate | 173.76 | 6.95 |
| Sodium benzoate | 80.00 | 3.20 |
| Ascorbic acid | 28.18 | 1.13 |
| Disodium edetate | 13.44 | 0.54 |
| Sucralose | 16.00 | 0.64 |
| PEG 6000 | 25.00 | 1.00 |
| Total Dry: | 2010.00 | 80.40 |
| extragranular: |  |  |
| Strawberry flavor PHS-180152 | 240.00 | 10.00 |
| Mannitol 160C | 250.00 | 9.60 |
| Total per bottle (mg): | 2500.00 | 100.00 |

Example 50

Stability of Oral Solutions of 7-(4,7-diazaspiro[2.5]octan-7-yl)-2-(2,8-dimethylimidazo[1,2-b]pyridazin-6-yl)pyrido[1,2-a]pyrimidin-4-one Table 11 provides a comparison of the stabilities of various solutions of 7-(4,7-diazaspiro[2.5]octan-7-yl)-2-(2,8-dimethylimidazo[1,2-b]pyridazin-6-yl)pyrido[1,2-a]pyrimidin-4-one, expressed as API purity in percent. The API has been found to be stable in all oral solutions investigated without remarkable degradation over several weeks at ambient temperature as well at 5° C.

Composition 1A of Example 45 comprises 0.1 mg/ml of API in a citrate buffer system together with ascorbic acid as antioxidant and disodium edetate as stabilizer.

Composition 2A of Example 46 was constituted with 200 ml of water to dissolve 200 mg of API (1 mg/ml).

Compositions 3A and 3B of Example 48 were constituted from API powder blend together with 90 ml of water (1 mg/ml).

TABLE 11

Stability of solution of various compositions stored at 5° C. or 25° C. in amber glass bottles.

| | Purity of 7-(4,7-diazaspiro[2.5]octan-7-yl)-2-(2,8-dimethylimidazo[1,2-b]pyridazin-6-yl)pyrido[1,2-a]pyrimidin-4-one (%) | | | |
|---|---|---|---|---|
| Composition | initial | after 7 days at 25° C. | after 17 days at 5° C. | after 17 days at 25° C. |
| 1A | 99.29 | 99.17 | 99.26 | — |
| 2A | 99.33 | 99.23 | 99.29 | — |
| 3A | 99.32 | 99.20 | 99.29 | — |
| 3A | 99.34 | — | — | 99.28 |
| 3B | 99.33 | — | — | 99.21 |

Example 51

Water-in-Oil Emulsions Comprising 7-(4,7-diazaspiro[2.5]octan-7-yl)-2-(2,8-dimethylimidazo[1,2-b]pyridazin-6-yl)pyrido[1,2-a]pyrimidin-4-one and olesoxime For a combined dosing of the compound of Example 20 together with olesoxime with one single composition the aqueous oral solutions of the compound of Example 20 can be combined with an oily solution of olesoxime by the constitution of an oral suspension. An oily solution of olesoxime (as e.g. in Example 46) can be transferred into a bottle containing the constituted solution of the compound of Example 20 and subsequently an emulsion can be formed by manually shaking the closed bottles for 5-20 times, preferably 10 times. The oily solution of olesoxime is a solution in sesame oil which may contain emulsifying and/or lipophilic solubilizing agents such as glyceryl mono-oleate (Peceol™, Inwitor 948™, Capmul GMO™) glyceryl mono-linoleate (Maisine 35-1™), sorbitan mono-oleate (Span 80™), or oleic acid, to increase the solubility of olesoxime in the oily solvent and to enable the formation of an emulsion from the oily solution when it will be combined with the solutions of the compound of Example 20. Emulsifiers and solubilizing agents which are dispersed in the oily solvent, optionally prior to dissolution of olesoxime with the application of heat, can be combined with more polar surfactants with a HLB value of less than 7, e.g. polysorbate 80 (Tween 80™) caprylocaproyl polyoxyl glycerides (Labrasol™) in order to provide an emulsion of higher dispersibility and longer physical stability after constitution. The emulsion can have either the aqueous phase or the oily phase as dispersed inner phase in dependence of the selected ratio between the lipophilic surfactant with low HLB and the more hydrophilic surfactant with high HLB value.

Table 12 provides 2 examples for an oily vehicle which is suitable for the formation of an water-in-oil emulsion, comprising 7-(4,7-diazaspiro[2.5]octan-7-yl)-2-(2,8-dimethylimidazo[1,2-b]pyridazin-6-yl)pyrido[1,2-a]pyrimidin-4-one in the aqueous phase and olesoxime in the lipidic phase.

TABLE 12

Oily vehicles for Olesoxime to constitute a water-in-oil emulsion with 7-(4,7-diazaspiro[2.5]octan-7-yl)-2-(2,8-dimethylimidazo[1,2-b]pyridazin-6-yl)pyrido[1,2-a]pyrimidin-4-one oral solution.

| Ingredients | Composition 4A (%) | Composition 4F (%) |
|---|---|---|
| Sesame oil | 90.0 | 90.0 |
| Sorbitan monooleate | 7.0 | |
| Peceol ™ (Glyceryl monooleate) | | 6.1 |
| Polysorbate 80 | 3.0 | |
| Labrasol ™ (caprylocaproyl polyoxyl gliceriges) | | 3.9 |

With composition 4A and 4F up to 30% (w/w) aqueous tartrate buffer solution pH3.3 could be dispersed as emulsion after 10 times shaking. The emulsions were visually homogeneous for at least 15 minutes.

Table 3 (Composition 5A) represents a solution used for preparing an aqueous solution of 7-(4,7-diazaspiro[2.5]octan-7-yl)-2-(2,8-dimethylimidazo[1,2-b]pyridazin-6-yl)pyrido[1,2-a]pyrimidin-4-one.

TABLE 13

Aqueous solvent for 7-(4,7-diazaspiro[2.5]octan-7-yl)-2-(2,8-dimethylimidazo[1,2-b]pyridazin-6-yl)pyrido[1,2-a]pyrimidin-4-one. Composition 5A

| Ingredients: | mg |
|---|---|
| Tartaric Acid | 184.6 |
| Potassium Sodium Tartrate x4H2O | 217.2 |
| Ascorbic Acid | 35.23 |
| Disodium Edetate anhydrous | 16.81 |
| Purified water | Ad 100 ml |

FIG. 6 provides photographs of composition 4A prior to (A) and immediately after the addition of 20% (B) or 30% (C) of tartrate buffer solution (composition 5A) and thereby resulting water-in-oil emulsions.

FIG. 7 provides photographs of water-in-oil emulsions comprising 70% composition 4A and 30% composition 5A 15 minutes after constitution (A) (10 times shaking) and 30 min after constitution (B) (10 times shaking).

FIG. 8 provides photographs of composition 4F prior to (A) and immediately after the addition of 20% (B left), 25% (B middle) or 30% (B right) of tartrate buffer solution (composition 5A) and thereby resulting water-in-oil emulsions.

FIG. 9 provides photographs of water-in-oil emulsions comprising 70% composition 4F and 30% composition 5A 15 minutes after constitution (A) (10 times shaking) and 30 min after constitution (B) (10 times shaking).

All emulsions prepared were stable for at least 30 minutes.

Example 52

Oily Solutions Comprising 7-(4,7-diazaspiro[2.5]octan-7-yl)-2-(2,8-dimethylimidazo[1,2-b]pyridazin-6-yl)pyrido[1,2-a]pyrimidin-4-one and olesoxime Alternatively to emulsions, co-formulations of the compound of Example 20 and olesoxime can be prepared by dissolving both drug substances in an oily solvent containing sesame oil and lipophilic surfactants, such as glyceryl mono-oleate (Peceol™, Inwitor 948™ Capmul GMO™), glyceryl mono-linoleate (Maisine 35-1™), sorbitan mono-oleate (Span 80™) or oleic acid, to enable improved solubility in the solvent.

Table 14 provides an oily solvent system which provides increased solubility for both drugs and leads to sufficient stability for an in-use time after constitution as shown in Table 15.

TABLE 14

Oily solution of 100 mg/ml Olesoxime and 10 mg/ml 7-(4,7-diazaspiro[2.5]octan-7-yl)-2-(2,8-dimethylimidazo[1,2-b]pyridazin-6-yl)pyrido[1,2-a]pyrimidin-4-one.

| Ingredients | Composition 6A | Composition 6B |
|---|---|---|
| 7-(4,7-diazaspiro[2.5]octan-7-yl)-2-(2,8-dimethylimidazo[1,2-b]pyridazin-6-yl)pyrido[1,2-a]pyrimidin-4-one | 10.0 mg | 10.0 mg |
| Olesoxime | 100.0 mg | 100.0 mg |
| Butyl hydroxanisol | 18.9 mg (0.02% w/w) | — |
| Vitamin E | — | 236.25 mg (0.25% w/w) |
| Oleic acid | 9.45 g (10% w/w) | 9.45 g (10% w/w) |
| Maisine ™ Glyceryl Monolinoleate | ad 100.0 ml | ad 100.0 ml |

TABLE 15

Stability of oily solution compositions 6A and 6B.

| Composition | initial | after 1 day at room temperature | after 7 days at 4° C. | after 7 days at room temperature |
|---|---|---|---|---|
| Content 7-(4,7-diazaspiro[2.5]octan-7-yl)-2-(2,8-dimethylimidazo[1,2-b]pyridazin-6-yl)pyrido[1,2-a]pyrimidin-4-one (%) | | | | |
| 6A | 99.5 | 97.0 | 99.0 | 96.5 |
| 6B | 99.5 | 95.4 | 98.7 | 96.3 |
| Content Olesoxime (%) | | | | |
| 6A | 98 | 98 | 98 | 98 |
| 6B | 98 | 98 | 98 | 97 |

Example 53

Powder Blends of Vehicles and Stability of Oral Solutions Constituted Therefrom Table 16 provides dry granulated powder blends of vehicles suitable for constitution of oral solutions comprising 7-(4,7-diazaspiro[2.5]octan-7-yl)-2-(2,8-dimethylimidazo[1,2-b]pyridazin-6-yl)pyrido[1,2-a]pyrimidin-4-one (e.g. 0.25 or 1.5 mg/ml) at pH3.4.

In these compositions the exact amount of tartaric acid required to reach the target pH has been used instead of buffer consisting of the acid and the corresponding salt. In-use stability of the solution for at least 17 days could be demonstrated as can be seen from Table 17.

TABLE 16

Dry granulated powder blends of vehicles for constitution.

| Ingredients | Composition 7a (Vehicle for 0.25 mg/ml; mg per bottle) | Composition 7b (Vehicle for 1.5 mg/ml; mg per bottle) |
| --- | --- | --- |
| Mannitol | 2019.93 | 1948.63 |
| Tartaric acid | 92.00 | 163.30 |
| Sodium benzoate | 64.00 | 64.00 |
| Ascorbic acid | 28.18 | 28.18 |
| Polyethylene glycol 6000 | 25.00 | 25.00 |
| disodium edetate | 14.89 | 14.89 |
| sucralose | 16.00 | 16.00 |
| Strawberry flavor | 240.00 | 240.00 |
| total per bottle (mg) | 2500.0 | 2500.0 |

TABLE 17

Stabilities of oral solutions comprising circa 0.25 mg/ml or circa 1.5 mg/ml of 7-(4,7-diazaspiro[2.5]octan-7-yl)-2-(2,8-dimethylimidazo[1,2-b]pyridazin-6-yl)pyrido[1,2-a]pyrimidin-4-one (indicated as API in the table) in vehicle solution of Composition 7a or 7b constituted with 80 ml water for injection.

| | | 5° C. | | 25° C. | |
| --- | --- | --- | --- | --- | --- |
| days | Vehicle Composition | API content [mg/ml] | API Purity [%] | API content [mg/ml] | API Purity [%] |
| 0 | 7a | 0.24 | 99.56 | 0.24 | 99.56 |
| 10 | | 0.24 | 99.57 | 0.24 | 99.55 |
| 17 | | 0.24 | 99.60 | 0.24 | 99.50 |
| 0 | 7b | 1.42 | 99.56 | 1.43 | 99.54 |
| 10 | | 1.45 | 99.57 | 1.43 | 99.56 |
| 17 | | 1.45 | 99.50 | 1.45 | 99.50 |

Example 54

Powder blends of 7-(4,7-diazaspiro[2.5]octan-7-yl)-2-(2,8-dimethylimidazo[1,2-b]pyridazin-6-yl)pyrido[1,2-a]pyrimidin-4-one and stability of oral solutions constituted therefrom The dry granulated powder blends of Composition 8a, 8b, 8c and 8d of Table 18 already include the API in order to simplify the constitution procedure for the solution. Compositions 8a to 8d exhibit reduced powder fill weight and contain isomalt as second diluent in order to improve the granule properties. Excellent stability up to one month in solution could be demonstrated with both—water for injection and potable water—as can be seen from Table 19.

TABLE 18

Dry granulated powder blends for constitution of oral solutions of 7-(4,7-diazaspiro[2.5]octan-7-yl)-2-(2,8-dimethylimidazo[1,2-b]pyridazin-6-yl)pyrido[1,2-a]pyrimidin-4-one (0.25 mg/ml or 0.75 mg/ml) constituted with 80 ml water for injection at pH 3.4.

| Ingredients | Composition 8a | Composition 8b | Composition 8c | Composition 8d |
| --- | --- | --- | --- | --- |
| | mg per bottle | | | |
| 7-(4,7-diazaspiro[2.5]octan-7-yl)-2-(2,8-dimethylimidazo[1,2-b]pyridazin-6-yl)pyrido[1,2-a]pyrimidin-4-one | 20.0 | 60.0 | 20 | 20 |
| Mannitol | 514.2 | 474.25 | 364.19 | 1373.99 |
| Isomalt | 90.7 | 83.7 | 64.27 | 242.47 |
| Tartaric Acid fine powder | 92.0 | 120.5 | 92.00 | 92.00 |
| Sodium Benzoate micronized | 64.0 | 64.0 | 64.00 | 64.00 |
| Ascorbic Acid fine powder | 28.2 | 14.1 | 14.09 | 14.09 |
| Sucralose | 16.0 | 16.0 | 16.00 | 16.00 |
| Disodium edetate *2H$_2$O | 14.9 | 7.45 | 7.45 | 7.45 |
| PEG 6000 | 10.0 | 10.0 | 8.00 | 8.00 |
| Strawberry flavor | 150.0 | 150.0 | 150 | 150 |
| total | 1000.0 | 1000.0 | 800.0 | 2000.0 |

TABLE 19

Stabilities of oral solutions comprising circa 0.25 mg/ml of 7-(4,7-diazaspiro[2.5]octan-7-yl)-2-(2,8-dimethylimidazo[1,2-b]pyridazin-6-yl)pyrido[1,2-a]pyrimidin-4-one (indicated as API in the table) in vehicle solution of Composition 8a constituted with 80 ml water for injection (i.e. double distilled water devoid of electrolytes) or with potable water (comprising electrolytes).

| Days of storage at 5° C. | Composition 8a | | | |
|---|---|---|---|---|
| | with water for injection | | with potable water | |
| | API content [% LC] | API Purity [%] | API content [% LC] | API Purity [%] |
| 0 | 96.0 | 99.9 | 96.0 | 99.9 |
| 17 | 96.0 | 99.8 | 96.0 | 99.9 |
| 25 | 96.0 | 99.8 | 92.0 | 99.9 |
| 31 | 92.0 | 99.9 | 92.0 | 99.9 |

The invention claimed is:

1. A dry granulated powder blend for an oral solution, said dry granulated powder blend comprising 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;

a stabilizer comprising disodium ethylenediaminetetraacetate;

an antioxidant comprising ascorbic acid; and an acidifier comprising tartaric acid.

2. The dry granulated powder blend of claim 1, wherein the blend comprises:

1 to 10% wt of 7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;

disodium ethylenediaminetetraacetate at a ratio of 1:20 to 2:1 with 7-(4,7-diazaspiro[2.5]octan-7-yl)-2-(2,8-dimethylimidazo[1,2-b]pyridazin-6-yl)pyrido[1,2-a]pyrimidin-4-one;

ascorbic acid at a ratio of 1:10 to 4:1 with 7-(4,7-diazaspiro[2.5]octan-7-yl)-2-(2,8-dimethylimidazo[1,2-b]pyridazin-6-yl)pyrido[1,2-a]pyrimidin-4-one; and tartaric acid at a ratio of 1:2 to 15:1 with 7-(4,7-diazaspiro[2.5]octan-7-yl)-2-(2,8-dimethylimidazo[1,2-b]pyridazin-6-yl)pyrido[1,2-a]pyrimidin-4-one.

3. The dry granulated powder blend of claim 1, wherein the blend further comprises a diluent selected from the group consisting of lactose, starch, hydrolyzed starch, maltodextrin, microcrystalline cellulose, mannitol, isomalt, sorbitol, sucrose, dextrose, dibasic calcium phosphate, calcium sulfate, and combinations thereof.

4. The dry granulated powder blend of claim 3, wherein the diluent is mannitol and isomalt.

5. The dry granulated powder blend of claim 1, wherein the blend further comprises a preservative selected from the group consisting of sorbic acid and sodium benzoate.

6. The dry granulated powder blend of claim 5, wherein the preservative is sodium benzoate.

7. The dry granulated powder blend of claim 1, wherein the blend further comprises a poly(ethylene glycol) lubricant.

8. The dry granulated powder blend of claim 7, wherein the lubricant is PEG 6000.

9. An aqueous oral solution produced from a dry granulated powder blend, wherein said dry granulated powder blend comprises
   7-(4,7-diazaspiro[2.5]octan-7-yl)-2-(2,8-dimethylimidazo[1,2-b]pyridazin-6-yl)pyrido[1,2-a]pyrimidin-4-one or a pharmaceutically acceptable salt thereof;
   a stabilizer comprising disodium ethylenediaminetetraacetate;
   an antioxidant comprising ascorbic acid; and
   an acidifier comprising tartaric acid.

10. The aqueous oral solution of claim 9, wherein
    the stabilizer is at a ratio of 1:20 to 2:1 with 7-(4,7-diazaspiro[2.5]octan-7-yl)-2-(2,8-dimethylimidazo[1,2-b]pyridazin-6-yl)pyrido[1,2-a]pyrimidin-4-one;
    the antioxidant is at a ratio of 1:10 to 4:1 with 7-(4,7-diazaspiro[2.5]octan-7-yl)-2-(2,8-dimethylimidazo[1,2-b]pyridazin-6-yl)pyrido[1,2-a]pyrimidin-4-one; and
    the acidifier is at a ratio of 1:2 to 15:1 with 7-(4,7-diazaspiro[2.5]octan-7-yl)-2-(2,8-dimethylimidazo[1,2-b]pyridazin-6-yl)pyrido[1,2-a]pyrimidin-4-one.

11. The aqueous oral solution of claim 10, wherein the dry granulated powder blend comprises 1 to 10% wt of 7-(4,7-diazaspiro[2.5]octan-7-yl)-2-(2,8-dimethylimidazo[1,2-b]pyridazin-6-yl)pyrido[1,2-a]pyrimidin-4-one.

12. The aqueous oral solution of claim 9, wherein the dry granulated powder blend further comprises:
    a diluent comprising mannitol and isomalt;
    a preservative comprising sodium benzoate; and
    a lubricant comprising poly(ethylene glycol).

13. The aqueous oral solution of claim 12, wherein the poly(ethylene glycol) is PEG 6000.

14. The aqueous oral solution of claim 12, wherein
    the diluent is at a ratio of 4:1 to 70:1 with 7-(4,7-diazaspiro[2.5]octan-7-yl)-2-(2,8-dimethylimidazo[1,2-b]pyridazin-6-yl)pyrido[1,2-a]pyrimidin-4-one;
    the preservative is at a ratio of 1:10 to 8:1 with 7-(4,7-diazaspiro[2.5]octan-7-yl)-2-(2,8-dimethylimidazo[1,2-b]pyridazin-6-yl)pyrido[1,2-a]pyrimidin-4-one; and
    the lubricant is at a ratio of 1:20 to 2:1 with 7-(4,7-diazaspiro[2.5]octan-7-yl)-2-(2,8-dimethylimidazo[1,2-b]pyridazin-6-yl)pyrido[1,2-a]pyrimidin-4-one.

15. The aqueous oral solution of claim 12, wherein the dry granulated powder blend comprises:
    disodium ethylenediaminetetraacetate at a ratio of 1:12 to 1:1 with 7-(4,7-diazaspiro[2.5]octan-7-yl)-2-(2,8-dimethylimidazo[1,2-b]pyridazin-6-yl)pyrido[1,2-a]pyrimidin-4-one;
    ascorbic acid at a ratio of 1:6 to 3:2 with 7-(4,7-diazaspiro[2.5]octan-7-yl)-2-(2,8-dimethylimidazo[1,2-b]pyridazin-6-yl)pyrido[1,2-a]pyrimidin-4-one;
    tartaric acid at a ratio of 3:2 to 13:2 with 7-(4,7-diazaspiro[2.5]octan-7-yl)-2-(2,8-dimethylimidazo[1,2-b]pyridazin-6-yl)pyrido[1,2-a]pyrimidin-4-one;
    mannitol at a ratio of 45:6 to 55:2 with 7-(4,7-diazaspiro[2.5]octan-7-yl)-2-(2,8-dimethylimidazo[1,2-b]pyridazin-6-yl)pyrido[1,2-a]pyrimidin-4-one;
    isomalt at a ratio of 4:3 to 5:1 with 7-(4,7-diazaspiro[2.5]octan-7-yl)-2-(2,8-dimethylimidazo[1,2-b]pyridazin-6-yl)pyrido[1,2-a]pyrimidin-4-one;
    sodium benzoate at a ratio of 1:6 to 7:2 with 7-(4,7-diazaspiro[2.5]octan-7-yl)-2-(2,8-dimethylimidazo[1,2-b]pyridazin-6-yl)pyrido[1,2-a]pyrimidin-4-one; and
    poly(ethylene glycol) at a ratio of 1:12 to 1:1 with 7-(4,7-diazaspiro[2.5]octan-7-yl)-2-(2,8-dimethylimidazo[1,2-b]pyridazin-6-yl)pyrido[1,2-a]pyrimidin-4-one.

16. The aqueous oral solution of claim 15, wherein the dry granulated powder blend comprises 2 to 6% wt of 7-(4,7-diazaspiro[2.5]octan-7-yl)-2-(2,8-dimethylimidazo[1,2-b]pyridazin-6-yl)pyrido[1,2-a]pyrimidin-4-one.

17. The dry granulated powder blend of claim 1, wherein the blend further comprises:
    a diluent comprising mannitol or a mixture of mannitol and isomalt;
    a preservative comprising sodium benzoate; and
    a lubricant comprising poly(ethylene glycol).

18. The dry granulated powder blend of claim 17, wherein the poly(ethylene glycol) is PEG 6000.

19. The dry granulated powder blend of claim 17, wherein said blend comprises:
    a mixture of mannitol and isomalt at a ratio of 4:1 to 70:1 with 7-(4,7-diazaspiro[2.5]octan-7-yl)-2-(2,8-dimethylimidazo[1,2-b]pyridazin-6-yl)pyrido[1,2-a]pyrimidin-4-one;
    sodium benzoate at a ratio of 1:10 to 8:1 with 7-(4,7-diazaspiro[2.5]octan-7-yl)-2-(2,8-dimethylimidazo[1,2-b]pyridazin-6-yl)pyrido[1,2-a]pyrimidin-4-one; and
    poly(ethylene glycol) at a ratio of 1:20 to 2:1 with 7-(4,7-diazaspiro[2.5]octan-7-yl)-2-(2,8-dimethylimidazo[1,2-b]pyridazin-6-yl)pyrido[1,2-a]pyrimidin-4-one.

20. The dry granulated powder blend of claim 17, wherein said blend comprises:
    disodium ethylenediaminetetraacetate at a ratio of 1:12 to 1:1 with 7-(4,7-diazaspiro[2.5]octan-7-yl)-2-(2,8-dimethylimidazo[1,2-b]pyridazin-6-yl)pyrido[1,2-a]pyrimidin-4-one;
    ascorbic acid at a ratio of 1:6 to 3:2 with 7-(4,7-diazaspiro[2.5]octan-7-yl)-2-(2,8-dimethylimidazo[1,2-b]pyridazin-6-yl)pyrido[1,2-a]pyrimidin-4-one;
    tartaric acid at a ratio of 3:2 to 13:2 with 7-(4,7-diazaspiro[2.5]octan-7-yl)-2-(2,8-dimethylimidazo[1,2-b]pyridazin-6-yl)pyrido[1,2-a]pyrimidin-4-one;
    mannitol at a ratio of 45:6 to 55:2 with 7-(4,7-diazaspiro[2.5]octan-7-yl)-2-(2,8-dimethylimidazo[1,2-b]pyridazin-6-yl)pyrido[1,2-a]pyrimidin-4-one;
    isomalt at a ratio of 4:3 to 5:1 with 7-(4,7-diazaspiro[2.5]octan-7-yl)-2-(2,8-dimethylimidazo[1,2-b]pyridazin-6-yl)pyrido[1,2-a]pyrimidin-4-one;
    sodium benzoate at a ratio of 1:6 to 7:2 with 7-(4,7-diazaspiro[2.5]octan-7-yl)-2-(2,8-dimethylimidazo[1,2-b]pyridazin-6-yl)pyrido[1,2-a]pyrimidin-4-one; and
    poly(ethylene glycol) at a ratio of 1:12 to 1:1 with 7-(4,7-diazaspiro[2.5]octan-7-yl)-2-(2,8-dimethylimidazo[1,2-b]pyridazin-6-yl)pyrido[1,2-a]pyrimidin-4-one.

21. The dry granulated powder blend of claim 20, wherein the dry granulated powder blend comprises 2 to 6% wt of 7-(4,7-diazaspiro[2.5]octan-7-yl)-2-(2,8-dimethylimidazo[1,2-b]pyridazin-6-yl)pyrido[1,2-a]pyrimidin-4-one.

22. The dry granulated powder blend of claim 17, wherein
    the stabilizer is at a ratio of 1:8 to 3:4 with 7-(4,7-diazaspiro[2.5]octan-7-yl)-2-(2,8-dimethylimidazo[1,2-b]pyridazin-6-yl)pyrido[1,2-a]pyrimidin-4-one;
    the antioxidant is at a ratio of 1:5 to 7:5 with 7-(4,7-diazaspiro[2.5]octan-7-yl)-2-(2,8-dimethylimidazo[1,2-b]pyridazin-6-yl)pyrido[1,2-a]pyrimidin-4-one; and the acidifier is at a ratio of 4:3 to 9:2 with 7-(4,7-diazaspiro[2.5]octan-7-yl)-2-(2,8-dimethylimidazo[1,2-b]pyridazin-6-yl)pyrido[1,2-a]pyrimidin-4-one;

the diluent is at a ratio of 16:1 to 100:1 with 7-(4,7-diazaspiro[2.5]octan-7-yl)-2-(2,8-dimethylimidazo[1,2-b]pyridazin-6-yl)pyrido[1,2-a]pyrimidin-4-one;

the preservative is at a ratio of 1:2 to 13:4 with 7-(4,7-diazaspiro[2.5]octan-7-yl)-2-(2,8-dimethylimidazo[1,2-b]pyridazin-6-yl)pyrido[1,2-a]pyrimidin-4-one; and the lubricant is at a ratio of 1:5 to 5:4 with 7-(4,7-diazaspiro[2.5]octan-7-yl)-2-(2,8-dimethylimidazo[1,2-b]pyridazin-6-yl)pyrido[1,2-a]pyrimidin-4-one.

23. The dry granulated powder blend of claim 22, wherein the dry granulated powder blend comprises 1 to 5% wt of 7-(4,7-diazaspiro[2.5]octan-7-yl)-2-(2,8-dimethylimidazo[1,2-b]pyridazin-6-yl)pyrido[1,2-a]pyrimidin-4-one.

24. A dry granulated powder blend comprising
7-(4,7-diazaspiro[2.5]octan-7-yl)-2-(2,8-dimethylimidazo[1,2-b]pyridazin-6-yl)pyrido[1,2-a]pyrimidin-4-one;
disodium ethylenediaminetetraacetate;
ascorbic acid; and
tartaric acid.

25. The dry granulated powder blend of claim 24, wherein the disodium ethylenediaminetetraacetate is a dihydrate.

26. The dry granulated powder blend of claim 24, wherein the blend comprises
disodium ethylenediaminetetraacetate at a ratio of 1:12 to 1:1 with 7-(4,7-diazaspiro[2.5]octan-7-yl)-2-(2,8-dimethylimidazo[1,2-b]pyridazin-6-yl)pyrido[1,2-a]pyrimidin-4-one;
ascorbic acid at a ratio of 1:6 to 3:2 with 7-(4,7-diazaspiro[2.5]octan-7-yl)-2-(2,8-dimethylimidazo[1,2-b]pyridazin-6-yl)pyrido[1,2-a]pyrimidin-4-one; and
tartaric acid at a ratio of 3:2 to 13:2 with 7-(4,7-diazaspiro[2.5]octan-7-yl)-2-(2,8-dimethylimidazo[1,2-b]pyridazin-6-yl)pyrido[1,2-a]pyrimidin-4-one.

27. The dry granulated powder blend of claim 26, wherein the 7-(4,7-diazaspiro[2.5]octan-7-yl)-2-(2,8-dimethylimidazo[1,2-b]pyridazin-6-yl)pyrido[1,2-a]pyrimidin-4-one is 2 to 6% wt of the blend.

28. The dry granulated powder blend of claim 24, wherein the blend comprises
disodium ethylenediaminetetraacetate at a ratio of 1:8 to 3:4 with 7-(4,7-diazaspiro[2.5]octan-7-yl)-2-(2,8-dimethylimidazo[1,2-b]pyridazin-6-yl)pyrido[1,2-a]pyrimidin-4-one;
ascorbic acid at a ratio of 1:5 to 7:5 with 7-(4,7-diazaspiro[2.5]octan-7-yl)-2-(2,8-dimethylimidazo[1,2-b]pyridazin-6-yl)pyrido[1,2-a]pyrimidin-4-one; and
tartaric acid at a ratio of 4:3 to 9:2 with 7-(4,7-diazaspiro[2.5]octan-7-yl)-2-(2,8-dimethylimidazo[1,2-b]pyridazin-6-yl)pyrido[1,2-a]pyrimidin-4-one.

29. The dry granulated powder blend of claim 28, wherein the dry granulated powder blend comprises 1 to 5% wt of 7-(4,7-diazaspiro[2.5]octan-7-yl)-2-(2,8-dimethylimidazo[1,2-b]pyridazin-6-yl)pyrido[1,2-a]pyrimidin-4-one.

30. The dry granulated powder blend of claim 24 further comprising
mannitol;
isomalt;
sodium benzoate; and
poly(ethylene glycol).

31. The dry granulated powder blend of claim 30, wherein the poly(ethylene glycol) is PEG 6000.

32. The dry granulated powder blend of claim 30, wherein the blend comprises mannitol at a ratio of 45:6 to 55:2 with 7-(4,7-diazaspiro[2.5]octan-7-yl)-2-(2,8-dimethylimidazo[1,2-b]pyridazin-6-yl)pyrido[1,2-a]pyrimidin-4-one;
isomalt at a ratio of 4:3 to 5:1 with 7-(4,7-diazaspiro[2.5]octan-7-yl)-2-(2,8-dimethylimidazo[1,2-b]pyridazin-6-yl)pyrido[1,2-a]pyrimidin-4-one;
sodium benzoate at a ratio of 1:6 to 7:2 with 7-(4,7-diazaspiro[2.5]octan-7-yl)-2-(2,8-dimethylimidazo[1,2-b]pyridazin-6-yl)pyrido[1,2-a]pyrimidin-4-one; and
poly(ethylene glycol) at a ratio of 1:12 to 1:1 with 7-(4,7-diazaspiro[2.5]octan-7-yl)-2-(2,8-dimethylimidazo[1,2-b]pyridazin-6-yl)pyrido[1,2-a]pyrimidin-4-one.

33. The dry granulated powder blend of claim 32, wherein the 7-(4,7-diazaspiro[2.5]octan-7-yl)-2-(2,8-dimethylimidazo[1,2-b]pyridazin-6-yl)pyrido[1,2-a]pyrimidin-4-one is 2 to 6% wt of the blend.

34. The dry granulated powder blend of claim 30, wherein the blend comprises
2 to 6% wt 7-(4,7-diazaspiro[2.5]octan-7-yl)-2-(2,8-dimethylimidazo[1,2-b]pyridazin-6-yl)pyrido[1,2-a]pyrimidin-4-one;
disodium ethylenediaminetetraacetate dihydrate at a ratio of 1:12 to 1:1 with 7-(4,7-diazaspiro[2.5]octan-7-yl)-2-(2,8-dimethylimidazo[1,2-b]pyridazin-6-yl)pyrido[1,2-a]pyrimidin-4-one;
ascorbic acid at a ratio of 1:6 to 3:2 with 7-(4,7-diazaspiro[2.5]octan-7-yl)-2-(2,8-dimethylimidazo[1,2-b]pyridazin-6-yl)pyrido[1,2-a]pyrimidin-4-one;
tartaric acid at a ratio of 3:2 to 13:2 with 7-(4,7-diazaspiro[2.5]octan-7-yl)-2-(2,8-dimethylimidazo[1,2-b]pyridazin-6-yl)pyrido[1,2-a]pyrimidin-4-one;
mannitol at a ratio of 45:6 to 55:2 with 7-(4,7-diazaspiro[2.5]octan-7-yl)-2-(2,8-dimethylimidazo[1,2-b]pyridazin-6-yl)pyrido[1,2-a]pyrimidin-4-one;
isomalt at a ratio of 4:3 to 5:1 with 7-(4,7-diazaspiro[2.5]octan-7-yl)-2-(2,8-dimethylimidazo[1,2-b]pyridazin-6-yl)pyrido[1,2-a]pyrimidin-4-one;
sodium benzoate at a ratio of 1:6 to 7:2 with 7-(4,7-diazaspiro[2.5]octan-7-yl)-2-(2,8-dimethylimidazo[1,2-b]pyridazin-6-yl)pyrido[1,2-a]pyrimidin-4-one; and
PEG 6000 at a ratio of 1:12 to 1:1 with 7-(4,7-diazaspiro[2.5]octan-7-yl)-2-(2,8-dimethylimidazo[1,2-b]pyridazin-6-yl)pyrido[1,2-a]pyrimidin-4-one, and wherein the blend is constituted in water to form an aqueous solution with a pH of about 3.4.

35. An aqueous solution comprising the dry granulated blend of claim 24 constituted in said solution.

36. A kit for the preparation of a pharmaceutical composition comprising 7-(4,7-diazaspiro[2.5]octan-7-yl)-2-(2,8-dimethylimidazo[1,2-b]pyridazin-6-yl)pyrido[1,2-a]pyrimidin-4-one, or a pharmaceutically acceptable salt thereof, wherein the kit comprises the dry granulated powder blend of claim 1.

37. The kit of claim 36, wherein said kit further comprises a bottle.

38. The kit of claim 36, wherein said kit further comprises water as a solvent for constitution of the dry granulated powder blend of claim 1.

39. The aqueous oral solution of claim 35, wherein the aqueous oral solution has a pH of less than 4.

40. The aqueous oral solution of claim 39, wherein the aqueous oral solution has a pH of about 3.4.

41. The dry granulated powder blend of claim 31, wherein the blend comprises 2 to 6% wt of 7-(4,7-diazaspiro[2.5]octan-7-yl)-2-(2,8-dimethylimidazo[1,2-b]pyridazin-6-yl)pyrido[1,2-a]pyrimidin-4-one.

42. The dry granulated powder blend of claim 41, wherein the blend comprises 4 to 15% wt of tartaric acid.

43. The dry granulated powder blend of claim 41, wherein the blend comprises 40 to 70% wt of mannitol.

44. The dry granulated powder blend of claim 41, wherein the blend comprises 1 to 4% wt of ascorbic acid.

45. The dry granulated powder blend of claim 41, wherein the blend comprises 0.2 to 2% wt disodium ethylenediaminetetraacetate.

46. The dry granulated powder blend of claim 41, wherein the blend comprises 0.5 to 2% wt of PEG6000.

47. The dry granulated powder blend of claim 41, wherein the blend comprises 1 to 8% wt of sodium benzoate.

* * * * *